United States Patent
Ishibashi et al.

(10) Patent No.: US 11,384,043 B2
(45) Date of Patent: Jul. 12, 2022

(54) DIMETHYLCYCLOBUTANONE COMPOUNDS, DIMETHYLCYCLOBUTANE COMPOUNDS, AND PROCESSES FOR PREPARING THE SAME

(71) Applicant: Shin-Etsu Chemical Co., Ltd., Tokyo (JP)

(72) Inventors: Naoki Ishibashi, Niigata (JP); Yusuke Nagae, Niigata (JP); Takeshi Kinsho, Niigata (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 176 days.

(21) Appl. No.: 16/930,570

(22) Filed: Jul. 16, 2020

(65) Prior Publication Data
US 2021/0017112 A1    Jan. 21, 2021

(30) Foreign Application Priority Data

Jul. 17, 2019 (JP) .............................. JP2019-132136
Apr. 2, 2020 (JP) .............................. JP2020-067074

(51) Int. Cl.
*C07C 45/62* (2006.01)
*C07C 49/35* (2006.01)

(52) U.S. Cl.
CPC .............. *C07C 45/62* (2013.01); *C07C 49/35* (2013.01)

(58) Field of Classification Search
CPC ................................ C07C 45/62; C07C 49/35
See application file for complete search history.

(56) References Cited

FOREIGN PATENT DOCUMENTS

| DE | 2539048 A1 | 3/1976 |
|---|---|---|
| EP | 0051791 A1 | 5/1982 |
| GB | 1524682 A | 9/1978 |
| WO | 2015125785 A1 | 8/2015 |

OTHER PUBLICATIONS

Arai et al. "Identification of a Sex Pheromone Component of Pseudococcus cryptus4" Journal of Chemical Ecology, 29(10):2213-2223 (2003).
Bierl-Leonhardt et al. "Isolation, Identifigation and Synthesis of the Sex Pheromone of the Citrus Mealybug, *Planococcus Citri* (RISSO)" Tetrahedron Letters, 22(5):389-392 (1981).
Kawano et al. "Formal [4+2] cycloaddition of cyclobutanones bearing alkyne-cobalt complex at their 3-positions" Tetrahedron Letters, 53(4):432-434 (2012).
Millar et al. "identification of the Sex Pheromone of the Invasive Scale Acutaspis albopicta (Hemiptera: Diaspididae), Arriving in California on Shipments of Avocados From Mexico" Journal of Economic Entomology, 105(2):497-504 (2012).
Passaro et al. "Synthesis of the Female Sex Pheromone of the Citrus Mealybug, *Pianococcus citri*" Journal of Agricultural and Food Chemistry, 52(10):2896-2899 (2004).
Tabata et al. "Sex Pheromone of the Cotton Mealybug, *Phenacoccus solenopsis*, with an Unusual Cyclobutane Structure" Journal of Chemical Ecology, 42(11):1193-1200 (2016).
Zhang et al. "Chiral synthesis of maconelliol: a novel cyclobutanoid terpene alcohol from pink hibiscus mealybug, *Maconellicoccus hirsutus*" Tetrahedron Letters, 45(51):9401-9403 (2004).
Zhang et al. "Sex pheromone of the pink hibiscus mealybug, *Maconellicoccus hirsutus*, contains an unusual cyclobutanoid monoterpene" PNAS, 101(26):9601-9606 (2004).
Extended European Search Report corresponding to European Patent Application No. 20185859.4 (8 pages) (dated Nov. 30, 2020).

*Primary Examiner* — Sikarl A Witherspoon
(74) *Attorney, Agent, or Firm* — Myers Bigel, P.A.

(57) ABSTRACT

The present invention provides a process for preparing a dimethylcyclobutane compound of the following general formula (1A), the process comprising reacting a dimethylcyclobutanone compound of the following general formula (2) with a phosphonic ester compound of the following general formula (3) to produce an unsaturated ester compound of the following general formula (4), having a dimethylcyclobutane ring, and subjecting the unsaturated ester compound (4), having a dimethylcyclobutane ring, to a reduction reaction to produce the dimethylcyclobutane compound (1A).

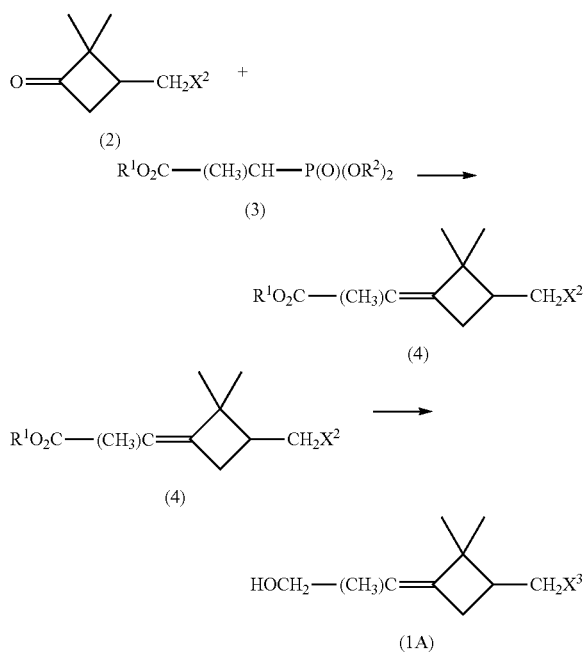

5 Claims, No Drawings

DIMETHYLCYCLOBUTANONE COMPOUNDS, DIMETHYLCYCLOBUTANE COMPOUNDS, AND PROCESSES FOR PREPARING THE SAME

TECHNICAL FIELD

The present invention relates to dimethylcyclobutanone compounds and dimethylcyclobutane compounds, both of which are useful intermediates for synthesis of insect sex pheromones, and processes for preparing the dimethylcyclobutanone compounds and the dimethylcyclobutane compounds.

BACKGROUND ART

Insect sex pheromones are biologically active substances which usually have a function of attracting male individuals to female individuals, and exhibit high attracting activities in small amounts. Sex pheromones are widely used as a means of forecasting outbreaks of pests and confirming geographic spread (invasion into a specific area), and as a means of controlling pests. Widely used methods are a mass trapping method, a lure & kill or attract & kill method, a lure & infect or attract & infect method, and a mating disruption method. Before practical use of sex pheromones, economical production of a sufficient amount of a pheromone substance is required for basic research and also for applications.

An example of a unique structure among the chemical structures for the sex pheromones is a cyclobutane structure. For instance, the sex pheromone of *Planococcus citri* (generic name: *Citrus* mealybug) which is an economically serious pest and spread widely throughout the world to infest *citrus* is (+)-cis-(3-isopropenyl-2,2-dimethylcyclobutyl) methyl acetate, as reported by Bierl-Leonhardt et al. (Non-Patent Literature 1, as listed below). The sex pheromones of *Pseudococcus cryptyptus* (generic name: *Citriculus* mealybug) and *Acutaspis albopicta* (generic name: *Albopicta* scale) also have a structure of cis-(3-isopropenyl-2,2-dimethylcyclobutyl)methyl ester of a carboxylic acid, similar to the sex pheromone of *Citrus* mealybugs (Non-Patent Literatures 2 and 3, as listed below). Further, species such as *Maconellicoccus hirstus* (generic name: Pink hibiscus mealybug) and *Phenacoccus solenopsis* (generic name: Cotton mealybug) are also known, the sex pheromone of which is (3-isopropylidene-2,2-dimethylcyclobutyl)methyl ester, in which a position of a double bond is different from that of the sex pheromone of *Citrus* mealybug (Non-Patent Literatures 4 and 5, as listed below).

In typical methods for preparing sex pheromones having these cyclobutane structures, pinene is used as a starting material. For instance, the following method is reported by Passaro et al.; pinene was oxidized to produce verbenol or verbenone, which are further oxidized to cleave the double bond, followed by methylation of the ketone group, reduction of the carboxylic group and acetylation to obtain the sex pheromone of *Citrus* mealybug (Non-Patent Literature 6, as listed below). The following method is reported by Zhang et al.; verbenone is oxidized, followed by methylation of a the ketone, lactonization and cleavage of the lactone ring to construct an isopropylidene group, and reduction of the carboxylic group to produce (3-isopropylidene-2,2-dimethylcyclobutyl)methanol which corresponds to the alcohol moiety in the sex pheromone of Pink hibiscus mealybug and Cotton mealybug (Non-Patent Literature 7, as listed below). Matsusu et al., synthesize 3-benzyloxymethyl-2,2-dimethylcyclobutanone having a partial structure common with the sex pheromone of *Citrus* mealybug, by the reaction of a ketene iminium which is prepared from an amide and a trifluoromethanesulfonic anhydride with an allyl benzyl ether (Non-Patent Document 8).

LIST OF THE PRIOR ART

Non-Patent Literatures

[Non-Patent Literature 1] Tetrahedron. Lett. 22, 389 (1981)
[Non-Patent Literature 2] J. Chem. Ecol. 29, 2213 (2003)
[Non-Patent Literature 3] J. Econ. Entomol. 105, 497 (2012)
[Non-Patent Literature 4] Proc. Natl. Acad. Sci. 101, 9601 (2004)
[Non-Patent Literature 5]. Chem. Ecol. 42, 1193 (2016)
[Non-Patent Literature 6] J. Agric. Food Chem. 2004, 52, 2896 (2004)
[Non-Patent Literature 7] Tetrahedron. Lett. 45, 9401 (2004)
[Non-Patent Literature 8] Tetrahedron. Lett. 53, 432 (2012)

SUMMARY OF THE INVENTION

However, lead tetraacetate or chromium oxide is used for the oxidation of pinene into verbenol or verbenone in the method described in Non-Patent Literature 6, leaving a large amount of heavy metal waste which is harmful and gives high environmental burden. Further, these oxidizing agents may cause explosion and are not industrially practical. An expensive ruthenium catalyst is used to further oxidize verbenol or verbenone, and, therefore, industrial practice is difficult in view of the economy. The oxidation of pinene into verbenone is carried out in an oxygen atmosphere in the production method described in Non-Patent Literature 7. This is difficult to be industrially practiced in view of the safety and requires a reaction time of so many days of 7, which is inefficient and uneconomical. Further, an expensive ruthenium catalyst is used for the oxidation of verbenone, which is uneconomical, as in Non-Patent Literature 6. In the process for preparing a cyclobutanone having a partial structure common with the sex pheromone of *Citrus* mealybug described in Non-Patent Literature 8, handling is difficult because of a high reactivity, and industrial implementation is difficult due to use of expensive trifluoromethanesulfonic anhydride.

An efficient and industrially practical production method capable of supplying a sufficient amount of the pheromone substances is eagerly wanted for basic biological and agricultural research on sex pheromone compounds having a cyclobutane structure, like the sex pheromone of *Citrus* mealybug, and further for the purpose of application and practical use.

The present invention has been made in these circumstances, and aims it to provide an efficient and industrially practical method for producing dimethylcyclobutanone compound and a dimethylcyclobutane compound, both of which are useful as a synthetic intermediate for sex pheromone compounds having a cyclobutane structure, and to provide these compounds.

As a result of the intensive researches in order to solve the problems above, the present inventors have found a process for efficiently and industrially practically preparing sex pheromones having a cyclobutane structure, using dimethylcyclobutane compounds of the following general formula (1A), (1B), (2), (5), (6), and (1) described hereinafter, without an oxidation reaction which is difficult to carry out industrially in view of the safety, the economy and the environmental burden, and thus have completed the present invention.

According to one aspect of the present invention, there is provided a process for preparing a dimethylcyclobutane compound of the following general formula (1A):

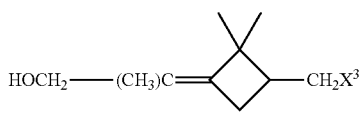
(1A)

wherein $X^3$ represents a hydroxyl group, an alkanesulfonyloxy group having 1 to 10 carbon atoms, an arenesulfonyloxy group having 6 to 20 carbon atoms, an alkoxy group having 1 to 12 carbon atoms, an aryloxy group having 6 to 12 carbon atoms, a silyloxy group having 3 to 20 carbon atoms or a halogen atom, the process comprising reacting a dimethylcyclobutanone compound of the following general formula (2):

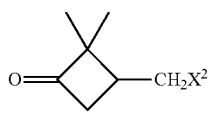
(2)

wherein $X^2$ represents a hydroxyl group, an acyloxy group having 1 to 10 carbon atoms including a carbon atom of a carbonyl group, an alkoxycarbonyloxy group having 2 to 10 carbon atoms including a carbon atom of a carbonyl group, an alkanesulfonyloxy group having 1 to 10 carbon atoms, an arenesulfonyloxy group having 6 to 20 carbon atoms, an alkoxy group having 1 to 12 carbon atoms, an aryloxy group having 6 to 12 carbon atoms, a silyloxy group having 3 to 20 carbon atoms or a halogen atom, with a phosphonic ester compound of the following general formula (3):

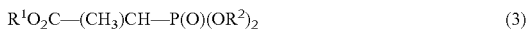

wherein $R^1$ and $R^2$ represent, independently of each other, a monovalent hydrocarbon group having 1 to 10 carbon atoms, especially in an olefination reaction, preferably a Horner Wadsworth-Emmons reaction, to produce an unsaturated ester compound of the following general formula (4), having a dimethylcyclobutane ring,

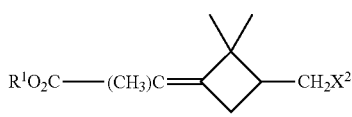
(4)

wherein $R^1$ and $X^2$ are as defined above; and subjecting the unsaturated ester compound (4), having a dimethylcyclobutane ring, to a reduction reaction to produce the dimethylcyclobutane compound (1A).

According to another aspect of the present invention, there is provided a process for preparing a dimethylcyclobutane compound of the following general formula (1B):

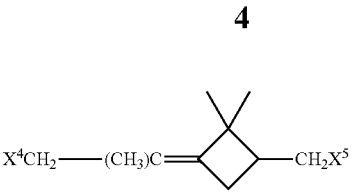
(1B)

wherein $X^4$ represents an acyloxy group having 1 to 10 carbon atoms including a carbon atom of a carbonyl group, an alkoxycarbonyloxy group having 2 to 10 carbon atoms including a carbon atom of a carbonyl group, an alkanesulfonyloxy group having 1 to 10 carbon atoms, an arenesulfonyloxy group having 6 to 20 carbon atoms, an alkoxy group having 1 to 12 carbon atoms, an aryloxy group having 6 to 12 carbon atoms, a silyloxy group having 3 to 20 carbon atoms, a trialkylphosphonio group having 3 to 30 carbon atoms, a triarylphosphonio group having 12 to 30 carbon atoms or a halogen atom; and $X^5$ represents a hydroxyl group, an acyloxy group having 1 to 10 carbon atoms including a carbon atom of a carbonyl group, an alkoxycarbonyloxy group having 2 to 10 carbon atoms including a carbon atom of a carbonyl group, an alkanesulfonyloxy group having 1 to 10 carbon atoms, an arenesulfonyloxy group having 6 to 20 carbon atoms, an alkoxy group having 1 to 12 carbon atoms, an aryloxy group having 6 to 12 carbon atoms, a silyloxy group having 3 to 20 carbon atoms or a halogen atom, the process comprising the aforesaid process for preparing the dimethylcyclobutane compound (1A); and changing the hydroxyl group and, optionally, $X^3$ in the dimethylcyclobutane compound (1A) to produce the dimethylcyclobutane compound (1B).

According to another aspect of the present invention, there is provided a process for preparing an isopropenyl dimethylcyclobutane compound of the following general formula (5):

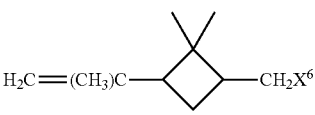
(5)

wherein $X^6$ represents a hydroxyl group, an acyloxy group having 1 to 10 carbon atoms including a carbon atom of a carbonyl group, an alkoxycarbonyloxy group having 2 to 10 carbon atoms including a carbon atom of a carbonyl group, an alkanesulfonyloxy group having 1 to 10 carbon atoms, an arenesulfonyloxy group having 6 to 20 carbon atoms, an alkoxy group having 1 to 12 carbon atoms, an aryloxy group having 6 to 12 carbon atoms, a silyloxy group having 3 to 20 carbon atoms or a halogen atom, and/or an isopropylidene dimethylcyclobutane compound of the following general formula (6):

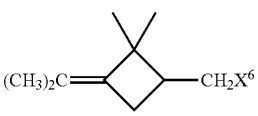
(6)

wherein $X^6$ is as defined above, the process comprising subjecting a dimethylcyclobutane compound of the following general formula (1):

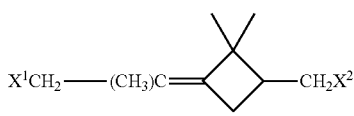

wherein $X^1$ represents a hydroxyl group, an acyloxy group having 1 to 10 carbon atoms including a carbon atom of a carbonyl group, an alkoxycarbonyloxy group having 2 to 10 carbon atoms including a carbon atom of a carbonyl group, an alkanesulfonyloxy group having 1 to 10 carbon atoms, an arenesulfonyloxy group having 6 to 20 carbon atoms, an alkoxy group having 1 to 12 carbon atoms, an aryloxy group having 6 to 12 carbon atoms, a silyloxy group having 3 to 20 carbon atoms, a trialkylphosphonio group having 3 to 30 carbon atoms, a triarylphosphonio group having 12 to 30 carbon atoms or a halogen atom; and $X^2$ is as defined above, to a reduction reaction to produce the isopropenyl dimethylcyclobutane compound (5) and/or the isopropylidene dimethylcyclobutane compound (6).

According to another aspect of the present invention, there is provided a process for preparing an isopropenyl dimethylcyclobutane compound (5') and/or an isopropylidene dimethylcyclobutane compound (6'), the process comprising the aforesaid process for preparing the isopropenyl dimethylcyclobutane compound (5) and/or the isopropylidene dimethylcyclobutane compound (6); and changing a specific group, $X^6$, in the isopropenyl dimethylcyclobutane compound (5) and/or the isopropylidene dimethylcyclobutane compound (6) to another group, $X^{6'}$, among the options for $X^6$ defined above, to produce the isopropenyl dimethylcyclobutane compound (5') and/or the isopropylidene dimethylcyclobutane compound (6').

According to another aspect of the present invention, there is provided a dimethylcyclobutane compound of the following general formula (1):

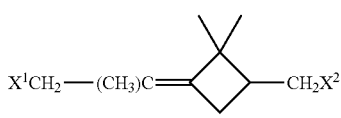

wherein $X^1$ and $X^2$ are as defined above.

According to another aspect of the present invention, in particular, $X^1$ in the dimethylcyclobutane compound (1) is a hydroxyl group; and $X^2$ represents a hydroxyl group, an alkanesulfonyloxy group having 1 to 10 carbon atoms, an arenesulfonyloxy group having 6 to 20 carbon atoms, an alkoxy group having 1 to 12 carbon atoms, an aryloxy group having 6 to 12 carbon atoms, a silyloxy group having 3 to 20 carbon atoms or a halogen atom.

According to another aspect of the present invention, in particular, $X^1$ in the dimethylcyclobutane compound (1) represents an acyloxy group having 1 to 10 carbon atoms including a carbon atom of a carbonyl group, an alkoxycarbonyloxy group having 2 to 10 carbon atoms including a carbon atom of a carbonyl group, an alkanesulfonyloxy group having 1 to 10 carbon atoms, an arenesulfonyloxy group having 6 to 20 carbon atoms, an alkoxy group having 1 to 12 carbon atoms, an aryloxy group having 6 to 12 carbon atoms, a silyloxy group having 3 to 20 carbon atoms, a trialkylphosphonio group having 3 to 30 carbon atoms, a triarylphosphonio group having 12 to 30 carbon atoms or a halogen atom.

According to another aspect of the present invention, there is provided a process for preparing a dimethylcyclobutanone compound of the following general formula (2A):

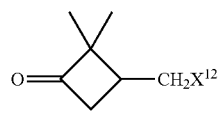

wherein $X^1$ represents an acyloxy group having 1 to 10 carbon atoms including a carbon atom of a carbonyl group, an alkoxycarbonyloxy group having 2 to 10 carbon atoms including a carbon atom of a carbonyl group, an alkanesulfonyloxy group having 1 to 10 carbon atoms, an arenesulfonyloxy group having 6 to 20 carbon atoms, an alkoxy group having 1 to 12 carbon atoms, an aryloxy group having 6 to 12 carbon atoms, a silyloxy group having 3 to 20 carbon atoms or a halogen atom, the process comprising reacting an acid halide of the following general formula (7):

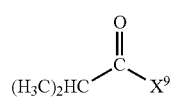

wherein $X^9$ represents a halogen atom,
with an allyl compound of the following general formula (8):

wherein $X^{12}$ is as defined above,
in the presence of a base to produce the dimethylcyclobutanone compound (2A).

According to another aspect of the present invention, there is provided a dimethylcyclobutanone compound of the following general formula (2B):

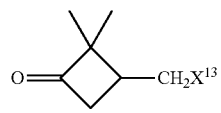

wherein $X^{13}$ represents an acyloxy group having 3 to 10 carbon atoms including a carbon atom of a carbonyl group, an alkoxycarbonyloxy group having 2 to 10 carbon atoms including a carbon atom of a carbonyl group, an alkanesulfonyloxy group having 1 to 10 carbon atoms, an arenesulfonyloxy group having 6 to 20 carbon atoms, an alkoxy group having 2 to 12 carbon atoms with a benzyloxy group being precluded, an aryloxy group having 6 to 12 carbon atoms, or a silyloxy group having 3 to 20 carbon atoms.

According to the present invention, a sex pheromone compound having a cyclobutane structure can be prepared efficiently and industrially without an oxidation reaction which are difficult to carry out industrially in view of safety, economy and environmental burden. The present invention is applicable to the preparation of cis-(3-isopropenyl-2,2-dimethylcyclobutyl)methyl ester which is the sex pheromone of *Citrus* mealybug, *Citriculus* mealybug and *Albopicta* scale, and (3-isopropylidene-2,2-dimethylcyclobutyl)ethyl ester which is the sex pheromone of Pink hibiscus mealybug and Cotton mealybug.

DETAILED DESCRIPTION OF THE INVENTION

In the chemical formulae of the intermediates, the reagents and the target compounds in the present specification, there may be some isomers having different substitution positions on the structure, or stereoisomers such as enantiomers or diastereoisomers. Unless otherwise stated, in each case, each chemical formula shall be interpreted to represent all of these isomers. Further, these isomers may be an isomer or a combination thereof.

[I] Dimethylcyclobutane Compound (1)

First, the dimethylcyclobutane compound (1) will be explained. The dimethylcyclobutane compound (1) is represented by the following formula.

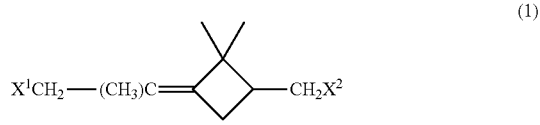
(1)

$X^1$ represents a hydroxyl group, an acyloxy group having 1 to 10 carbon atoms including a carbon atom of a carbonyl group, an alkoxycarbonyloxy group having 2 to 10 carbon atoms including a carbon atom of a carbonyl group, an alkanesulfonyloxy group having 1 to 10 carbon atoms, an arenesulfonyloxy group having 6 to 20 carbon atoms, an alkoxy group having 1 to 12 carbon atoms, an aryloxy group having 6 to 12 carbon atoms, a silyloxy group having 3 to 20 carbon atoms, a trialkylphosphonio group having 3 to 30 carbon atoms, a triarylphosphonio group having 12 to 30 carbon atoms or a halogen atom.

$X^2$ represents a hydroxyl group, an acyloxy group having 1 to 10 carbon atoms including a carbon atom of a carbonyl group, an alkoxycarbonyloxy group having 2 to 10 carbon atoms including a carbon atom of a carbonyl group, an alkanesulfonyloxy group having 1 to 10 carbon atoms, an arenesulfonyloxy group having 6 to 20 carbon atoms, an alkoxy group having 1 to 12 carbon atoms, an aryloxy group having 6 to 12 carbon atoms, a silyloxy group having 3 to 20 carbon atoms or a halogen atom.

$X^1$ and $X^2$ is independently selected from the groups above.

Examples of an acyloxy group having 1 to 10 carbon atoms including a carbon atom of a carbonyl group include linear aliphatic acyloxy groups such as a formyloxy group, an acetoxy (AcO) group, a propanoyloxy group, a butanoyloxy group, a pentanoyloxy group, a hexanoyloxy group, a heptanoyloxy group, an octanoyloxy group, a nonanoyloxy group, a decanoyloxy group, a crotonyloxy group; branched aliphatic acyloxy groups such as a 2-methylpropanoyloxy group, a pivaloyloxy group, a 2-methylbutanoyloxy group, a 3-methyl-2-butenoyloxy group, and a 3-methyl-3-butenoyloxy group; halogenated acyloxy groups such as a trichloroacetoxy group and a trifluoroacetoxy group; and aromatic acyloxy groups such as a benzoyloxy group; and further may include an acyloxy group having an isomeric relation with the groups mentioned above. A part of the hydrogen atoms of these acyloxy groups may be substituted with a methyl group, an ethyl group or a halogen atom. Particularly preferred examples of an acyloxy group having 1 to 10 carbon atoms including a carbon atom of a carbonyl group include a formyloxy group, an acetoxy group, a propanoyloxy group, a pivaloyloxy group, a 2-methylbutanoyloxy group, and a benzoyloxy group in view of the availability.

Examples of an alkoxycarbonyloxy group having 2 to 10 carbon atoms including a carbon atom of a carbonyl group include includes linear saturated alkoxycarbonyl groups such as a methoxycarbonyloxy group, an ethoxycarbonyloxy group, an n-propoxycarbonyloxy group, an n-butoxycarbonyloxy group, an n-pentyloxycarbonyloxy group, an n-hexyloxycarbonyloxy group, an n-heptyloxycarbonyloxy group, an n-octyloxycarbonyloxy group, an n-nonyloxycarbonyloxy group, an n-decyloxycarbonyloxy group; branched saturated alkoxycarbonyloxy groups such as an isopropoxycarbonyloxy group and t-butoxycarbonyloxy group; linear unsaturated alkoxycarbonyloxy groups such as a 2-propenyloxycarbonyloxy group and 2-propynyloxycarbonyloxy group; branched unsaturated alkoxycarbonyloxy groups such as a 2-methyl-2-propenyloxycarbonyloxy group; cyclic alkoxycarbonyloxy groups such as a cyclopropyloxycarbonyloxy group, a 2-methylcyclopropyloxycarbonyloxy group, a cyclobutyloxycarbonyloxy group, and a cyclopentyloxycarbonyloxy group; alkoxycarbonyloxy groups having an aromatic ring such as a benzyloxycarbonyloxy group and a paramethoxybenzyloxycarbonyloxy group; oxyalkoxycarbonyloxy groups such as a methoxymethoxycarbonyloxy group, a benzyloxymethoxycarbonyloxy group, and a paramethoxybenzyloxymethoxycarbonyloxy group; and halogenated alkoxycarbonyloxy groups such as 2,2,2-trichloroethoxycarbonyloxy group; and further may include an alkoxycarbonyloxy group having an isomeric relation with the groups mentioned above. A part of the hydrogen atoms of these alkoxycarbonyloxy groups may be substituted with a methyl group, an ethyl group or a halogen atom. Particularly preferred examples of an alkoxycarbonyloxy group having 2 to 10 carbon atoms including a carbon atom of a carbonyl group include a methoxycarbonyloxy group, an ethoxycarbonyloxy group, and an n-propoxycarbonyloxy group in view of the availability.

Examples of an alkanesulfonyloxy group having 1 to 10 carbon atoms include a methanesulfonyloxy (MsO) group, an ethanesulfonyloxy group, a 1-butanesulfonyloxy group, a 1-pentanesulfonyloxy group, a 1-hexanesulfonyloxy group, a 1-heptanesulfonyloxy group, a 1-octanesulfonyloxy group, a 1-nonanesulfonyloxy group, a 1-decanesulfonyloxy group, an allylsulfonyloxy group, a 10-camphorsulfonyloxy group, a trifluoromethanesulfonyloxy group, and an α-benzylsulfonyloxy group; and further may include an alkanesulfonyloxy group having an isomeric relation with the groups mentioned above. A part of the hydrogen atoms of these alkanesulfonyloxy groups may be substituted with a methyl group, an ethyl group or a halogen atom. Particularly preferred examples of an alkanesulfonyloxy group having 1 to 10 carbon atoms include a methanesulfonyloxy group and an ethanesulfonyloxy group in view of the availability.

Examples of an arenesulfonyloxy group having 6 to 20 carbon atoms include a benzenesulfonyloxy group, a 4-chlorobenzenesulfonyloxy group, a 4-methoxybenzenesulfonyloxy group, a 2-nitrobenzenesulfonyloxy group, a 2,4,6-trimethylbenzenesulfonyloxy group, a paratoluenesulfonyloxy (TsO) group, a 1-naphthalenesulfonyloxy group, and a 2-naphthalenesulfonyloxy group; and further may include an arenesulfonyloxy group having an isomeric relation with the groups mentioned above. A part of the hydrogen atoms of these arenesulfonyloxy groups may be substituted with a methyl group, an ethyl group or a halogen atom. Particularly preferred examples of an arenesulfonyloxy group having 6 to 20 carbon atoms include a benzenesulfonyloxy group and a paratoluenesulfonyloxy group in view of the availability.

Examples of an alkoxy group having 1 to 12 carbon atoms include linear saturated alkoxy groups such as a methoxy (MeO) group, an ethoxy (EtO) group, an n-propoxy (PrO) group, an n-butoxy (BuO) group, an n-pentyloxy (PenO) group, an n-hexyloxy (HexO) group, an n-heptyloxy (HepO) group, an n-octyloxy (OctO) group, an n-nonyloxy (NonO) group, an n-decyloxy (DecO) group, an n-undecyloxy group, and an n-dodecyloxy group; branched saturated alkoxy groups such as an isopropoxy (i-PrO) group, an isobutyloxy (i-BuO) group, and a t-butoxy (t-BuO) group; linear unsaturated alkoxy groups such as a 2-propenyloxy group and a 2-propynyloxy group; branched unsaturated alkoxy groups such as a 2-methyl-2-propenyloxy group; cyclic alkoxy groups such as a cyclopropyloxy group, a 2-methylcyclopropyloxy group, a cyclobutyloxy group, a cyclopentyloxy group, and a cyclohexyloxy (c-HexO) group; alkoxy groups having an aromatic ring such as a benzyloxy (BnO) group and a paramethoxybenzyloxy group; oxyalkoxy groups such as a methoxymethoxy (MOMO) group, a 2-methoxyethoxymethoxy group, a benzyloxymethoxy group, a paramethoxybenzyloxymethoxy group, a 1-ethoxyethoxy (EEO) group, a 1-allyloxyethoxy group, and a tetrahydropyran-2-yloxy (THPO) group; and halogenated alkoxy groups such as a 2,2,2-trichloroethoxy group and a pentafluoroetboxy group; and further may include an alkoxy group having an isomeric relation with the groups mentioned above. A part of the hydrogen atoms of these alkoxy groups may be substituted with a methyl group, an ethyl group or a halogen atom.

Particularly preferred examples of an alkoxy group having 1 to 12 carbon atoms include a methoxy group, an ethoxy group, a 2-propenyloxy group, a methoxymethoxy group, a 1-ethoxyethoxy group, a 1-allyloxyethoxy group, and a tetrahydropyran-2-yloxy group in view of ease of preparation.

Examples of an aryloxy group having 6 to 12 carbon atoms include a phenoxy (PhO) group, a 4-chlorophenoxy group, a 4-methoxyphenoxy group, a naphthoxy group, and a 4-biphenyloxy group; and further may include an aryloxy group having an isomeric relation with the groups mentioned above. A part of the hydrogen atoms of these aryloxy groups may be substituted with a methyl group, an ethyl group or a halogen atom. Particularly preferred examples of an aryloxy group having 6 to 12 carbon atoms include a phenoxy group and a naphthoxy group in view of the availability.

Examples of a silyloxy group having 3 to 20 carbon atoms include trialkylsilyloxy groups such as a trimethylsilyloxy (TMSO) group, a triethylsilyloxy (TESO) group, a triisopropylsilyloxy (TIPSO) group, and a t-butydimethylsilyloxy (TBSO) group; monoalkyldiarylsilyloxy groups such as a t-butyldiphenylsilyloxy (TBDPSO) group; and further may include a silyloxy group having an isomeric relation with the groups mentioned above. A part of the hydrogen atoms of these silyloxy groups may be substituted with a methyl group, an ethyl group or a halogen atom. Particularly preferred examples of a silyloxy group having 3 to 20 carbon atoms include a trimethylsilyloxy group, a triethylsilyloxy group, a triisopropylsilyloxy group, and a t-butyldimethylsilyloxy group in view of the availability.

Examples of a trialkylphosphonio group having 3 to 30 carbon atoms include a trimethylphosphonio group, a triethylphosphonio group, a tripropylphosphonio group, a tributylphosphonio group, a tripentylphosphonio group, a trihexylphosphonio group, a triheptylphosphonio group, a trioctylphosphonio group, a trinonylphosphonio group, a tridecylphosphonio group, and a tricyclohexylphosphonio group.

Particularly preferred examples of a trialkylphosphonio group having 3 to 30 carbon atoms include a tributylphosphonio group, a tricyclohexylphosphonio group, and a trioctylphosphonio group in view of the availability.

Examples of a triarylphosphonio group having 12 to 30 carbon atoms include a triphenylphosphonio group, a tri(2-methylphenyl)phosphonio group, a trifurylphosphonio group, and a tri(1-naphthyl)phosphonio group.

Particularly preferred examples of a triarylphosphonio group having 12 to 30 carbon atoms include a triphenylphosphonio group and a tri (2-methylphenyl)phosphonio group in view of the availability.

Examples of a halogen atom include a chlorine atom, a bromine atom, and an iodine atom. Particularly preferred examples of a halogen atom include a chlorine atom and a bromine atom in view of the availability.

Examples of the dimethylcyclobutane compound (1) include a (S,Z) form of the dimethylcyclobutane compound of the following general formula (4-1), a (R,Z) form of a dimethylcyclobutane compound of the following general formula (4-2), a (S,E) form of a dimethylcyclobutane compound of the following general formula (4-3), a (RE) form of the dimethylcyclobutane compound of the following general formula (4-4), and the racemates, diastereomeric mixtures and scalemic mixtures thereof.

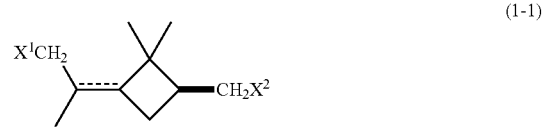

(1-1)

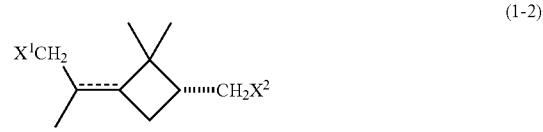

(1-2)

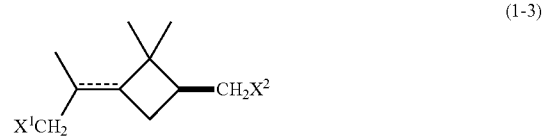

(1-3)

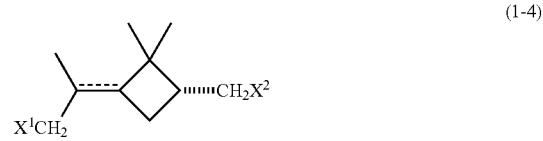

(1-4)

Examples of a dimethylcyclobutane compound include a dimethylcyclobutane compound having a hydroxyl group and an alkoxy group, a dimethylcyclobutane compound having an acyloxy group and an alkoxy group, a dimethylcyclobutane compound having a halogen atom and an alkoxy group, a dimethylcyclobutane compound having a phosphonio group and an alkoxy group, a dimethylcyclobutane compound having two hydroxyl groups, a dimethylcyclobutane compound having two acyloxy groups, a dimethylcyclobutane compound having two halogen atoms, a dimethylcyclobutane compound having a phosphonio group and a hydroxyl group, a dimethylcyclobutane compound having a halogen atom, and an acyloxy group.

Examples of a dimethylcyclobutane compound having a hydroxyl group and an alkoxy group include 2-(3-alkoxymethyl-2,2-dimethylcyclobutylidene)propan-1-ol compounds such as 2-(3-benzyloxymethyl-2,2-dimethylcyclobutylidene)propan-1-ol, 2-(3-methoxymethoxymethyl-2,2-dimethylcyclobutylidene)propan-1-ol, and 2-[2,2-dimethyl-3-(tetrahydropyran-2-yloxymethyl)cyclobutylidene]propan-1-ol; and 2-[3-(1-ethoxyethoxy)methyl-2,2-dimethylcyclobutylidene]propan-1-ol compounds (see Examples 11, 12, 13 and 16 below).

Examples of a dimethylcyclobutane compound having an acyloxy group and an alkoxy group include 2-(3-alkoxymethyl-2,2-dimethylcyclobutylidene)propyl acylate compounds such as 2-(3-methoxymethoxymethyl-2,2-dimethylcyclobutylidene)propyl acetate and 2-[2,2-dimethyl-3-(tetrahydropyran-2-yloxymethyl)cyclobutylidene]propyl acetate (see Examples 20 and 21 below).

Examples of a dimethylcyclobutane compound having a halogen atom and an alkoxy group include 1-alkoxymethyl-3-(2-halo-1-methylethylidene)-2,2-dimethylcyclobutane compounds such as [3-(2-chloro-1-methylethylidene)-2,2-dimethylcyclobutyl]methoxymethylbenzene and [3-(2-bromo-1-methylethylidene)-2,2-dimethylcyclobutyl]methoxymethylbenzene (see Examples 17 and 18 below).

Examples of a dimethylcyclobutane compound having a phosphonio group and an alkoxy group include [2-(3-alkoxymethyl-2,2-dimethylcyclobutylidene)propyl]triarylphosphonium compounds such as 2-(3-benzyloxymethyl-2,2-dimethylcyclobutylidene)propyltriphenylphosphonium (see Example 19 below).

Examples of a dimethylcyclobutane compound having two hydroxyl groups include 2-(3-hydroxymethyl-2,2-dimethylcyclobutylidene)propen-1-ol (see Examples 14, 15, 22, and 23 below).

Examples of a dimethylcyclobutane compound having two acyloxy groups include [3-(2-acyloxy-1-methylethylidene)-2,2-dimethylcyclobutyl]methyl acylate compounds such as [3-(2-acetoxy-1-methylethylidene)-2,2-dimethylcyclobutyl]methyl acetate and (3-[2-(2-methylbutanoyloxy)-1-methylethylidene]-2,2-dimethylcyclobutyl)methy 2-methylbutanoate (see Examples 24 and 25 below).

Examples of a dimethylcyclobutane compound having two halogen atoms include 1-halomethyl-3-(2-halo-1-methylethylidene)-2,2-dimethylcyclobutane compounds such as 1-chloromethyl-3-(2-chloro-1-methylethylidene)-2,2-dimethylcyclobutane (see Example 26 below).

Examples of a dimethylcyclobutane compound having a phosphonio group and a hydroxyl group include [2-(3-hydroxymethyl-2,2-dimethylcyclobutylidene)propyl]triarylphosphonium compounds such as triphenyl[2-(3-hydroxymethyl-2,2-dimethylcyclobutylidene)propy]phosphonium (see Example 27 below).

Examples of a dimethylcyclobutane compound having a halogen atom and an acyloxy group include [2,2-dimethyl-3-(2-halo-1-methylethylidene)cyclobutyl]methyl acylate compounds such as [2,2-dimethyl-3-(2-bromo-1-methylethylidene)cyclobutyl]methyl acetate (see Example 28 below).

Examples of the dimethylcyclobutane compound (1) include, for example, a dimethylcyclobutane compound of the following formula in addition to those mentioned above.

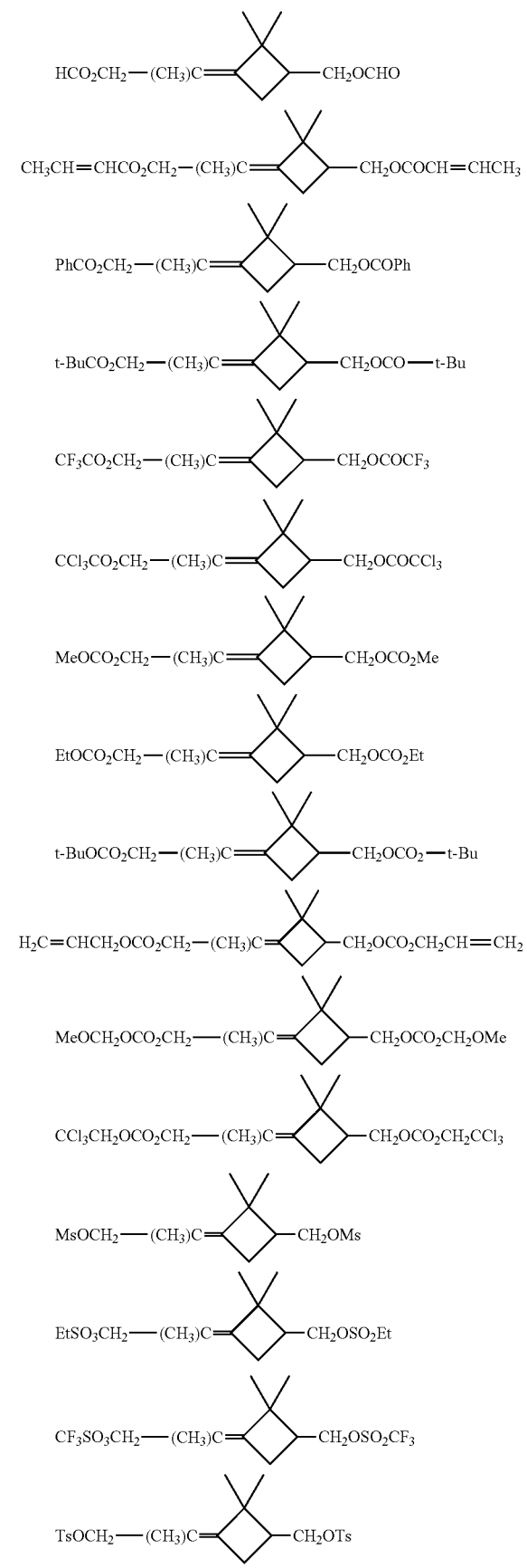

-continued
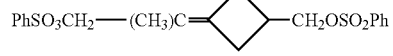
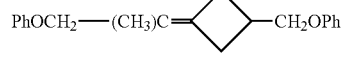
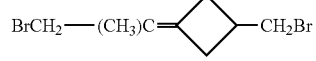
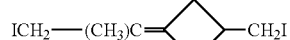
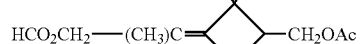
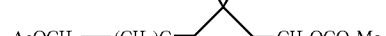
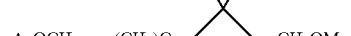
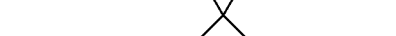
-continued
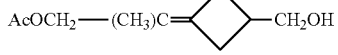
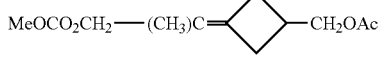
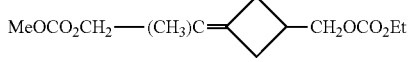
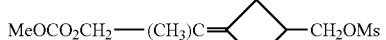
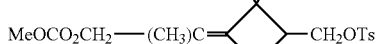
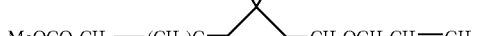

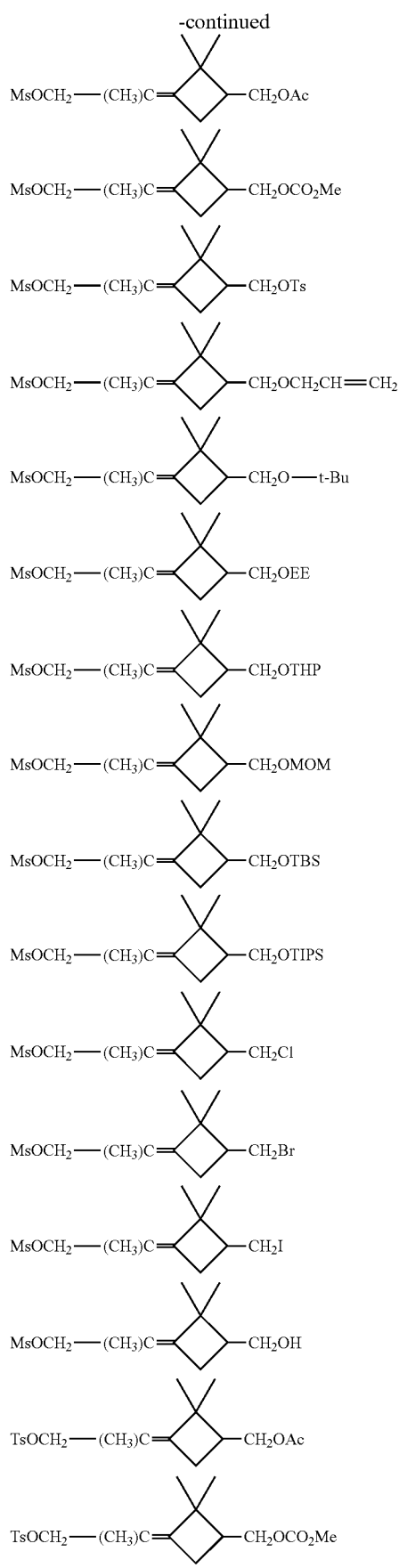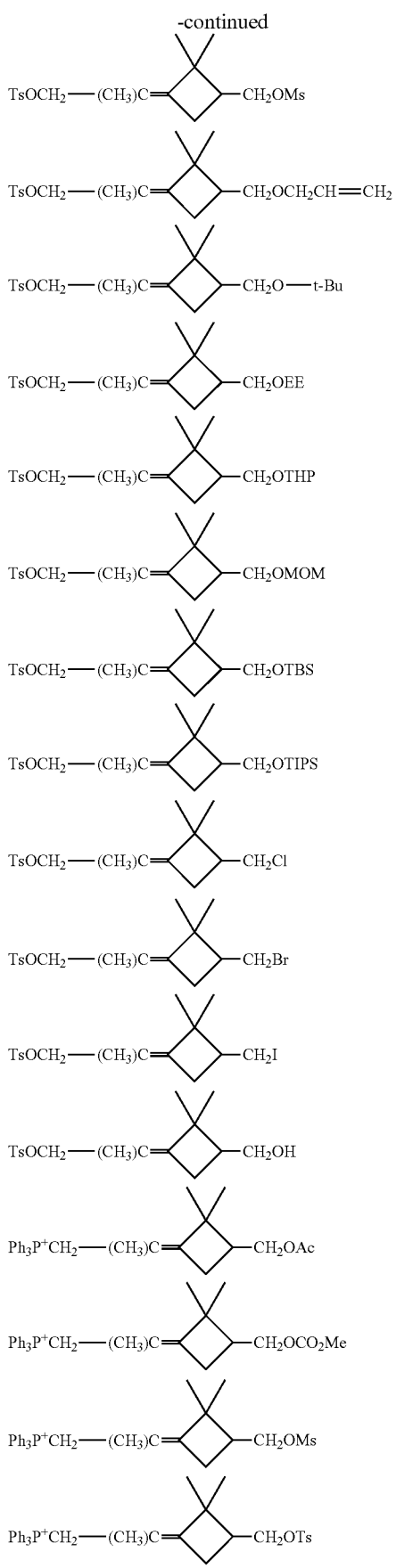

Ph₃P⁺CH₂—(CH₃)C=⟨⟩—CH₂OCH₂CH=CH₂

Ph₃P⁺CH₂—(CH₃)C=⟨⟩—CH₂O—t-Bu

Ph₃P⁺CH₂—(CH₃)C=⟨⟩—CH₂OEE

Ph₃P⁺CH₂—(CH₃)C=⟨⟩—CH₂OTHP

Ph₃P⁺CH₂—(CH₃)C=⟨⟩—CH₂OMOM

Ph₃P⁺CH₂—(CH₃)C=⟨⟩—CH₂OTBS

Ph₃P⁺CH₂—(CH₃)C=⟨⟩—CH₂OTIPS

Ph₃P⁺CH₂—(CH₃)C=⟨⟩—CH₂Cl

Ph₃P⁺CH₂—(CH₃)C=⟨⟩—CH₂Br

Ph₃P⁺CH₂—(CH₃)C=⟨⟩—CH₂I

Bu₃P⁺CH₂—(CH₃)C=⟨⟩—CH₂OAc

Bu₃P⁺CH₂—(CH₃)C=⟨⟩—CH₂OCO₂Me

Bu₃P⁺CH₂—(CH₃)C=⟨⟩—CH₂OMs

Bu₃P⁺CH₂—(CH₃)C=⟨⟩—CH₂OTs

Bu₃P⁺CH₂—(CH₃)C=⟨⟩—CH₂OCH₂CH=CH₂

Bu₃P⁺CH₂—(CH₃)C=⟨⟩—CH₂O—t-Bu

Bu₃P⁺CH₂—(CH₃)C=⟨⟩—CH₂OEE

Bu₃P⁺CH₂—(CH₃)C=⟨⟩—CH₂OTHP

Bu₃P⁺CH₂—(CH₃)C=⟨⟩—CH₂OMOM

Bu₃P⁺CH₂—(CH₃)C=⟨⟩—CH₂OTBS

Bu₃P⁺CH₂—(CH₃)C=⟨⟩—CH₂OTIPS

Bu₃P⁺CH₂—(CH₃)C=⟨⟩—CH₂Cl

Bu₃P⁺CH₂—(CH₃)C=⟨⟩—CH₂Br

Bu₃P⁺CH₂—(CH₃)C=⟨⟩—CH₂I

Bu₃P⁺CH₂—(CH₃)C=⟨⟩—CH₂OH

PhOCH₂—(CH₃)C=⟨⟩—CH₂OAc

PhOCH₂—(CH₃)C=⟨⟩—CH₂OCO₂Me

PhOCH₂—(CH₃)C=⟨⟩—CH₂OMs

PhOCH₂—(CH₃)C=⟨⟩—CH₂OTs

PhOCH₂—(CH₃)C=⟨⟩—CH₂OCH₂CH=CH₂

PhOCH₂—(CH₃)C=⟨⟩—CH₂O—t-Bu

PhOCH₂—(CH₃)C=⟨⟩—CH₂OEE

-continued

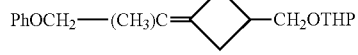
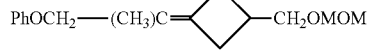
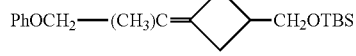
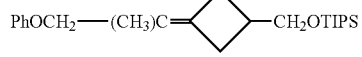
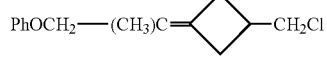
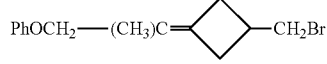
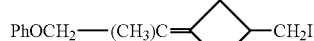
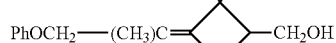
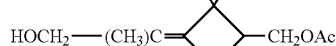

-continued

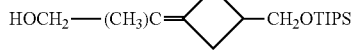
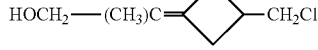
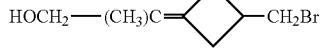
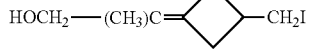

[II] Process for Preparing the Dimethylcyclobutane Compound (A)

Next, a process for preparing the dimethylcyclobutane compound (1A) according to the following two chemical reaction formulae will be explained hereinafter. The method comprises reacting a dimethylcyclobutanone compound of the following general formula (2) with a phosphonic ester compound of the following general formula (3), especially in an olefination reaction, preferably a Horner Wadsworth-Emmons reaction, to produce an unsaturated ester compound of the following general formula (4), having a dimethylcyclobutane ring; and

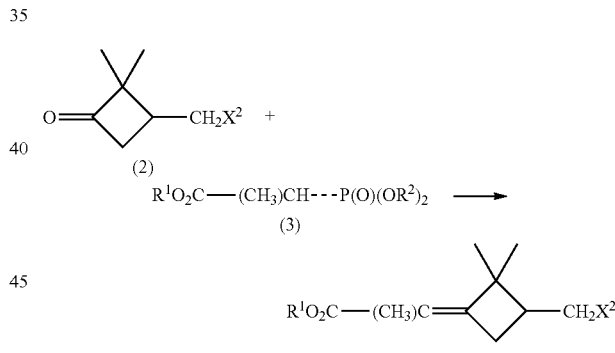

subjecting the unsaturated ester compound (4), having a dimethylcyclobutane ring, to a reduction reaction to produce the dimethylcyclobutane compound (1A).

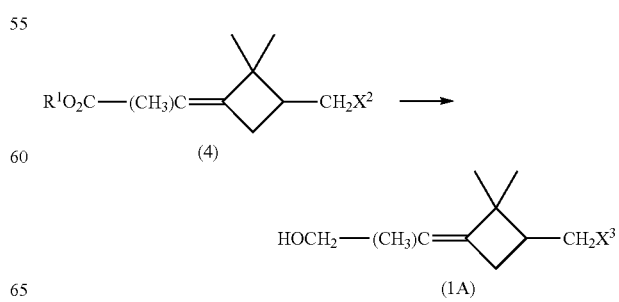

First, the aforesaid step of producing the unsaturated ester compound (4), having a dimethylcyclobutane ring, from the dimethylcyclobutanone compound (2) will be explained hereinafter.

$X^2$ in the dimethylcyclobutanone compound (2) is as defined above. The dimethylcyclobutanone compound of the following general formula (2B) is preferred among the dimethylcyclobutanone compound (2) in view of the stability of the compound and/or the ease of changing a specific group, $X^2$, to another group, $X^2$, among the options for $X^2$ defined above in a later process.

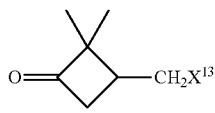

(2B)

$X^{13}$ in the dimethylcyclobutanone compound (2B) represents an acyloxy group having 3 to 10 carbon atoms including a carbon atom of a carbonyl group, an alkoxycarbonyloxy group having 2 to 10 carbon atoms including a carbon atom of a carbonyl group, an alkanesulfonyloxy group having 1 to 10 carbon atoms, an arenesulfonyloxy group having 6 to 20 carbon atoms, an alkoxy group having 2 to 12 carbon atoms with proviso that a benzyloxy group is excluded, an aryloxy group having 6 to 12 carbon atoms, or a silyloxy group having 3 to 20 carbon atoms.

Examples of the dimethylcyclobutanone compound (2) include a (S)-form of a dimethylcyclobutanone compound of the following general formula (2-1), a (R)-form of a dimethylcyclobutanone compound of the following general formula (2-2), and the racemates, and scalemic mixtures thereof.

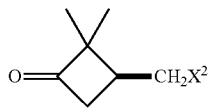

(2-1)

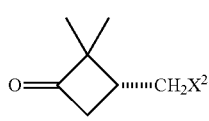

(2-2)

Examples of the dimethylcyclobutanone compound (2) include 3-hydroxymethyl-2,2-dimethylcyclobutanone, (2,2-dimethyl-3-oxocyclobutyl)methyl acetate, 3-benzyloxymethyl-2,2-dimethylcyclobutanone, 3-methoxymethoxymethyl-2,2-dimethylcyclobutanone, 2,2-dimethyl-3-(tetrahydropyran-2-yloxymethyl)cyclobutanone, 3-(1-ethoxyethoxy)methyl-2,2-dimethylcyclobutanone, 3-(1-allyloxyethoxy)methyl-2,2-dimethylcyclobutanone, and 3-allyloxymethyl-2,2-dimethylcyclobutanone.

3-Methoxymethoxymethyl-2,2-dimethylcyclobutanone, 2,2-dimethyl-3-(tetrahydropyran-2-yloxymethyl)cyclobutanone, 3-(1-ethoxyethoxy)methyl-2,2-dimethylcyclobutanone, 3-(1-allyloxyethoxy)methyl-2,2-dimethylcyclobutanone, and 3-allyloxymethyl-2,2-dimethylcyclobutanone, which are the dimethylcyclobutanone compound (2B), are preferred in view of the stability of the compound and/or the ease of changing a specific group, $X^2$, to another group, $X^2$, among the options for $X^2$ defined above in a later process.

The dimethylcyclobutanone compound (2) may be used alone or in combination thereof. The dimethylcyclobutanone compound (2) may be prepared, for example, as follow. Hereinafter, the explanations will be made each for the dimethylcyclobutanone compound (2A) corresponding to the compound except that a hydroxyl group is excluded from the definition of $X^2$ in the dimethylcyclobutanone (2), and 3-hydroxymethyl-2,2-dimethylcyclobutanone corresponding to the compound wherein $X^2$ in the dimethylcyclobutanone compound (2) is a hydroxyl group.

[III] the Dimethylcyclobutanone Compound (2A)

The dimethylcyclobutanone compound (2A) is as described above.

Process for preparing the dimethylcyclobutanone compound (2A)

Next, a process for preparing the dimethylcyclobutanone compound of the following general formula (2A), as shown in the following chemical reaction formula, will be explained hereinafter. The method comprises reacting an acid halide of the following general formula (7) and an allyl compound of the following general formula (8) with a base to produce the dimethylcyclobutanone compound (2A).

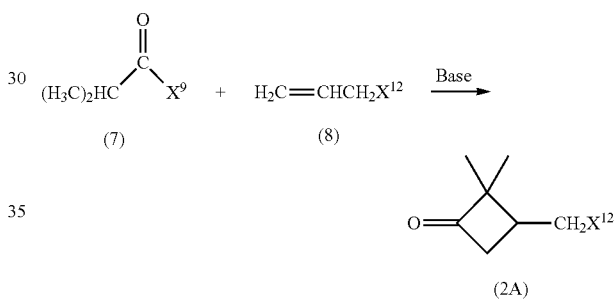

$X^9$ in the acid halide (7) represents a halogen atom. Examples of a halogen atom include a chlorine atom, a bromine atom, and an iodine atom.

$X^{12}$ in the allyl compound (8) is as defined above.

Examples of an acyloxy group having 1 to 10 carbon atoms including a carbon atom of a carbonyl group include linear aliphatic acyloxy groups such as a formyloxy group, an acetoxy (AcO) group, a propanoyloxy group, a butanoyloxy group, a pentanoyloxy group, a hexanoyloxy group, a heptanoyloxy group, an octanoyloxy group, a nonanoyloxy group, a decanoyloxy group, and an crotonyloxy group; branched aliphatic acyloxy groups such as a 2-methylpropanoyloxy group, a pivaloyloxy group, a 2-methylbutanoyloxy group, a 3-methyl-2-butenoyloxy group, and a 3-methyl-3-butenoyloxy group; halogenated acyloxy groups such as a trichloroacetoxy group and a trifluoroacetoxy group; and aromatic acyloxy groups such as a benzoyloxy group; and further may include a acyloxy group having an isomeric relation with the groups mentioned above.

A part of the hydrogen atoms of these acyloxy groups may be substituted with a methyl group, an ethyl group or a halogen atom. Particularly preferred examples of an acyloxy group having 1 to 10 carbon atoms including a carbon atom of a carbonyl group include a formyloxy group, an acetoxy group, a propanoyloxy group, a pivaloyloxy group, a 2-methylbutanoyloxy group, and benzoyloxy group in view of the availability.

Examples of an alkoxycarbonyloxy group having 2 to 10 carbon atoms including a carbon atom of a carbonyl group include linear saturated alkoxycarbonyloxy groups such as a methoxycarbonyloxy group, an ethoxycarbonyloxy group, an n-propoxycarbonyloxy group, an n-butoxycarbonyloxy group, an n-pentyloxycarbonyloxy group, an n-hexyloxycarbonyloxy group, an n-heptyloxycarbonyloxy group, an n-octyloxycarbonyloxy group, an n-nonyloxycarbonyloxy group, and a n-decyloxycarbonyloxy group; branched saturated alkoxycarbonyloxy groups such as an isopropoxycarbonyloxy group and a t-butoxycarbonyloxy group; linear unsaturated alkoxycarbonyloxy groups such as a 2-propenyloxycarbonyloxy group and a 2-propynyloxycarbonyloxy group; branched unsaturated alkoxycarbonyloxy groups such as a 2-methyl-2-propenyloxycarbonyloxy group; cyclic alkoxycarbonyloxy groups such as cyclopropyloxycarbonyloxy group, 2-methylcyclopropyloxycarbonyloxy group, cyclobutyloxycarbonyloxy group, and cyclopentyloxycarbonyloxy group; alkoxycarbonyloxy groups having an aromatic ring such as a benzyloxycarbonyloxy group and a paramethoxybenzyloxycarbonyloxy group; oxyalkoxycarbonyloxy groups such as a methoxymethoxycarbonyloxy group, a benzyloxymethoxycarbonyloxy group, and a paramethoxybenzyloxymethoxycarbonyloxy group; and halogenated alkoxycarbonyloxy groups such as a 2,2,2-trichloroethoxycarbonyloxy group; and further may include an alkoxycarbonyloxy group having an isomeric relation with the groups mentioned above.

A part of the hydrogen atoms of these alkoxycarbonyloxy groups may be substituted with a methyl group, an ethyl group or a halogen atom. Particularly preferred examples of an alkoxycarbonyloxy group having 2 to 10 carbon atoms including a carbon atom of a carbonyl group include a methoxycarbonyloxy group, an ethoxycarbonyloxy group, and an n-propoxycarbonyloxy group in view of the availability.

Examples of an alkanesulfonyloxy group having 1 to 10 carbon atoms include a methanesulfonyloxy (MsO) group, an ethanesulfonyloxy group, a 1-butanesulfonyloxy group, a 1-pentanesulfonyloxy group, a 1-hexanesulfonyloxy group, a 1-heptanesulfonyloxy group, a 1-octanesulfonyloxy group, a 1-nonanesulfonyloxy group, a 1-decanorsulfonyloxy group, an allylsulfonyloxy group, a 10-camphorsulfonyloxy group, a trifluoromethanesulfonyloxy group, and α-benzylsulfonyloxy group; and further may include an alkanesulfonyloxy group having an isomeric relation with the groups mentioned above.

A part of the hydrogen atoms of these alkanesulfonyloxy groups may be substituted with a methyl group, an ethyl group or a halogen atom. Particularly preferred examples of an alkanesulfonyloxy group having 1 to 10 carbon atoms include a methanesulfonyloxy group and an ethanesulfonyloxy group in view of the availability.

Examples of an arenesulfonyloxy group having 6 to 20 carbon atoms include a benzenesulfonyloxy group, a 4-chlorobenzenesulfonyloxy group, a 4-methoxybenzenesulfonyloxy group, a 2-nitrobenzenesulfonyloxy group, a 2,4,6-trimethylbenzenesulfonyloxy group, a paratoluenesulfonyloxy (TsO) group, a 1-naphthalenesulfonyloxy group, and 2-naphthalenesulfonyloxy group; and further may include an arenesulfonyloxy group having an isomeric relation with the groups mentioned above. A part of the hydrogen atoms of these arenesulfonyloxy groups may be substituted with a methyl group, an ethyl group or a halogen atom. Particularly preferred examples of an arenesulfonyloxy group having 6 to 20 carbon atoms include a benzenesulfonyloxy group and a paratoluenesulfonyloxy group in view of the availability.

Examples of an alkoxy group having 1 to 12 carbon atoms include linear saturated alkoxy groups such as a methoxy (MeO) group, an ethoxy (EtO) group, an n-propoxy (PrO) group, an n-butoxy (BuO) group, an n-pentyloxy (PenO) group, an n-hexyloxy (HexO) group, an n-heptyloxy group (HepO) group, an n-octyloxy (OctO) group, an n-nonyloxy (NonO) group, an n-decyloxy (DecO) group, an n-undecyloxy group, and an n-dodecyloxy group; branched saturated alkoxy groups such as isopropoxy group (i-PrO), isobutyloxy group (i-BuO), and t-butoxy (t-BuO) group; linear unsaturated alkoxy groups such as 2-propenyloxy group and 2-propynyloxy group; branched unsaturated alkoxy groups such as 2-methyl-2-propenyloxy group; cyclic alkoxy groups such as a cyclopropyloxy group, a 2-methylcyclopropyloxy group, a cyclobutyloxy group, a cyclopentyloxy group, and a cyclohexyloxy (c-HexO) group; alkoxy group having an aromatic ring such as a benzyloxy (BnO) group and a paramethoxybenzyloxy group; oxyalkoxy groups such as a methoxymethoxy (MOMO) group, a 2-methoxyethoxymethoxy group, a benzyloxymethoxy group, a paramethoxybenzyloxymethoxy group, a 1-ethoxyethoxy (EEO) group, a 1-allyloxyethoxy group, a tetrahydropyran-2-yloxy (THPO) group; and halogenated alkoxy groups such as a 2,2,2-trichloroethoxy group and a pentafluoroethoxy group; and further may include an alkoxy group having an isomeric relation with the groups mentioned above.

A part of the hydrogen atoms of these alkoxy groups may be substituted with a methyl group, an ethyl group or a halogen atom.

Particularly preferred examples of an alkoxy group having 1 to 12 carbon atoms include a methoxy group, an ethoxy group, a 2-propenyloxy group, a methoxymethoxy group, a 1-ethoxyethoxy group, a 1-allyloxyethoxy group, and a tetrahydropyran-2-yloxy group in view of ease of preparation.

Examples of an aryloxy group having 6 to 12 carbon atoms include a phenoxy (PhO) group, a 4-chlorophenoxy group, a 4-methoxyphenoxy group, a naphthoxy group, and a 4-biphenyloxy group; and further may include an aryloxy group having an isomeric relation with the groups mentioned above. A part of the hydrogen atoms of these alkoxy groups may be substituted with a methyl group, an ethyl group or a halogen atom. Particularly preferred examples of an aryloxy group having 6 to 12 carbon atoms include a phenoxy group and a naphthoxy group in view of the availability.

Examples of a silyloxy group having 3 to 20 carbon atoms include trialkylsilyloxy groups such as a trimethylsilyloxy (TMSO) group, a triethylsilyloxy (TESO) group, a triisopropylsilyloxy (TIPSO) group, and a t-butyldimethylsilyloxy (TBSO) group; and monoalkyldiarylsilyloxy groups such as a t-butyldiphenylsilyloxy (TBDPSO) group; and further may include a silyloxy group having an isomeric relation with the groups mentioned above. A part of the hydrogen atoms of these silyloxy groups may be substituted with a methyl group, an ethyl group or a halogen atom. Particularly preferred examples of a silyloxy group having 3 to 20 carbon atoms include a trimethylsilyloxy group, a triethylsilyloxy group, a triisopropylsilyloxy group, and a t-butyldimethylsilyloxy group in view of the availability.

Examples of a halogen atom include a chlorine atom, a bromine atom, and an iodine atom. Particularly preferred examples of a halogen atom include a chlorine atom and a bromine atom in view of the availability.

The allyl compound (8) may be used alone or in combination thereof. The allyl compound (8) may be commercially available one or may be synthesized in house.

An amount of the allyl compound (8) used is preferably from 0.2 to 100.0 mol, more preferably from 0.4 to 50.0 mol, and even more preferably from 0.6 to 25.0 mol, per mol of the acid halide (7).

Examples of a base used in the aforesaid reaction include metal hydrides such as sodium hydride, potassium hydride, and calcium hydride; and organic base compounds such as triethylamine, diisopropylethylamine, tributylamine, N,N-dimethylaniline, N,N-diethylaniline, pyridine, 4-dimethylaminopyridine, imidazole, quinoline, pyrrolidine, piperidine, collidine, lutidine, morpholine, 1,8-diazabicyclo[5.4.0]-7-undecene.

The base may be used alone or in combination thereof. The base may be commercially available one.

An amount of the base used is preferably from 0.7 to 5.0 mol, more preferably from 0.8 to 4.0 mol, and even more preferably from 0.9 to 3.0 mol, per mol of the acid halide (7).

The reaction above may be carried out without a solvent or in the presence of a solvent.

Examples of a solvent include ethers such as diethyl ether, dibutyl ether, tetrahydrofuran and 1,4-dioxane; hydrocarbons such as hexane, heptane, benzene, toluene, xylene and cumene; chlorinated solvents such as methylene chloride, chloroform, trichloroethylene; aprotic polar solvents such as N,N-dimethylformamide, 1,3-dimethyl-2-imidazolidinone, dimethyl sulfoxide, and hexamethylphosphoric triamide; nitriles such as acetonitrile and propionitrile; and esters such as ethyl acetate and n-butyl acetate.

The solvent may be used alone or in combination thereof. The solvent may be commercially available one.

An amount of the solvent used is preferably from 0 to 10,000 g per mol of the acid halide (7).

A reaction temperature is preferably from 40 to 200° C., more preferably from 50 to 190° C., and even more preferably from 60 to 180° C.

A reaction time in the aforesaid reaction may be set arbitrarily. It is desirable in view of the yield to monitor the reaction with gas chromatography (GC) or silica gel thin layer chromatography (TLC) to complete the reaction. A reaction time is usually about 0.5 to 72 hours.

The cyclobutanone compound (2A) is obtained by the above reaction, and then the specific group $X^1$ may be changed into another group, hydroxyl group, to use the resultant. For instance, in a case where $X^{12}$ is a 1-ethoxyethoxy group, $X^{12}$ may be changed to a hydroxyl group by an acid hydrolysis.

$R^1$ and $R^2$ in the phosphonic ester compound (3) represent, independently of each other, a monovalent hydrocarbon group having 1 to 10 carbon atoms. The carbon number of $R^1$ and $R^2$ is 1 to 10, preferably 1 to 5.

Examples of a monovalent hydrocarbon group include linear saturated hydrocarbon groups such as a methyl (Me) group, an ethyl (Et) group, an n-propyl (Pr) group, an n-butyl (Bu) group, an n-pentyl (Pen) group, an n-hexyl (Hex) group, an n-heptyl (Hep) group, an n-octyl (Oct) group, n-nonyl (Non) group, and n-decyl (Dec) group; branched saturated hydrocarbon groups such as an isopropyl (i-Pr) group, a sec-butyl group, an isobutyl (i-Bu) group, and a t-butyl (t-Bu) group; linear unsaturated hydrocarbon groups such as a 2-propenyl group and a 2-propynyl group; branched unsaturated hydrocarbon group such as a 2-methyl-2-propenyl group; cyclic hydrocarbon groups such as a cyclopropyl group, a 2-methylcyclopropyl group, a cyclobutyl group, a cyclopentyl group, and a cyclohexyl (c-Hex) group; aromatic hydrocarbon groups such as a phenyl (Ph) group, a 2-methylphenyl group, and a 4-methylphenyl group; and further may include a hydrocarbon group having an isomeric relation with the groups mentioned above.

A part of the hydrogen atoms of these hydrocarbon groups may be substituted with a methyl group, an ethyl group or a halogen atom. Particularly preferred examples of $R^1$ and $R^2$ include a methyl group, an ethyl group, an n-propyl group, an isopropyl group, an n-butyl group, a sec-butyl group, an isobutyl group and a t-butyl group, with more particularly preferred examples being a methyl group, an ethyl group, and an n-propyl group, in view of the availability of the phosphonic ester compound (3).

Particularly, an example of the phosphonic ester compound (3) includes triethyl 2-phosphonopropionate.

The phosphonic ester compound (3) may be used alone or in combination thereof. The phosphonic ester compound (3) may be commercially available one or may be synthesized in house. For instance, the phosphonic ester compound (3) may be synthesized by an Arbuzov reaction of a phosphite ester with a 2-bromopropionate.

An amount of the phosphonic ester compound (3) used is preferably from 0.7 to 5.0 mol, more preferably from 0.8 to 4.0 mol, and even more preferably from 0.9 to 3.0 mol, per mol of the dimethylcyclobutanone compound (2).

Examples of a base used in the aforesaid reaction include alkoxides such as sodium methoxide, sodium ethoxide, sodium t-butoxide, sodium t-amyloxide, lithium methoxide, lithium ethoxide, lithium t-butoxide, lithium t-amyloxide, potassium methoxide, potassium ethoxide, potassium t-butoxide, and potassium t-amyloxide; organometallic compounds such as methyllithium, ethyllithium, n-butyllithium, methylmagnesium chloride, and dimsyl sodium; metal amides such as sodium amide, lithium amide, lithium diisopropylamide, lithium hexamethyldisilazide, sodium hexamethyldisilazide, potassium hexamethyldisilazide, and lithium dicyclohexylamide; metal hydrides such as sodium hydride, potassium hydride, and calcium hydride; and organic base compounds such as triethylamine, diisopropylethylamine, tributylamine, N,N-dimethylaniline, N,N-diethylaniline, pyridine, 4-dimethylaminopyridine, imidazole, quinoline, pyrrolidine, piperidine, collidine, lutidine, morpholine, and 1,8-diazabicyclo[5.4.0]-7-undecene.

The base may be used alone or in combination thereof. The base may be commercially available one.

An amount of the base used is preferably from 0.7 to 5.0 mol, more preferably from 0.8 to 4.0 mol, and even more preferably from 0.9 to 3.0 mol, per mol of the phosphonic ester compound (3).

The aforesaid reaction may be carried out in the presence of a Lewis acid.

Examples of a Lewis acid include lithium halides such as lithium chloride, lithium bromide, and lithium iodide.

The Lewis acid may be used alone or in combination thereof. The Lewis acid may be commercially available one.

An amount of the Lewis acid used is preferably from 0.7 to 5.0 mol, more preferably from 0.8 to 4.0 mol, and even more preferably from 0.9 to 3.0 mol, per mol of the phosphonic ester compound (3).

Examples of a solvent include ethers such as diethyl ether, dibutyl ether, tetrahydrofuran, and 1,4-dioxane; hydrocarbons such as hexane, heptane, benzene, toluene, xylene, and cumene; chloride solvents such as methylene chloride, chloroform, and trichloroethylene; aprotic polar solvents such as N,N-dimethylformamide, 1,3-dimethyl-2-imidazolidinone, dimethyl sulfoxide, and hexamethylphosphoric triamide;

nitriles such as acetonitrile and propionitrile; esters such as ethyl acetate and n-butyl acetate; alcohols such as methanol, ethanol, and t-butyl alcohol; and water.

The solvent may be used alone or in combination thereof. The solvent may be commercially available one.

An amount of the solvent used is preferably from 10 to 10,000 g per mol of the dimethylcyclobutanone compound (2).

A reaction temperature is preferably from −78 to 180° C., more preferably from −60 to 160° C., and even more preferably from −40 to 140° C.

A reaction time in the aforesaid reaction may be set arbitrarily. It is desirable in view of the yield to monitor the reaction with gas chromatography (GC) or silica gel thin layer chromatography (TLC) to complete the reaction. A reaction time is usually about 0.5 to 24 hours.

Examples of an unsaturated ester compound (4), having a dimethylcyclobutane ring, include a (S,Z) form of an unsaturated ester compound having a dimethylcyclobutane ring of the following general formula (4-1), a (R,Z) form of an unsaturated ester compound having a dimethylcyclobutane ring of the following general formula (4-2), a (SE) form of an unsaturated ester compound having a dimethylcyclobutane ring of the following general formula (4-3), a (R,E) form of an unsaturated ester compound having a dimethylcyclobutane ring of the following general formula (4-4), and the racemates, diastereomeric mixtures and scalemic mixtures thereof.

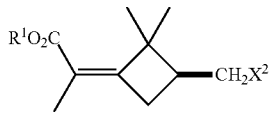
(4-1)

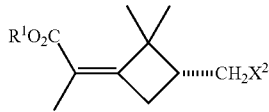
(4-2)

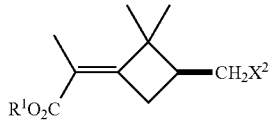
(4-3)

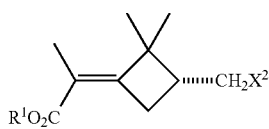
(4-4)

Examples of an unsaturated ester compound having a dimethylcyclobutane ring (4) include, especially, ethyl 2-(3-hydroxymethyl-2,2-dimethylcyclobutylidene)propanoate, ethyl 2-(3-acetoxymethyl-2,2-dimethylcyclobutylidene)propanoate, ethyl 2-(3-methoxymethoxymethyl-2,2-dimethylcyclobutylidene)propanoate, ethyl 2-[2,2-dimethyl-3-(tetrahydropyran-2-yloxymethyl)cyclobutylidene]propanoate, ethyl 2-(3-benzyloxymethyl-2,2-dimethylcyclobutylidene)propanoate, and ethyl 2-[3-(1-ethoxyethoxy)methyl-2,2-dimethylcyclobutylidene]propanoate.

Next, a process for preparing the dimethylcyclobutane compound (1A) from the unsaturated ester compound (4), having a dimethylcyclobutane ring, will be explained hereinafter.

$X^3$ in the dimethylcyclobutane compound (1A) represents a hydroxyl group, an alkanesulfonyloxy group having 1 to 10 carbon atoms, an arenesulfonyloxy group having 6 to 20 carbon atoms, an alkoxy group having 1 to 12 carbon atoms, an aryloxy group having 6 to 12 carbon atoms, and a silyloxy group having 3 to 20 carbon atoms or a halogen atom. Examples of these groups and the halogen atom are the groups mentioned above in a case where $X^1$ and $X^2$ are the alkanesulfonyloxy group having 1 to 10 carbon atoms, an arenesulfonyloxy group having 6 to 20 carbon atoms, an alkoxy group having 1 to 12 carbon atoms, an aryloxy group having 6 to 12 carbon atoms, and a silyloxy group having 3 to 20 carbon atoms; and a halogen atom, respectively.

In the reduction reaction above, in a case where $X^2$ in the unsaturated ester compound (4), having a dimethylcyclobutane ring, is maintained, $X^2$ is same as $X^3$ after the reaction. Meanwhile in a case where $X^2$ is not maintained, $X^2$ is different from $X^3$ after the reaction.

Examples of a reducing agent include hydrogen; borane; alkylborane compounds such as bis(3-methyl-2-butyl)borane; alkylsilane compounds such as triethylsilane; metal hydrides such as aluminum hydride; alkyl metal hydrides such as diisobutylaluminum hydride; complex hydrides such as sodium borohydride, lithium borohydride, potassium borohydride, calcium borohydride, sodium trimethoxyborohydride, lithium triethylborohydride, sodium aluminum hydride, lithium aluminum hydride, lithium trimethoxyaluminum hydride, lithium diethoxyaluminum hydride, lithium tri-tert-butoxyaluminum hydride, sodium bis(2-methoxyethoxy)aluminum hydride; and alkoxy or alkyl derivatives thereof.

The reducing agent may be used alone or in combination thereof. The reducing agent may be commercially available one.

An amount of the reducing agent used is preferably from 3.5 to 100.0 mol, more preferably from 3.6 to 20.0 mol, and even more preferably from 3.7 to 15.0 mol, in terms of hydride, per mol of the unsaturated ester compound (4), having a dimethylcyclobutane ring.

Examples of a solvent used in the reduction reaction include ethers such as diethyl ether, dibutyl ether, tetrahydrofuran, and 1,4-dioxane; hydrocarbons such as hexane, heptane, benzene, toluene, xylene, and cumene; chloride solvents such as methylene chloride, chloroform, and trichloroethylene; aprotic polar solvents such as N,N-dimethylformamide, 1,3-dimethyl-2-imidazolidinone, dimethyl sulfoxide, and hexamethylphosphoric triamide; nitriles such as acetonitrile and propionitrile; esters such as ethyl acetate and n-butyl acetate; alcohols such as methanol, ethanol, and t-butyl alcohol; and water.

The solvent may be used alone or in combination thereof. The solvent may be commercially available one.

An amount of the solvent used is preferably from 10 to 20,000 g per mol of the unsaturated ester compound (4), having a dimethylcyclobutane ring.

A reaction temperature is preferably from −78 to 180° C., more preferably from −78 to 160° C., and even more preferably from −78 to 140° C.

A reaction time in the aforesaid reaction may be set arbitrarily. It is desirable in view of the yield to monitor the reaction with gas chromatography (GC) or silica gel thin layer chromatography (TLC) to complete the reaction. A reaction time is usually about 0.5 to 24 hours.

Examples of a dimethylcyclobutane compound (1A) may be those mentioned above in the dimethylcyclobutane compound (1).

[IV] Process for Preparing the Dimethylcyclobutane Compound (1B)

Next, a process for preparing the dimethylcyclobutane compound (1B) according to the following two chemical reaction formulae will be explained hereinafter. The method comprises changing a hydroxyl group in the dimethylcyclobutane compound (1A), and optionally $X^3$, to produce the dimethylcyclobutane compound (1B)

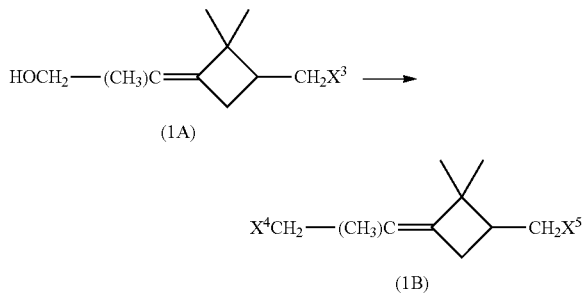

$X^4$ represents an acyloxy group having 1 to 10 carbon atoms including a carbon atom of a carbonyl group, an alkoxycarbonyloxy group having 2 to 10 carbon atoms including a carbon atom of a carbonyl group, an alkanesulfonyloxy group having 1 to 10 carbon atoms, an arenesulfonyloxy group having 6 to 20 carbon atoms, an alkoxy group having 1 to 12 carbon atoms, an aryloxy group having 6 to 12 carbon atoms, a silyloxy group having 3 to 20 carbon atoms, a trialkylphosphonio group having 3 to 30 carbon atoms, a triarylphosphonio group having 12 to 30 carbon atoms or a halogen atom. Examples of these groups and the halogen atom are the groups mentioned above in a case where $X^1$ and $X^2$ are the acyloxy group having 1 to 10 carbon atoms including a carbon atom of a carbonyl group, an alkoxycarbonyloxy group having 2 to 10 carbon atoms including a carbon atom of a carbonyl group, an alkanesulfonyloxy group having 1 to 10 carbon atoms, an arenesulfonyloxy group having 6 to 20 carbon atoms, an alkoxy group having 1 to 12 carbon atoms, an aryloxy group having 6 to 12 carbon atoms, a silyloxy group having 3 to 20 carbon atoms, a trialkylphosphonio group having 3 to 30 carbon atoms, and a triarylphosphonio group having 12 to 30 carbon atoms; and a halogen atom, respectively.

$X^5$ is same as $X^2$ above.

In the changing reaction above, in a case where $X^3$ in the dimethylcyclobutane compound (1A) is maintained in the reduction reaction, $X^3$ is same as $X^5$ after the reaction. Meanwhile in a case where $X^3$ is not maintained, $X^3$ is different from $X^5$ after the reaction.

The changing reaction above may be carried out by a known method.

The dimethylcyclobutane compound of the following general formula (1D), having an acyloxy group and an alkoxy group, may be produced by subjecting the dimethylcyclobutane compound of the following general formula (1C), having a hydroxyl group and an alkoxy group, to an acylation reaction with an acylating agent, as shown in the following chemical reaction formula (see Examples 20 and 21 below).

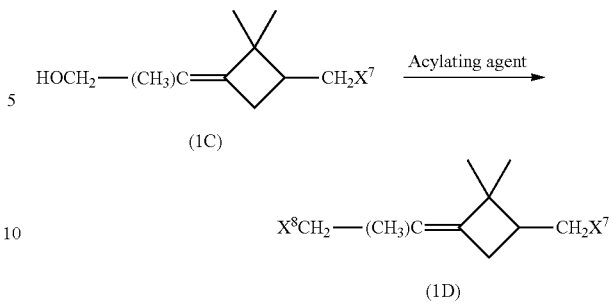

$X^7$ in the dimethylcyclobutane compound (1C), having a hydroxyl group and an alkoxy group, and the dimethylcyclobutane compound (1D), having an acyloxy group and an alkoxy group, represents an alkoxy group having 1 to 12 carbon atoms. Examples of an alkoxy group having 1 to 12 carbon atoms are the groups mentioned above in a case where $X^1$ and $X^2$ are the alkoxy group having 1 to 12 carbon atoms.

$X^8$ represents an acyloxy group having 1 to 10 carbon atoms including a carbon atom of a carbonyl group. Examples of an acyloxy group having 1 to 10 carbon atoms including a carbon atom of a carbonyl group are the groups mentioned above in a case where $X^1$ and $X^2$ am the acyloxy group having 1 to 10 carbon atoms including a carbon atom of a carbonyl group.

Examples of an acylating agent include acid anhydrides such as acetic anhydride, propionic anhydride, butanoic anhydride, and 2-methylbutanoic acid; and acid chlorides such as acetyl chloride, propionyl chloride, butanoyl chloride, and 2-methylbutanoyl chloride.

The acylating agent may be used alone or in combination thereof. The acylating agent may be commercially available one.

An amount of the acylating agent used is preferably from 0.7 to 100 mol, more preferably from 0.8 to 50 mol, and even more preferably from 0.9 to 20 mol, per mol of a hydroxyl group of the dimethylcyclobutane compound (1C), having a hydroxyl group and an alkoxy group.

Examples of a base used in the acylation reaction include alkoxides such as sodium methoxide, sodium ethoxide, sodium t-butoxide, sodium t-amyloxide, lithium methoxide, lithium ethoxide, lithium t-butoxide, lithium t-amyloxide, potassium methoxide, potassium ethoxide, potassium t-butoxide, and potassium t-amyloxide; organometallic compounds such as methyllithium, ethyllithium, n-butyllithium, methylmagnesium chloride, and dimsyl sodium; metal amides such as sodium amide, lithium amide, lithium diisopropylamide, lithium hexamethyldisilazide, sodium hexamethyldisilazide, potassium hexamethyldisilazide, and lithium dicyclohexylamide; metal hydrides such as sodium hydride, potassium hydride, and calcium hydride; and organic base compounds such as triethylamine, diisopropylethylamine, tributylamine, N,N-dimethylaniline, N,N-diethylaniline, pyridine, 4-dimethylaminopyridine, imidazole, quinoline, pyrrolidine, piperidine, collidine, lutidine, morpholine, and 1,8-diazabicyclo[5.4.0]-7-undecene.

The base may be used alone or in combination thereof. The base may be commercially available one.

An amount of the base used is preferably from 0.8 to 110 mol, more preferably from 0.9 to 60 mol, and even more preferably from 1 to 30 mol, per mol of a hydroxyl group of the dimethylcyclobutane compound (1C), having a hydroxyl group and an alkoxy group.

Examples of a solvent used in the acylation reaction include ethers such as diethyl ether, dibutyl ether, tetrahydrofuran, and 1,4-dioxane; hydrocarbons such as hexane, heptane, benzene, toluene, xylene, and cumene; chloride solvents such as methylene chloride, chloroform, and trichloroethylene; aprotic polar solvents such as N,N-dimethylformamide, 1,3-dimethyl-2-imidazolidinone, dimethyl sulfoxide, and hexamethylphosphoric triamide; nitriles such as acetonitrile and propionitrile; esters such as ethyl acetate and n-butyl acetate; alcohols such as methanol, ethanol, and t-butyl alcohol; and water.

The solvent may be used alone or in combination thereof. The solvent may be commercially available one.

An amount of the solvent used is preferably from 10 to 10,000 g per mol of the dimethylcyclobutane compound (1C), having a hydroxyl group and an alkoxy group.

A reaction temperature in the acylation reaction is preferably from −78 to 180° C., more preferably from −60 to 160° C., and even more preferably from −40 to 140° C.

A reaction time in the aforesaid reaction may be set arbitrarily. It is desirable in view of the yield to monitor the reaction with gas chromatography (GC) or silica gel thin layer chromatography (TLC) to complete the reaction. A reaction time is usually about 0.5 to 24 hours.

The dimethylcyclobutane compound of the following general formula (F), having two acyloxy groups, may be produced by subjecting the dimethylcyclobutane compound of the following general formula (1E), having two hydroxyl groups, to an acylation reaction with an acylating agent, as shown in the following chemical reaction formula (see Examples 24 and 25 below).

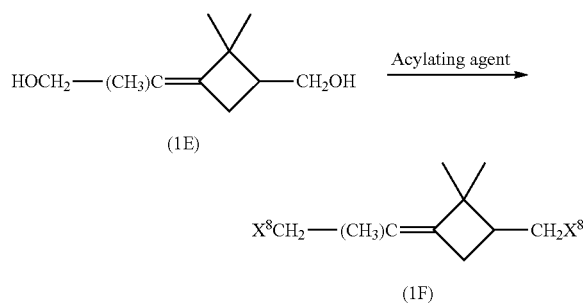

$X^8$ represents an acyloxy group having 1 to 10 carbon atoms including a carbon atom of a carbonyl group. Examples of an acyloxy group having 1 to 10 carbon atoms including a carbon atom of a carbonyl group are the groups mentioned above in a case where $X^1$ and $X^2$ are the acyloxy group having 1 to 10 carbon atoms including a carbon atom of a carbonyl group.

The acylation reaction may be carried out in the manner similar with the aforesaid step of obtaining the dimethylcyclobutane compound (1D), having an acyloxy group and an acyl group.

The dimethylcyclobutane compound of the following general formula (G), having a halogen atom and an alkoxy group, may be produced by subjecting the dimethylcyclobutane compound (1C), having a hydroxyl group and an alkoxy group, to a halogenation reaction with a halogen source and a phosphine compound, or by subjecting the dimethylcyclobutane compound (1C), having a hydroxyl group and an alkoxy group, to a halogenation reaction with a sulfonyl halide compound, as shown in the following chemical reaction formula (see Examples 17 and 18 below).

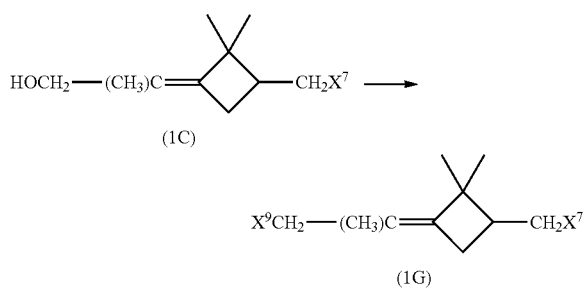

$X^7$ in the dimethylcyclobutane compound (1G), having a halogen atom and an alkoxy group, is as defined above.

$X^9$ represents a halogen atom. Examples of a halogen atom include a chlorine atom, a bromine atom, and an iodine atom. First, the halogenation reaction with a halogen source and a phosphine compound will be described hereinafter (see Example 18 below).

Examples of a halogen source include carbon tetrahalide compounds such as carbon tetrachloride and carbon tetrabromide; and halogen molecules such as bromine and iodine.

The halogen source may be used alone or in combination thereof. The halogen source may be commercially available one.

An amount of the halogen source used is preferably from 0.7 to 1,000 mol, more preferably from 0.8 to 500 mol, and even more preferably from 0.9 to 200 mol, per mol of a hydroxyl group of the dimethylcyclobutane compound (1C), having a hydroxyl group and an alkoxy group.

Examples of a phosphine compound include triarylphosphine compounds such as triphenylphosphine; and trialkylphosphine compounds such as trioctylphosphine.

An amount of the phosphine compound used is preferably from 1.4 to 20.0 mol, more preferably from 1.4 to 16 mol, and even more preferably from 1.5 to 14 mol, per mol of the dimethylcyclobutane compound (1C), having a hydroxyl group and an alkoxy group.

The phosphine compound may be used alone or in combination thereof. The solvent may be commercially available one.

The halogenation reaction may be carried out in the presence of a base.

Examples of a base include organic base compounds such as triethylamine, diisopropylethylamine, tributylamine, N,N-dimethylaniline, N,N-diethylaniline, pyridine, 4-dimethylaminopyridine, imidazole, quinoline, pyrrolidine, piperidine, collidine, lutidine, morpholine, and 1,8-diazabicyclo[5.4.0]-7-undecene.

The base may be used alone or in combination thereof. The base may be commercially available one.

An amount of the base used is preferably from 0 to 1000 mol, more preferably from 0 to 500 mol, and even more preferably from 0 to 200 mol, per mol of a hydroxyl group of the dimethylcyclobutane compound (1C), having a hydroxyl group and an alkoxy group.

Examples of a solvent used in the halogenation reaction include ethers such as diethyl ether, dibutyl ether, tetrahydrofuran, 1,4-dioxane; hydrocarbons such as hexane, heptane, benzene, toluene, xylene, and cumene; chloride solvents such as methylene chloride, chloroform, carbon tetrachloride, and trichloroethylene; aprotic polar solvents such as N,N-dimethylformamide, 1,3-dimethyl-2-imidazolidinone, dimethyl sulfoxide, and hexamethylphosphoric triamide; nitriles such as acetonitrile and propionitrile; and esters such as ethyl acetate and n-butyl acetate.

The solvent may be used alone or in combination thereof. The solvent may be commercially available one.

An amount of the solvent used is preferably from 0 to 20,000 g per mol of the dimethylcyclobutane compound (1C), having a hydroxyl group and an alkoxy group.

A reaction temperature in the halogenation reaction is preferably from −78 to 180° C., more preferably from −60 to 160° C., and even more preferably from −40 to 140° C.

A reaction time in the halogenation reaction may be set arbitrarily. It is desirable in view of the yield to monitor the reaction with gas chromatography (GC) or silica gel thin layer chromatography (TLC) to complete the reaction. A reaction time is usually about 0.5 to 24 hours.

Next, the halogenation reaction with a sulfonyl halide compound will be described hereinafter (see Example 17 below).

Examples of a sulfonyl halide compound include arenesulfonyl halide compounds such as a paratoluenesulfonyl chloride and a benzenesulfonyl chloride; alkanesulfonyl halide compounds such as a methanesulfonyl chloride; and thionyl chloride.

The sulfonyl halide compound may be used alone or in combination thereof. The sulfonyl halide compound may be commercially available one.

An amount of the sulfonyl halide compound used is preferably from 0.7 to 1,000 mol, more preferably from 0.8 to 500 mol, and even more preferably from 0.9 to 200 mol, per mol of a hydroxyl group of the dimethylcyclobutane compound (1C), having a hydroxyl group and an alkoxy group.

The halogenation reaction may be carried out in the presence of a base.

Examples of a base include organic base compounds such as triethylamine, diisopropylethylamine, tributylamine, N,N-dimethylaniline, N,N-diethylaniline, pyridine, 4-dimethylaminopyridine, imidazole, quinoline, pyrrolidine, piperidine, collidine, lutidine, morpholine, and 1,8-diazabicyclo[5.4.0]-7-undecene.

The base may be used alone or in combination thereof. The base may be commercially available one.

An amount of the base used is preferably from 0 to 1000 mol, more preferably from 0 to 500 mol, and even more preferably from 0 to 200 mol, per mol of a hydroxyl group of the dimethylcyclobutane compound (1C), having a hydroxyl group and an alkoxy group.

Examples of a solvent used in the halogenation reaction include ethers such as diethyl ether, dibutyl ether, tetrahydrofuran, 1,4-dioxane; hydrocarbons such as hexane, heptane, benzene, toluene, xylene, and cumene; chloride solvents such as methylene chloride, chloroform, carbon tetrachloride, and trichloroethylene; aprotic polar solvents such as N,N-dimethylformamide, 1,3-dimethyl-2-imidazolidinone, dimethyl sulfoxide, and hexamethylphosphoric triamide; nitriles such as acetonitrile and propionitrile; and esters such as ethyl acetate and n-butyl acetate.

The solvent may be used alone or in combination thereof. The solvent may be commercially available one.

An amount of the solvent used is preferably from 10 to 10,000 g per mol of the dimethylcyclobutane compound (1C), having a hydroxyl group and an alkoxy group.

A reaction temperature in the halogenation reaction is preferably from −78 to 180° C., more preferably from −60 to 160° C., and even more preferably from −40 to 140° C.

A reaction time in the halogenation reaction may be set arbitrarily. It is desirable in view of the yield to monitor the reaction with gas chromatography (GC) or silica gel thin layer chromatography (TLC) to complete the reaction. A reaction time is usually about 0.5 to 24 hours.

The dimethylcyclobutane compound of the following general formula (H), having two halogen atoms, may be produced by subjecting the dimethylcyclobutane compound (1E), having two hydroxyl groups, to a halogenation reaction with a halogen source and a phosphine compound, as shown in the following chemical reaction formula (see Example 26 below).

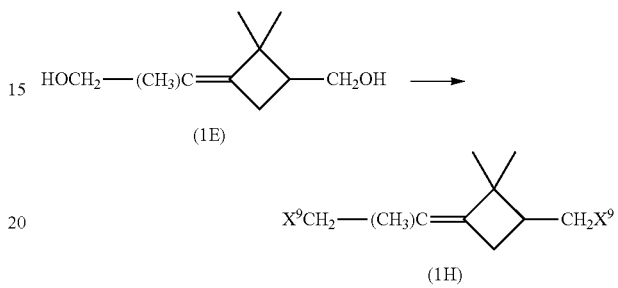

$X^9$ is as defined above.

The halogenation reaction may be carried out in the manner similar with the aforesaid step of obtaining the dimethylcyclobutane compound (1G), having a halogen atom and an alkoxy group.

The dimethylcyclobutane compound of the following general formula (1I), having a phosphonio group and a hydroxyl group, may be produced by subjecting dimethylcyclobutane compound (1E), having two hydroxyl groups, to a phosphonation reaction with a phosphine hydrohalide salt, as shown in the following chemical reaction formula (see Example 27 below).

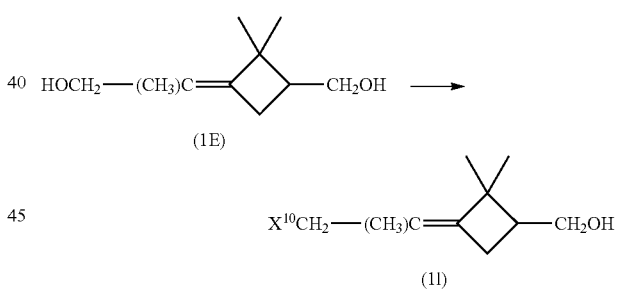

$X^{10}$ represents a trialkylphosphonio group having 3 to 30 carbon atoms or a triarylphosphonio group having 12 to 30 carbon atoms. Examples of a trialkyphosphonio group having 3 to 30 carbon atoms are the groups mentioned above in a case where $X^1$ and $X^2$ are the trialkylphosphonio group having 3 to 30 carbon atoms. $X^{10}$ is derived from the phosphine hydrohalide used in the phosphonation reaction.

Examples of a phosphine hydrohalide include triphenylphosphine hydrochloride, triphenylphosphine hydrobromide, and triphenylphosphine hydroiodide.

An amount of the phosphine hydrohalide used is preferably from 0.7 to 10.0 mol, more preferably from 0.8 to 8.0 mol, and even more preferably from 0.9 to 6.0 mol, per mol of the dimethylcyclobutane compound (1E), having two hydroxyl groups.

The phosphine hydrohalide may be used alone or in combination thereof. The phosphine hydrohalide may be commercially available one.

Examples of a solvent used in the phosphonation reaction include ethers such as diethyl ether, dibutyl ether, tetrahydrofuran, and 1,4-dioxane; hydrocarbons such as hexane, heptane, benzene, toluene, xylene, and cumene; chloride solvents such as methylene chloride, chloroform, and trichloroethylene; aprotic polar solvents such as N,N-dimethylformamide, 1,3-dimethyl-2-imidazolidinone, dimethyl sulfoxide, and hexamethylphosphoric triamide; nitriles such as acetonitrile and propionitrile; esters such as ethyl acetate and n-butyl acetate; alcohols such as methanol, ethanol, and t-butyl alcohol; and water.

The solvent may be used alone or in combination thereof. The solvent may be commercially available one.

An amount of the solvent used is preferably from 10 to 10,000 g per mol of the dimethylcyclobutane compound (1E), having two hydroxyl groups.

A reaction temperature in the phosphonation reaction is preferably from −78 to 180° C., more preferably from −60 to 160° C., and even more preferably from −40 to 140° C.

A reaction time in the phosphonation reaction may be set arbitrarily. It is desirable in view of the yield to monitor the reaction with gas chromatography (GC) or silica gel thin layer chromatography (TLC) to complete the reaction. A reaction time is usually about 0.5 to 24 hours.

The substituents (i.e. $X^4$ and $X^5$) in the dimethylcyclobutane compound (1B) may be changed to another group in multiple steps.

The dimethylcyclobutane compound of the following formula (1E), having two hydroxyl groups, may be produced by subjecting the dimethylcyclobutane compound (1C), having a hydroxyl group and an alkoxy group, to a deprotection reaction with an acid, as shown in the following chemical reaction formula (see Example 22 below). Then, a hydroxyl group of the dimethylcyclobutane compound (1E), having two hydroxyl groups, may be subjected to a conversion reaction such as acylation, halogenation, and phosphonation.

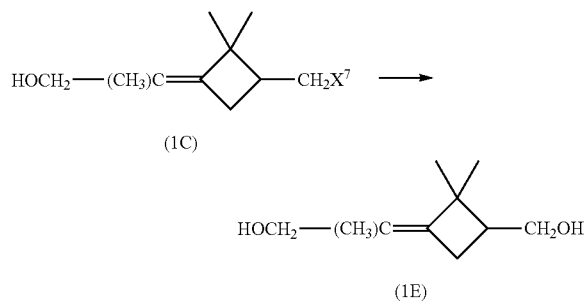

Examples of an acid include inorganic acids such as hydrochloric acid, hydrobromic acid, hydroiodic acid, sulfuric acid, nitric acid, phosphoric acid, or a their salts; organic acids such as formic acid, acetic acid, propionic acid, oxalic acid, trifluoroacetic acid, methanesulfonic acid, benzenesulfonic acid, p-toluenesulfonic acid, and naphthalenesulfonic acid, or salts thereof; Lewis acids such as lithium tetrafluoroborate, boron trifluoride, boron trichloride, boron tribromide, aluminum trichloride, zinc chloride, zinc bromide, zinc iodide, tin tetrachloride, tin tetrabromide, tin dichloride, titanium tetrachloride, titanium tetrabromide, and trimethyliodosilane; oxides such as alumina, silica gel, and titania; and minerals such as montmorillonite.

The acid may be used alone or in combination thereof. The acid may be commercially available one.

An amount of the acid used is preferably from 0.00001 to 10,000 mol, more preferably from 0.0001 to 1,000 mol, and even more preferably from 0.001 to 100, per mol of the dimethylcyclobutane compound (1C), having a hydroxyl group and an alkoxy group.

Examples of a solvent used in the deprotection reaction include ethers such as diethyl ether, dibutyl ether, tetrahydrofuran, and 1,4-dioxane; hydrocarbons such as hexane, heptane, benzene, toluene, xylene, and cumene; chloride solvents such as methylene chloride, chloroform, and trichloroethylene; aprotic polar solvents such as N,N-dimethylformamide, 1,3-dimethyl-2-imidazolidinone, dimethyl sulfoxide, and hexamethylphosphoric triamide; nitriles such as acetonitrile and propionitrile; esters such as ethyl acetate and n-butyl acetate; alcohols such as methanol, ethanol, and t-butyl alcohol; and water.

The solvent may be used alone or in combination thereof. The solvent may be commercially available one.

An amount of the solvent used is preferably from 10 to 10,000 g per mol of the dimethylcyclobutane compound (1C), having a hydroxyl group and an alkoxy group.

A reaction temperature in the deprotection reaction is preferably from −78 to 180° C., more preferably from −60 to 160° C., and even more preferably from −40 to 140° C.

A reaction time in the deprotection reaction may be set arbitrarily. It is desirable in view of the yield to monitor the reaction with gas chromatography (GC) or silica gel thin layer chromatography (TLC) to complete the reaction. A reaction time is usually about 0.5 to 24 hours.

The dimethylcyclobutane compound of the following formula (1J), having a halogen atom and an acyloxy group, may be produced by halogenating the dimethylcyclobutane compound (F), having two acyloxy groups, with a hydrogen halide compound, as shown in the following chemical reaction formula (see Example 28 below).

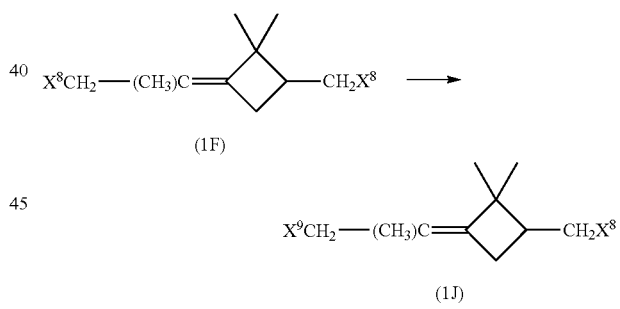

$X^8$ and $X^9$ are as defined above.

Examples of a hydrogen halide compound include hydrogen chloride, hydrogen bromide, and hydrogen iodide.

The hydrogen halide compound may be used alone or in combination thereof. The hydrogen halide may be commercially available one.

An amount of the hydrogen halide compound used is preferably from 0.7 to 10 mol, more preferably from 0.8 to 8 mol, and even more preferably from 0.9 to 6 mol, per mol of the dimethylcyclobutane compound (1F), having two acyloxy groups.

Examples of a solvent used in the halogenation reaction include ethers such as diethyl ether, dibutyl ether, tetrahydrofuran, and 1,4-dioxane; hydrocarbons such as hexane, heptane, benzene, toluene, xylene, and cumene; chloride solvents such as methylene chloride, chloroform, tetrachloromethane, and trichloroethylene; aprotic polar solvents such as N,N-dimethylformamide, 1,3-dimethyl-2-imidazolidinone, dimethyl sulfoxide, and hexamethylphosphoric triamide; nitriles such as acetonitrile and propionitrile; esters such as ethyl acetate and n-butyl acetate; carboxylic acids such as formic acid, acetic acid, and propionic acid; and water.

The solvent may be used alone or in combination thereof. The solvent may be commercially available one.

An amount of the solvent used is preferably from 10 to 10,000 g per mol of the dimethylcyclobutane compound (1F), having two acyloxy groups.

A reaction temperature in the halogenation reaction is preferably from −78 to 180° C., more preferably from −60 to 160° C., and even more preferably from −40 to 140° C.

A reaction time in the halogenation reaction may be set arbitrarily. It is desirable in view of the yield to monitor the reaction with gas chromatography (GC) or silica gel thin layer chromatography (TLC) to complete the reaction. A reaction time is usually about 0.5 to 24 hours.

The dimethylcyclobutane compound of the following formula (1K), having a phosphonio group and an alkoxy group, may be produced by subjecting the dimethylcyclobutane compound (1G), having a halogen atom and an alkoxy group, to a phosphonation reaction with a phosphine compound, as shown in the following chemical reaction formula (see Example 19 below).

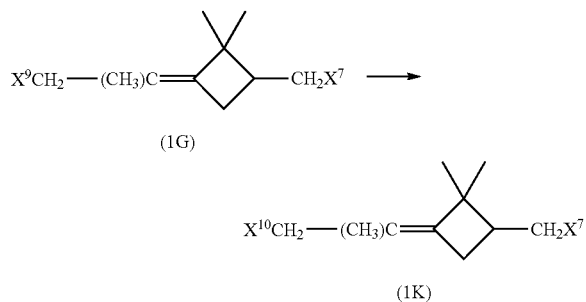

$X^7$ and $X^{10}$ are as defined above.

Examples of a phosphine compound include triarylphosphine compounds such as a triphenylphosphine; and trialkylphosphine compounds such as trioctylphosphine.

An amount of the phosphine compound used is preferably from 0.7 to 10.0 mol, more preferably from 0.8 to 8.0 mol, and even more preferably from 0.9 to 6.0 mol, per mol of the dimethylcyclobutane compound (1G), having a halogen atom and an alkoxy group.

Examples of a solvent used in the phosphonation reaction include others such as diethyl ether, dibutyl ether, tetrahydrofuran, and 1,4-dioxane; hydrocarbons such as hexane, heptane, benzene, toluene, xylene, and cumene; chloride solvents such as methylene chloride, chloroform, tetrachloromethane, and trichloroethylene; aprotic polar solvents such as N,N-dimethylformamide, 1,3-dimethyl-2-imidazolidinone, dimethyl sulfoxide, and hexamethylphosphoric triamide; nitriles such as acetonitrile and propionitrile; esters such as ethyl acetate and n-butyl acetate; alcohols such as methanol, ethanol, and t-butyl alcohol; and water.

The solvent may be used alone or in combination thereof. The solvent may be commercially available one.

An amount of the solvent used is preferably from 10 to 10,000 g per mol of the dimethylcyclobutane compound (1G), having a halogen atom and an alkoxy group.

A reaction temperature in the phosphonation reaction is preferably from −78 to 180° C., more preferably from −60 to 160° C., and even more preferably from −40 to 140° C.

A reaction time in the phosphonation reaction may be set arbitrarily. It is desirable in view of the yield to monitor the reaction with gas chromatography (GC) or silica gel thin layer chromatography (TLC) to complete the reaction. A reaction time 16 is usually about 0.5 to 24 hours.

Examples of the dimethylcyclobutane compound (1B) include the compounds mentioned for the dimethylcyclobutane compound (1), with proviso that the dimethylcyclobutane compound (1) with $X^1$ being a hydroxyl group is precluded.

The dimethylcyclobutane compound (1) wherein $X^1$ is a hydroxyl group and $X^2$ is an acyloxy group or an alkoxycarbonyloxy group may be prepared by hydrolyzing the dimethylcyclobutane compound (1) whose $X^1$ and $X^2$ are an acyloxy group or an alkoxycarbonyloxy group so as to change $X^1$ to a hydroxyl group.

[V] Process for Preparing the Isopropenyl Dimethylcyclobutane Compound (5) and/or the Isopropylidene Dimethylcyclobutane Compound (6)

Next, a process for preparing the isopropenyl dimethylcyclobutane compound of the following general formula (5) and/or the isopropylidene dimethylcyclobutane compound of the following general formula (6), as shown in the following chemical reaction formula, will be explained hereinafter. The method comprises subjecting the dimethylcyclobutane compound (1) to a reduction reaction to produce the isopropenyl dimethylcyclobutane compound (5) and/or the isopropylidene dimethylcyclobutane compound (6) (see Examples 29 and 42 below).

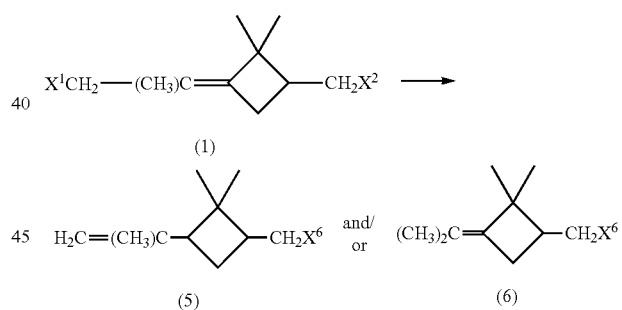

Examples of $X^6$ in the isopropenyl dimethylcyclobutane compound (5) and the isopropylidene dimethylcyclobutane compound (6) include a hydroxyl group, an acyloxy group having 1 to 10 carbon atoms including a carbon atom of a carbonyl group, an alkoxycarbonyloxy group having 2 to 10 carbon atoms including a carbon atom of a carbonyl group, an alkanesulfonyloxy group having 1 to 10 carbon atoms, an arenesulfonyloxy group having 6 to 20 carbon atoms, an alkoxy group having 1 to 12 carbon atoms, an aryloxy group having 6 to 12 carbon atoms, a silyloxy group having 3 to 20 carbon atoms or a halogen atom. Examples of $X^6$ in the isopropenyl dimethylcyclobutane compound (5) and the isopropylidene dimethylcyclobutane compound (6) include the groups mentioned for $X^1$ and $X^2$.

In a case where $X^2$ in isopropenyl dimethylcyclobutane compound (5) is maintained in the reduction reaction, $X^2$ is same as $X^6$ after the reaction. Meanwhile in a case where $X^2$ is not maintained, $X^2$ is different from $X^6$ after the reaction.

Examples of a reducing agent include hydrogen; formic acid; formates such as 6 sodium formate, ammonium formate, and triethylammonium formate; borane; alkylborane compounds such as bis(3-methyl-2-butyl)borane; alkylsilane compounds such as triethylsilane; metal hydrides such as aluminum hydride; alkyl metal hydrides such as diisobutylaluminum hydride; complex hydrides such as sodium borohydride, lithium borohydride, potassium borohydride, calcium borohydride, sodium trimethoxyborohydride, lithium triethylborohydride, sodium aluminum hydride, lithium aluminum hydride, lithium trimethoxyaluminum hydride, lithium diethoxyaluminum hydride, lithium tri-tert-butoxyaluminum hydride, sodium bis(2-methoxyethoxy)aluminum hydride; alkoxy or alkyl derivatives thereof; and diazenylating agents such as 2-nitrobenzenesulfonohydrazide and N'-isopropylidene-2-nitrobenzenesulfonohydrazide.

The reducing agent may be used alone or in combination thereof. The reducing agent may be commercially available one.

An amount of the reducing agent used is preferably from 0.7 to 100.0 mol, more preferably from 0.8 to 80.0 mol, and even more preferably from 0.9 to 60.0 mol, in terms of hydride, per mol of the dimethylcyclobutane compound (1).

The reduction reaction may be carried out in the presence of a metal catalyst.

Examples of a metal catalyst include a palladium catalyst, a nickel catalyst, an iron catalyst, a cobalt catalyst, a molybdenum catalyst, a tungsten catalyst, a rhodium catalyst, and an iridium catalyst, with a palladium catalyst being preferable in view of the yield and selectivity.

Examples of a palladium catalyst include zero-valent palladium catalysts such as tetrakis(triphenylphosphine)palladium and bis(dibenzylideneacetone)palladium catalyst; and divalent palladium catalysts such as palladium acetate, bis(triphenylphosphine)palladium diacetate, palladium trifluoroacetate, palladium chloride, bis(triphenylphosphine)palladium dichloride, allyl palladium chloride, and bis(2,4-pentanedionato)palladium.

The metal catalyst may be used alone or in combination thereof. The metal catalyst may be commercially available one.

An amount of the metal catalyst used is preferably from 0.0001 to 1 mol, more preferably from 0.0002 to 0.9 mol, and even more preferably from 0.0003 to 0.8 mol, per mol of the dimethylcyclobutane compound (1).

A ligand may be used together with the metal catalyst, if necessary.

Examples of a ligand include phosphite ester compounds such as triethyl phosphite and triphenyl phosphite; phosphine compounds such as tributylphosphine, tricyclohexylphosphine, trioctylphosphine, triphenylphosphine, 2,2'-bis(diphenylphosphino)-1,1'-binaphthyl, and 2-(di-tert-butylphosphino)biphenyl; acetone derivatives such as acetylacetone and dibenzylideneacetone; nitrile compounds such as acetonitrile and benzonitrile; nitrogen-containing compounds such as dimethylimidazolidinone, ethylenediamine, and hexamethylphosphoric triamide; and diene compounds such as 1,5-cyclooctadiene and 2,5-norbornadiene.

The ligand may be used alone or in combination thereof. The ligand may be commercially available one.

An amount of the ligand used is preferably from 0.001 to 10,000 mol, more preferably from 0.01 to 1,000 mol, and even more preferably from 0.1 to 100 mol, per 6 mol of the metal catalyst.

In a case where a diazenylating agent is used as the reducing agent, the reduction reaction may be carried out via a Mitsunobu reaction with azodicarboxylic acid ester compounds such as diethyl azodicarboxylate (DEAD) or phosphine compounds such as triphenylphosphine.

An amount of the azodicarboxylic acid ester compound in a Mitsunobu reaction is preferably from 0.7 to 100.0 mol, more preferably from 0.8 to 80.0 mol, and even more preferably from 0.9 to 60.0 mol, per mol of the dimethylcyclobutane compound (1).

An amount of the phosphine compounds in a Mitsunobu reaction is preferably from 0.7 to 100.0 mol, more preferably from 0.8 to 80.0 mol, and even more preferably from 0.9 to 60.0 mol, per mol of dimethylcyclobutane compound (1).

Examples of a solvent used in the reduction reaction include ethers such as diethyl ether, dibutyl ether, tetrahydrofuran, and 1,4-dioxane; hydrocarbons such as hexane, heptane, benzene, toluene, xylene, and cumene; chloride solvents such as methylene chloride, chloroform, and trichloroethylene; aprotic polar solvents such as N,N-dimethylformamide, 1,3-dimethyl-2-imidazolidinone, dimethyl sulfoxide, and hexamethylphosphoric triamide; nitriles such as acetonitrile and propionitrile; esters such as ethyl acetate and n-butyl acetate; alcohols such as methanol, ethanol, t-butyl alcohol, and trifluoroethanol; ketones such as acetone and 2-butanone; and water.

The solvent may be used alone or in combination thereof. The solvent may be commercially available one.

An amount of the solvent used is preferably from 10 to 150,000 g per mol of the dimethylcyclobutane compound (1).

A reaction temperature in the reduction reaction is preferably from −78 to 180° C., more preferably from −60 to 160° C., and even more preferably from −40 to 140° C.

A reaction time in the reduction reaction may be set arbitrarily. It is desirable in view of the yield to monitor the reaction with gas chromatography (GC) or silica gel thin layer chromatography (TLC) to complete the reaction. A reaction time is usually about 0.5 to 30 hours.

Examples of an isopropenyl dimethylcyclobutane compound (5) include a (1R,3R)-3-isopropenyl-2,2-dimethylcyclobutane compound of the following general formula (5-1), a (1S,3S)-3-isopropenyl-2,2-dimethylcyclobutane compound of the following general formula (5-2), a (1R,3S)-3-isopropenyl-2,2-dimethylcyclobutane compound of the following general formula (5-3), a (1S,3R)-3-isopropenyl-2,2-dimethylcyclobutane compound of the following general formula (5-4), and the racemates, diastereomeric mixtures and scalemic mixtures thereof.

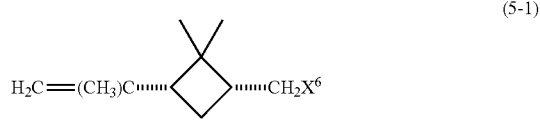

(5-1)

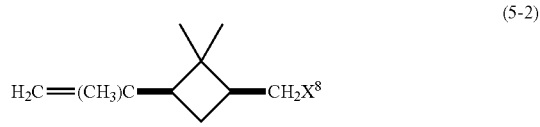

(5-2)

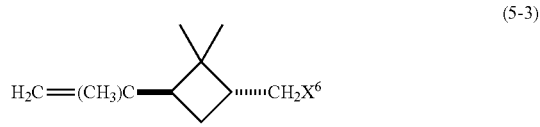

(5-3)

(5-4)

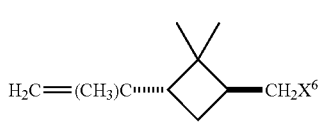

Examples of an isopropenyl dimethylcyclobutane compound (5) include an isopropenyl dimethylcyclobutane compound having an acyloxymethyl group, an isopropenyl dimethylcyclobutane compound having a halomethyl group, an isopropenyl dimethylcyclobutane compound having a hydroxymethyl group, an isopropenyl dimethylcyclobutane compound having an alkanesulfonyloxymethyl group, and an isopropenyl dimethylcyclobutane compound having an alkoxymethyl group.

Examples of an isopropenyl dimethylcyclobutane compound having an acyloxymethyl group include (3-isopropenyl-2,2-dimethylcyclobutyl)methyl acylate compounds such as (3-isopropenyl-2,2-dimethylcyclobutyl)methyl acetate, (3-isopropenyl-2,2-dimethylcyclobutyl)methyl 2-methylbutanoate, and (3-isopropenyl-2,2-dimethylcyclobutyl)methyl 3-methyl-3-butenoate.

Examples of an isopropenyl dimethylcyclobutane compound having a halomethyl group include 1-halomethyl-3-isopropenyl-2,2-dimethylcyclobutane compounds such as 1-chloromethyl-3-isopropenyl-2,2-dimethylcyclobutane.

Examples of an isopropenyl dimethylcyclobutane compound having a hydroxymethyl group include (3-isopropenyl-2,2-dimethylcyclobutyl)methanol.

Examples of an isopropenyl dimethylcyclobutane compound having an alkanesulfonyloxymethyl group include (3-isopropenyl-2,2-dimethylcyclobutyl)methyl alkane sulfonate compounds such as (3-isopropenyl-2,2-dimethylcyclobutyl)methyl methanesulfonate.

Examples of an isopropenyl dimethylcyclobutane compound having an alkoxymethyl group include 1-alkoxymethyl-3-isopropenyl-2,2-dimethylcyclobutane compounds such as 2-[(3-isopropenyl-2,2-dimethylcyclobutyl)methoxy]tetrahydropyran and (3-isopropenyl-2,2-dimethylcyclobutyl)methoxymethylbenzene.

Examples of an isopropylidene dimethylcyclobutane compound (6) include (1R)-3-isopropylidene-2,2-dimethylcyclobutane compound of the following general formula (6-1), (1S)-3-isopropylidene-2,2-dimethylcyclobutane compound of the following general formula (6-2), and the racemates and scalemic mixtures thereof.

(6-1)

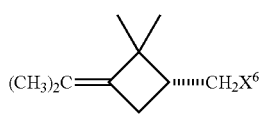

(6-2)

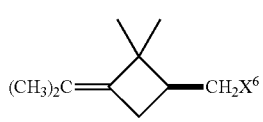

Examples of an isopropylidene dimethylcyclobutane compound (6) include an isopropylidene dimethylcyclobutane compound having an acyloxymethyl group, an isopropylidene dimethylcyclobutane compound having a halomethyl group, an isopropylidene dimethylcyclobutane compound having a hydroxymethyl group, an isopropylidene dimethylcyclobutane compound having an alkanesulfonyloxymethyl group, and an isopropylidene dimethylcyclobutane compound having an alkoxymethyl group.

Examples of an isopropylidene dimethylcyclobutane compound having an acyloxymethyl group include (3-isopropylidene-2,2-dimethylcyclobutyl)methyl acylate compounds such as (3-isopropylidene-2,2-dimethylcyclobutyl)methyl acetate, (3-isopropylidene-2,2-dimethylcyclobutyl)methyl 2-methylbutanoate, (3-isopropylidene-2,2-dimethylcyclobutyl)methyl 3-methyl-2-butenoate, and (3-isopropylidene-2,2-dimethylcyclobutyl)methyl 3-methyl-3-butenoate.

Examples of an isopropylidene dimethylcyclobutane compound having a halomethyl group include 1-halomethyl-3-isopropylidene-2,2-dimethylcyclobutane compounds such as 1-chloromethyl-3-isopropylidene-2,2-dimethylcyclobutane.

Examples of an isopropylidene dimethylcyclobutane compound having a hydroxymethyl group include (3-isopropylidene-2,2-dimethylcyclobutyl)methanol. Examples of an isopropylidene dimethylcyclobutane compound having an alkanesulfonyloxymethyl group include (3-isopropylidene-22-dimethylcyclobutyl)methylalkanesulfonate compounds such as (3-isopropylidene-2,2-dimethylcyclobutyl)methyl methanesulfonate.

Examples of an isopropylidene dimethylcyclobutane compound having an alkoxymethyl group include 1-alkoxymethyl-3-isopropylidene-2,2-dimethylcyclobutane compounds such as 2-[(3-isopropylidene-2,2-dimethylcyclobutyl)methoxy]tetrahydropyran and (3-isopropylidene-2,2-dimethylcyclobutyl)methoxymethylbenzene.

The isopropenyl dimethylcyclobutane compound of the following general formula (5A), having an alkoxymethyl group, and the isopropylidene dimethylcyclobutane compound of the following general formula (6A) may be produced by subjecting the dimethylcyclobutane compound (1G), having a halogen atom and an alkoxy group, to a reduction reaction, as shown in the following chemical reaction formula (see Example 29 below). The reduction reaction may be carried out using a reducing agent, if necessary, in the presence of a metal catalyst and a ligand.

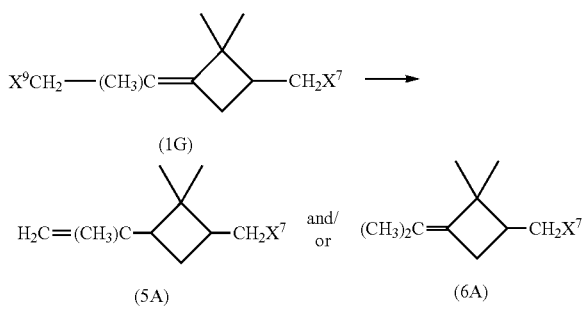

$X^7$ in the isopropenyl dimethylcyclobutane compound (5A), having an alkoxymethyl group, and the isopropylidene dimethylcyclobutane compound (6A) is as defined above.

The isopropenyl dimethylcyclobutane compound (5A), having an alkoxymethyl group, and the isopropylidene dimethylcyclobutane compound (6A) may be produced by subjecting the dimethylcyclobutane compound (1K), having a phosphonio group and an alkoxy group, to a reduction reaction, as shown in the following chemical reaction formula (see Example 30 below). The reduction reaction may be carried out using a reducing agent, if necessary, in the presence of a metal catalyst and a ligand.

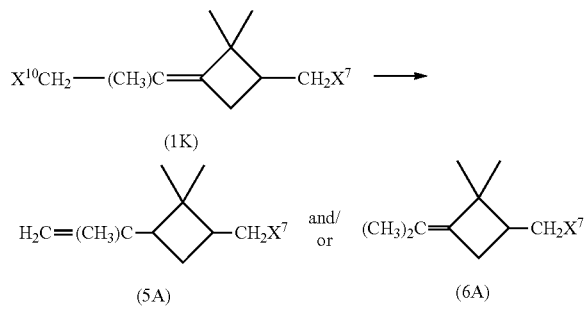

The isopropenyl dimethylcyclobutane compound (5A), having an alkoxymethyl group, and the isopropylidene dimethylcyclobutane compound (6A) may be produced by subjecting the dimethylcyclobutane compound (1G), having a halogen atom and an alkoxy group, to a reduction reaction, as shown in the following chemical reaction formula (see Example 31 below). The reduction reaction may be carried out using a reducing agent, if necessary, in the presence of a metal catalyst and a ligand.

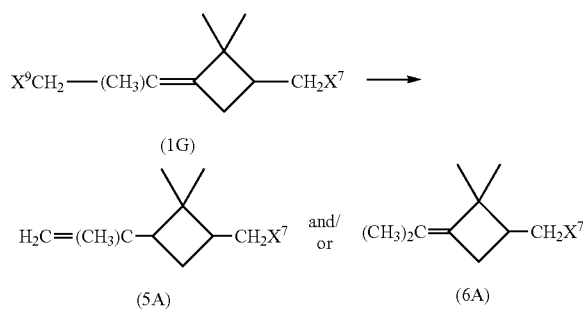

The isopropenyl dimethylcyclobutane compound of the following general formula (5B), having a hydroxymethyl group, and/or the isopropylidene dimethylcyclobutane compound of the following general formula (6B) may be produced by subjecting the dimethylcyclobutane compound (1D), having an acyloxy group and an alkoxy group, to a reduction reaction, as shown in the following chemical reaction formula (see Example 32 below). The reduction reaction may be carried out using a reducing agent in the presence of a metal catalyst and, if necessary, a ligand.

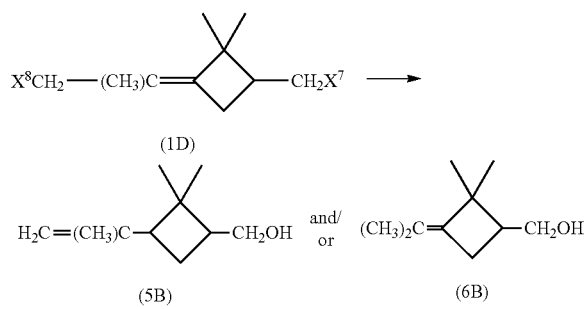

The isopropenyl dimethylcyclobutane compound (5A), having an alkoxymethyl group, and the isopropylidene dimethylcyclobutane compound (6A) may be produced by subjecting the dimethylcyclobutane compound (1D), having an acyloxy group and an alkoxy group, to a reduction reaction, as shown in the following chemical reaction formula (see Example 33 below). The reduction reaction may be carried out using a reducing agent in the presence of a metal catalyst and, if necessary, a ligand.

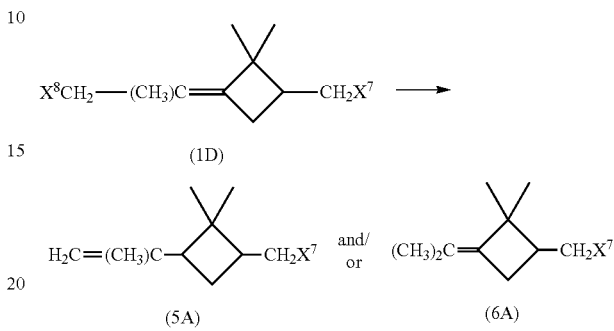

The isopropenyl dimethylcyclobutane compound (5A), having an alkoxymethyl group, and the isopropylidene dimethylcyclobutane compound (6A) may be produced by subjecting the dimethylcyclobutane compound (1C), having a hydroxyl group and an alkoxy group, to a reduction reaction, as shown in the following chemical reaction formula (see Example 34 below). The reduction reaction may be carried out using a reducing agent such as a diazenilating agent.

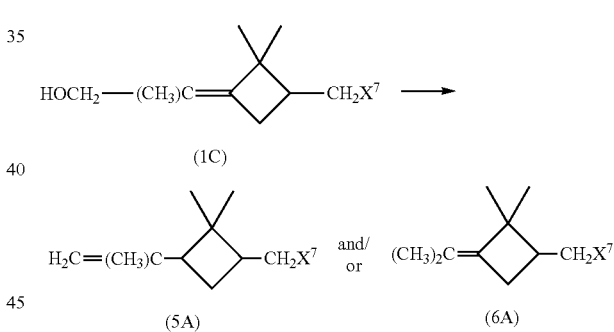

The isopropenyl dimethylcyclobutane compound of the following general formula (5C), having an acyloxymethyl group, and the isopropylidene dimethylcyclobutane compound of the following general formula (6C) may be produced by subjecting the dimethylcyclobutane compound (1F), having two acyloxy groups, to a reduction reaction, as shown in the following chemical reaction formula (see Examples 35 to 39 below). The reduction reaction may be carried out using a reducing agent in the presence of a metal catalyst and, if necessary, a ligand.

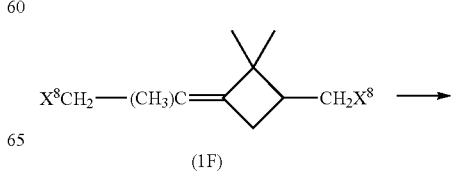

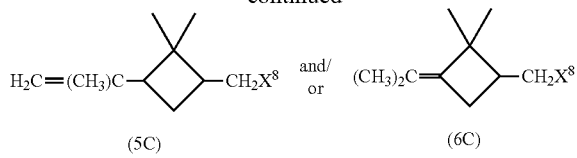

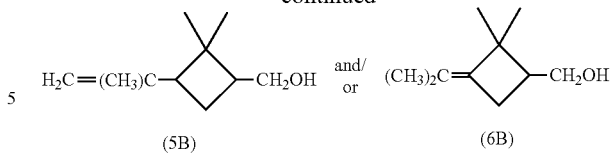

$X^8$ is as defined above.

The isopropenyl dimethylcyclobutane compound of the following general formula (5D), having a halomethyl group, and the isopropylidene dimethylcyclobutane compound of the following general formula (6D) may be produced by subjecting the dimethylcyclobutane compound (1H), having two halogen atoms, to a reduction reaction, as shown in the following chemical reaction formula (see Example 40 below). The reduction reaction may be carried out using a reducing agent in the presence of a metal catalyst and, if necessary, a ligand.

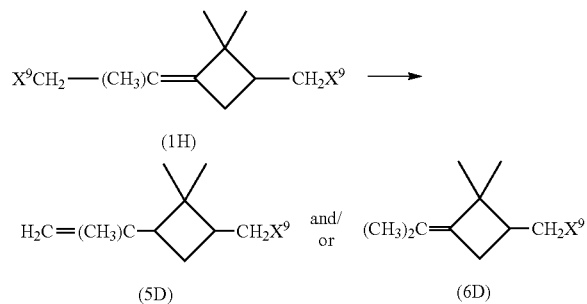

$X^9$ is as defined above.

The isopropenyl dimethylcyclobutane compound (5B), having a hydroxymethyl group, and the isopropylidene dimethylcyclobutane compound (6B) may be produced by subjecting the dimethylcyclobutane compound (1I), having a phosphonio group and a hydroxyl group, to a reduction reaction, as shown in the following chemical reaction formula (see Example 41 below). The reduction reaction may be carried out using a reducing agent, if necessary, in the presence of a metal catalyst and a ligand.

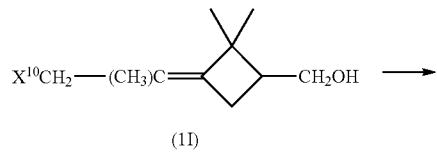

The isopropenyl dimethylcyclobutane compound (5B), having a hydroxymethyl group, and the isopropylidene dimethylcyclobutane compound (6B) may be produced by subjecting the dimethylcyclobutane compound (1J), having a halogen atom and an acyloxy group, to a reduction reaction, as shown in the following chemical reaction formula (see Example 42 below). The reduction reaction may be carried out using a reducing agent, if necessary, in the presence of a metal catalyst and a ligand.

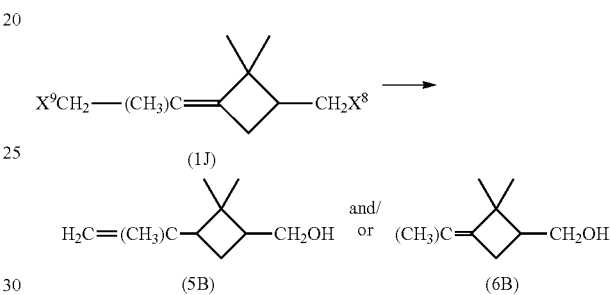

If necessary, the isopropenyl dimethylcyclobutane compound (5'), having another substituent, and/or the isopropylidene dimethylcyclobutane compound (6'), having another substituent, can be obtained by changing a specific group, $X^6$, in the isopropenyl dimethylcyclobutane compound (5) and/or the isopropylidene dimethylcyclobutane compound (6) to another group, $X^6$, among the options for $X^6$ (see Examples 43 to 52 below).

The changing of the group may be carried out by a known method.

For instance, the isopropenyl dimethylcyclobutane compound (5C), having an acyloxymethyl group, and the isopropylidene dimethylcyclobutane compound (6C) may be produced by subjecting the isopropenyl dimethylcyclobutane compound (5D), having a halomethyl group, and/or the isopropylidene dimethylcyclobutane compound (6D) to an acyloxylation reaction with a carboxylate salt, as shown in the following chemical reaction formula (see Example 46 below).

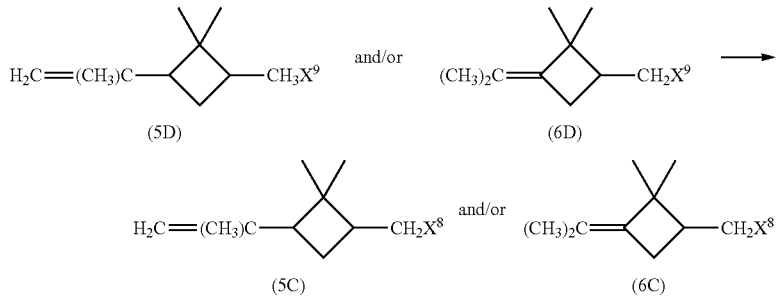

The chemical reaction formula shows the production of a mixture of the compounds (5C) and (6C) from a mixture of the compounds (5D) and (6D), the production of the compound (5C) from the compound (5D), and the production of the compound (6C) from the compound (6D).

Examples of a carboxylate salt include metal carboxylates such as lithium acetate, sodium acetate, potassium acetate, cesium acetate, magnesium acetate, and calcium acetate; and ammonium carboxylates such as ammonium acetate and tetrabutylammonium acetate.

The carboxylate salt may be used alone or in combination thereof. The carboxylate salt may be commercially available one.

The carboxylate salt may be formed by reacting a carboxylic acid with a base such as sodium hydroxide, potassium carbonate and tetrabutylammonium hydroxide in situ in a reaction system.

An amount of the carboxylate salt used is preferably from 0.7 to 10 mol, more preferably from 0.8 to 8 mol, and even more preferably from 0.9 to 6 mol, per mol of a total of the isopropenyl dimethylcyclobutane compound (5D), having a halomethyl group, and the isopropylidene dimethylcyclobutane compound (6D).

The acyloxylation reaction may be carried out in the presence of a halide.

Examples of a halide include metal halides such as lithium iodide, sodium iodide, potassium iodide, cesium iodide, magnesium iodide, calcium iodide, lithium bromide, sodium bromide, potassium bromide, cesium bromide, magnesium bromide, and calcium bromide; ammonium halide compounds such as ammonium iodide, ammonium bromide, tetrabutylammonium iodide, tetrabutylammonium bromide, and tetrabutylammonium chloride.

The halide may be used alone or in combination thereof. The halide may be commercially available one.

An amount of the halide used is preferably from 0.0001 to 10 mol, more preferably from 0.0002 to 8 mol, and even more preferably from 0.0003 to 6 mol, per mol of a total of the isopropenyl dimethylcyclobutane compound (5D), having a halomethyl group, and the isopropylidene dimethylcyclobutane compound (6D).

Examples of a solvent used in the acyloxylation reaction include ethers such as diethyl ether, dibutyl ether, tetrahydrofuran, and 1,4-dioxane; hydrocarbons such as hexane, heptane, benzene, toluene, xylene, and cumene; chloride solvents such as methylene chloride, chloroform, and trichloroethylene; aprotic polar solvents such as N,N-dimethylacetamide, N,N-dimethylformamide, 1,3-dimethyl-2-imidazolidinone, dimethyl sulfoxide, and hexamethylphosphoric triamide; nitriles such as acetonitrile and propionitrile; esters such as ethyl acetate and n-butyl acetate; alcohols such as methanol, ethanol, and t-butyl alcohol; and water.

The solvent may be used alone or in combination thereof. The solvent may be commercially available one.

An amount of the solvent used is preferably from 10 to 10,000 g per mol of a total of the isopropenyl dimethylcyclobutane compound (5D), having a halomethyl group, and the isopropylidene dimethylcyclobutane compound (6D).

A reaction temperature in the acyloxylation reaction is preferably from −78 to 200° C., more preferably from −60 to 180° C., and even more preferably from −40 to 160° C.

A reaction time in the acyloxylation reaction may be set arbitrarily. It is desirable in view of the yield to monitor the reaction with gas chromatography (GC) or silica gel thin layer chromatography (TLC) to complete the reaction. A reaction time is usually about 0.5 to 24 hours.

The isopropenyl dimethylcyclobutane compound (5C), having an acyloxymethyl group, and the isopropylidene dimethylcyclobutane compound (6C) may be produced by subjecting the isopropenyl dimethylcyclobutane compound (5B), having a hydroxymethyl group, and/or the isopropylidene dimethylcyclobutane compound (6B) to an acylation reaction with an acylating agent, as shown in the following chemical reaction formula (see Examples 44, 45 and 50 below).

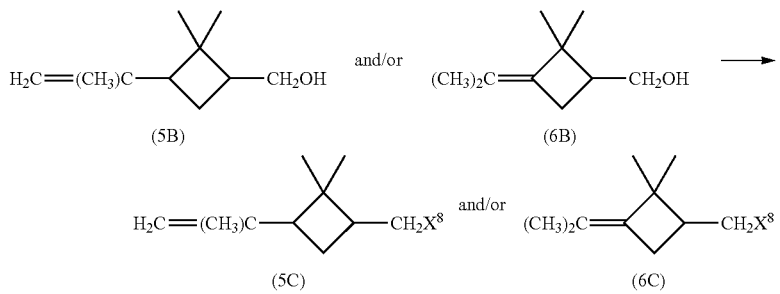

The chemical reaction formula shows the production of a mixture of the compounds (5C) and (6C) from a mixture of the compounds (5B) and (6B), the production of the compound (5C) from the compound (5B), and the production of the compound (6C) from the compound (6B).

Examples of an acylating agent include acid anhydrides such as acetic anhydride; and acid chlorides such as acetyl chloride.

The acylating agent may be used alone or in combination thereof. The acylating agent may be commercially available one.

An amount of the acylating agent used is preferably from 0.7 to 100 mol, more preferably from 0.8 to 50 mol, and even more preferably from 0.9 to 20 mol, per mol of a total of the isopropenyl dimethylcyclobutane compound (5B), having a hydroxymethyl group, and the isopropylidene dimethylcyclobutane compound (6B).

Examples of a base used in the acylation reaction include alkoxides such as sodium methoxide, sodium ethoxide, sodium t-butoxide, sodium t-amyloxide, lithium methoxide, lithium ethoxide, lithium t-butoxide, lithium t-amyloxide, potassium methoxide, potassium ethoxide, potassium t-butoxide, and potassium t-amyloxide; organometallic compounds such as methyllithium, ethyllithium, n-butyllithium, methylmagnesium chloride, and dimsyl sodium; metal amides such as sodium amide, lithium amide, lithium diisopropylamide, lithium hexamethyldisilazide, sodium hexamethyldisilazide, potassium hexamethyldisilazide, and lithium dicyclohexylamide; metal hydrides such as sodium hydride, potassium hydride, and calcium hydride; and organic base compounds such as triethylamine, diisopropylethylamine, tributylamine, N,N-dimethylaniline, N,N-diethylaniline, pyridine, 4-dimethylaminopyridine, imidazole, quinoline, pyrrolidine, piperidine, collidine, lutidine, morpholine, and 1,8-diazabicyclo[5.4.0]-7-undecene.

The base may be used alone or in combination thereof. The base may be commercially available one.

An amount of the base used is preferably from 0.7 to 100 mol, more preferably from 0.8 to 50 mol, and even more preferably from 0.9 to 20 mol, per mol of a total of the isopropenyl dimethylcyclobutane compound (5B), having a hydroxymethyl group, and the isopropylidene dimethylcyclobutane compound (6B).

Examples of a solvent used in the acylation reaction include ethers such as diethyl ether, dibutyl ether, tetrahydrofuran, and 1,4-dioxane; hydrocarbons such as hexane, heptane, benzene, toluene, xylene, and cumene; chloride solvents such as methylene chloride, chloroform, and trichloroethylene; aprotic polar solvents such as N,N-dimethylformamide, 1,3-dimethyl-2-imidazolidinone, dimethyl sulfoxide, and hexamethylphosphoric triamide; nitriles such as acetonitrile and propionitrile; esters such as ethyl acetate and n-butyl acetate; and water.

The solvent may be used alone or in combination thereof. The solvent may be commercially available one.

An amount of the solvent used is preferably from 10 to 15,000 g per mol of a total of the isopropenyl dimethylcyclobutane compound (5B), having a hydroxymethyl group, and the isopropylidene dimethylcyclobutane compound (6B).

A reaction temperature in the acylation reaction is preferably from −78 to 180° C., more preferably from −60 to 160° C., and even more preferably from −40 to 140° C.

A reaction time in the acylation reaction may be set arbitrarily. It is desirable in view of the yield to monitor the reaction with gas chromatography (GC) or silica gel thin layer chromatography (TLC) to complete the reaction. A reaction time is usually about 0.5 to 24 hours.

The isopropenyl dimethylcyclobutane compound of the following general formula (5G), having an alkanesulfonyloxymethyl group, and the isopropylidene dimethylcyclobutane compound of the following general formula (6G) may be produced by subjecting the isopropenyl dimethylcyclobutane compound (5B), having a hydroxymethyl group, and/or an isopropylidene dimethylcyclobutane compound (6B) to an alkanesulfonylation reaction with an alkanesulfonylating agent, as shown in the following chemical reaction formula (see Example 47 below).

The chemical reaction formula shows the production of a mixture of the compounds (5G) and (6G) from a mixture of the compounds (5B) and (6B), the production of the compound (5G) from the compound (5B), and the production of the compound (6G) from the compound (6B).

$X^{11}$ represents an alkanesulfonyloxy group having 1 to 10 carbon atoms. Examples of an alkanesulfonyloxy group having 1 to 10 carbon atoms include those defined for $X^1$ and $X^2$.

Examples of an alkane sulfonylating agent include alkane sulfonic anhydrides such as a methane sulfonic anhydride; and alkane sulfonyl chlorides such as a methane sulfonyl chloride.

The alkane sulfonylating agent may be used alone or in combination thereof. The alkane sulfonylating agent may be commercially available one.

An amount of the alkane sulfonylating agent used is 0.7 to 100 mol, more preferably from 0.8 to 50 mol, and even more preferably from 0.9 to 20 mol, per mol of a total of the isopropenyl dimethylcyclobutane compound (5B), having a hydroxymethyl group, and the isopropylidene dimethylcyclobutane compound (6B).

Examples of a base used in the alkanesulfonylation reaction include alkoxides such as sodium methoxide, sodium ethoxide, sodium t-butoxide, sodium t-amyloxide, lithium methoxide, lithium ethoxide, lithium t-butoxide, lithium t-amyloxide, potassium methoxide, potassium ethoxide, potassium t-butoxide, and potassium t-amyloxide; organometallic compounds such as methyllithium, ethyllithium, n-butyllithium, methylmagnesium chloride, and dimsyl sodium; metal amides such as sodium amide, lithium amide, lithium diisopropylamide, lithium hexamethyldisilazide, sodium hexamethyldisilazide, potassium hexamethyldisilazide, and lithium dicyclohexylamide; metal hydrides such as sodium hydride, potassium hydride, and calcium hydride; and organic base compounds such as triethylamine, diisopropylethylamine, tributylamine, N,N-dimethylaniline, N,N-diethylaniline, pyridine, 4-dimethylaminopyridine, imidazole, quinoline, pyrrolidine, piperidine, collidine, lutidine, morpholine, and 1,8-diazabicyclo[5.4.0]-7-undecene.

The base may be used alone or in combination thereof. The base may be commercially available one.

An amount of the base used is preferably from 0.7 to 100 mol, more preferably from 0.8 to 50 mol, and even more preferably from 0.9 to 20 mol, per mol of a total of the isopropenyl dimethylcyclobutane compound (5B), having a hydroxymethyl group, and the isopropylidene dimethylcyclobutane compound (6B).

Examples of a solvent used in the alkanesulfonylation reaction include ethers such as diethyl ether, dibutyl ether, tetrahydrofuran, and 1,4-dioxane; hydrocarbons such as hexane, heptane, benzene, toluene, xylene, and cumene;

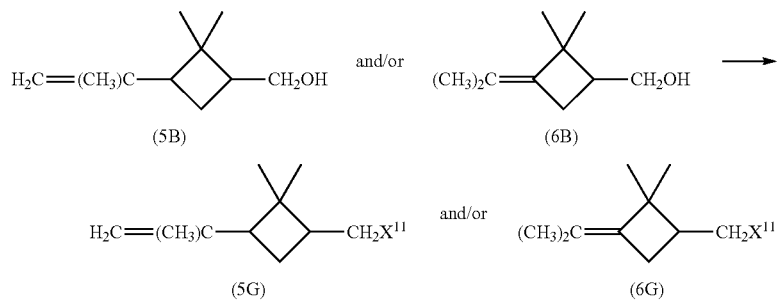

chloride solvents such as methylene chloride, chloroform, and trichloroethylene; aprotic polar solvents such as N,N-dimethylformamide, 1,3-dimethyl-2-imidazolidinone, dimethyl sulfoxide, and hexamethylphosphoric triamide; nitriles such as acetonitrile and propionitrile; esters such as ethyl acetate and n-butyl acetate; and water.

The solvent may be used alone or in combination thereof. The solvent may be commercially available one.

An amount of the solvent used is preferably from 10 to 10,000 g per mol of a total of the isopropenyl dimethylcyclobutane compound (5B), having a hydroxymethyl group, and the isopropylidene dimethylcyclobutane compound (6B).

A reaction temperature in the alkanesulfonylation reaction is preferably from −78 to 180° C., more preferably from −60 to 160° C., and even more preferably from −40 to 140° C.

A reaction time in the alkanesulfonylation reaction may be set arbitrarily. It is desirable in view of the yield to monitor the reaction with gas chromatography (GC) or silica gel thin layer chromatography (TLC) to complete the reaction. A reaction time is usually about 0.5 to 24 hours.

The isopropenyl dimethylcyclobutane compound (5C), having an acyloxymethyl group, and the isopropylidene dimethylcyclobutane compound (6C) may be produced by subjecting the isopropenyl dimethylcyclobutane compound (5G), having an alkanesulfonyloxymethyl group, and/or an isopropylidene dimethylcyclobutane compound (60) to an acyloxylation reaction with a carboxylate salt, as shown in the following chemical reaction formula (see Example 48 below).

from 0.9 to 6 mol, per mol of a total of the isopropenyl dimethylcyclobutane compound (5G), having an alkanesulfonyloxymethyl group, and the isopropylidene dimethylcyclobutane compound (6G).

The acyloxylation reaction may be carried out in the presence of a halide.

Examples of a halide include metal halides such as lithium iodide, sodium iodide, potassium iodide, cesium iodide, magnesium iodide, calcium iodide, lithium bromide, sodium bromide, potassium bromide, cesium bromide, magnesium bromide, and calcium bromide; and ammonium halide compounds such as ammonium iodide, ammonium bromide, tetrabutyl ammonium iodide, tetrabutyl ammonium bromide, and tetrabutyl ammonium chloride.

The halide may be used alone or in combination thereof. The halide may be commercially available one.

An amount of the halide used is 0.0001 to 10 mol, more preferably from 0.0002 to 8 mol, and even more preferably from 0.003 to 6 mol, per mol of a total of the isopropenyl dimethylcyclobutane compound (50), having an alkanesulfonyloxymethyl group, and the isopropylidene dimethylcyclobutane compound (60).

Examples of a solvent used in the acyloxylation reaction include ethers such as diethyl ether, dibutyl ether, tetrahydrofuran, and 1,4-dioxane; hydrocarbons such as hexane, heptane, benzene, toluene, xylene, and cumene; chloride solvents such as methylene chloride, chloroform, and trichloroethylene; aprotic polar solvents such as N,N-dimethylformamide, 1,3-dimethyl-2-imidazolidinone, dimethyl sulfoxide, and hexamethylphosphoric triamide; nitriles such

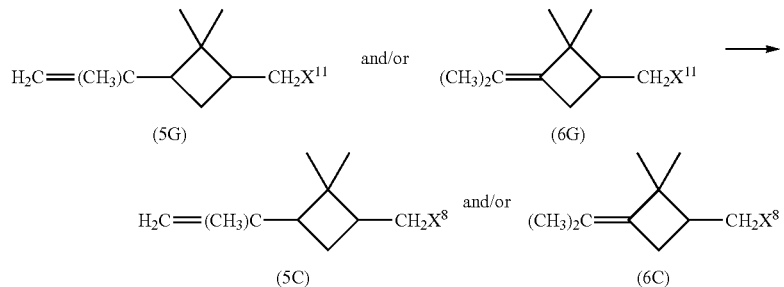

The chemical reaction formula shows the production of a mixture of the compounds (5C) and (6C) from a mixture of the compounds (5) and (6G), the production of the compound (5C) from the compound (5G), and the production of the compound (6C) from the compound (6G).

Examples of a carboxylate salt include alkali metal salts of 3-methyl-2-butenoic acid such as lithium 3-methyl-2-butenoate, sodium 3-methyl-2-butenoate, potassium 3-methyl-2-butenoate, and cesium 3-methyl-2-butenoate; alkaline earth metal salts of 3-methyl-2-butenoic acid such as magnesium 3-methyl-2-butenoate and calcium 3-methyl-2-butenoate; and ammonium carboxylates such as ammonium 3-methyl-2-butenoate and tetrabutylammonium 3-methyl-2-butenoate.

The carboxylate salt may be used alone or in combination thereof. The carboxylate may be commercially available one.

The carboxylate salt may be formed from a carboxylic acid and a base such as sodium hydroxide, potassium carbonate, and tetrabutylammonium hydroxide in situ in a reaction system.

An amount of the carboxylate salt used is 0.7 to 10 mol, more preferably from 0.8 to 8 mol, and even more preferably as acetonitrile and propionitrile; esters such as ethyl acetate and n-butyl acetate; alcohols such as methanol, ethanol, and t-butyl alcohol; and water.

The solvent may be used alone or in combination thereof. The solvent may be commercially available one.

An amount of the solvent used is preferably from 10 to 10,000 g per mol of a total of the isopropenyl dimethylcyclobutane compound (5G), having an alkanesulfonyloxymethyl group, and/or the isopropylidene dimethylcyclobutane compound (6G).

A reaction temperature in the acyloxylation reaction is preferably from −78 to 180° C., more preferably from −60 to 160° C., and even more preferably from −40 to 140° C.

A reaction time in the acyloxylation reaction may be set arbitrarily. It is desirable in view of the yield to monitor the reaction with gas chromatography (GC) or silica gel thin layer chromatography (TLC) to complete the reaction. A reaction time is usually about 0.5 to 24 hours.

The isopropenyl dimethylcyclobutane compound (5B), having a hydroxymethyl group, and the isopropylidene dimethylcyclobutane compound (6B) may be produced by subjecting the isopropenyl dimethylcyclobutane compound (5A), having an alkoxymethyl group, and/or an isopropylidene dimethylcyclobutane compound (6A) to a deprotection reaction with an acid, as shown in the following chemical reaction formula (see Example 43 below).

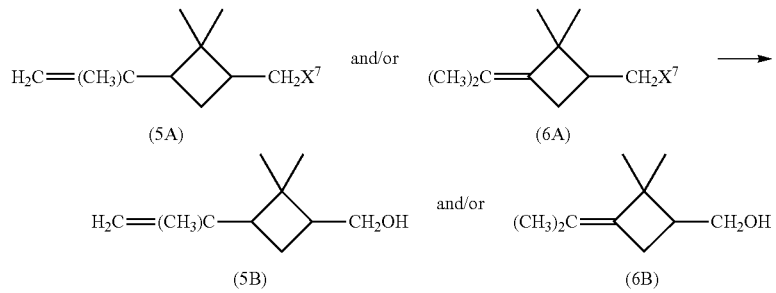

The chemical reaction formula shows the production of a mixture of the compounds (5B) and (6B) from a mixture of the compounds (5A) and (6A), the production of the compound (5B) from the compound (5A), and the production of the compound (6B) from the compound (6A).

Examples of an acid include inorganic acids such as hydrochloric acid, hydrobromic acid, hydroiodic acid, sulfuric acid, nitric acid, phosphoric acid, or a their salts; organic acids such as formic acid, acetic acid, propionic acid, oxalic acid, trifluoroacetic acid, methanesulfonic acid, benzenesulfonic acid, p-toluenesulfonic acid, and naphthalenesulfonic acid, or salts thereof; Lewis acids such as lithium tetrafluoroborate, boron trifluoride, boron trichloride, boron tribromide, aluminum trichloride, zinc chloride, zinc bromide, zinc iodide, tin tetrachloride, tin tetrabromide, tin dichloride, titanium tetrachloride, titanium tetrabromide, and trimethyliodosilane; oxides such as alumina, silica gel, and titania; and minerals such as montmorillonite.

The acid may be used alone or in combination thereof. The acid may be commercially available one.

An amount of the acid used is preferably from 0.00001 to 10,000 mol, more preferably from 0.0001 to 1,000 mol, and even more preferably from 0.001 to 100, per mol of a total of the isopropenyl dimethylcyclobutane compound (5A), having an alkoxymethyl group, and the isopropylidene dimethylcyclobutane compound (6A).

Examples of a solvent used in the deprotection reaction include ethers such as diethyl ether, dibutyl ether, tetrahydrofuran, and 1,4-dioxane; hydrocarbons such as hexane, heptane, benzene, toluene, xylene, and cumene; chloride solvents such as methylene chloride, chloroform, and trichloroethylene; aprotic polar solvents such as N,N-dimethylformamide, 1,3-dimethyl-2-imidazolidinone, dimethyl sulfoxide, and hexamethylphosphoric triamide; nitriles such as acetonitrile and propionitrile; esters such as ethyl acetate and n-butyl acetate; alcohols such as methanol, ethanol, and t-butyl alcohol; and water.

The solvent may be used alone or in combination thereof. The solvent may be commercially available one.

An amount of the solvent used is preferably from 10 to 10,000 g per mol of a total of the isopropenyl dimethylcyclobutane compound (5A), having an alkoxymethyl group, and the isopropylidene dimethylcyclobutane compound (6A).

A reaction temperature in the deprotection reaction is preferably from −78 to 180° C., more preferably from −60 to 160° C., and even more preferably from −40 to 140° C.

A reaction time in the deprotection reaction may be set arbitrarily. It is desirable in view of the yield to monitor the reaction with gas chromatography (GC) or silica gel thin layer chromatography (TLC) to complete the reaction. A reaction time is usually about 0.5 to 24 hours.

The isopropenyl dimethylcyclobutane compound (5B) having a hydroxymethyl group, and the isopropylidene dimethylcyclobutane compound (6B) may be produced by subjecting the isopropenyl dimethylcyclobutane compound (5C), having an acyloxymethyl group, and/or an isopropylidene dimethylcyclobutane compound (6C) to a deprotection reaction with a base, as shown in the following chemical reaction formula (see Example 49 below).

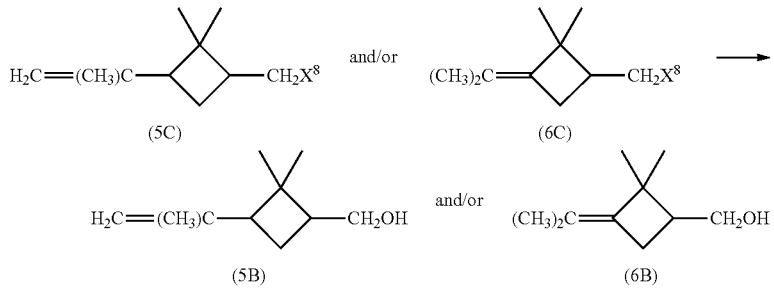

The chemical reaction formula shows the production of a mixture of the compounds (5B) and (6B) from a mixture of the compounds (5C) and (6C), the production of the compound (5B) from the compound (5C), and the production of the compound (6B) from the compound (6C).

Examples of a base used in the deprotection reaction include nitrogen compounds such as ammonia and hydrazine; metal carbonates such as lithium carbonate, sodium carbonate, and potassium carbonate; metal hydroxides such as lithium hydroxide, sodium hydroxide, and potassium hydroxide; alkoxides such as sodium methoxide, sodium ethoxide, sodium t-butoxide, sodium t-amyloxide, lithium methoxide, lithium ethoxide, lithium t-butoxide, lithium t-amyloxide, potassium methoxide, potassium ethoxide, potassium t-butoxide, and potassium t-amyloxide; and organic base compounds such as triethylamine, diisopropylethylamine, tributylamine, N,N-dimethylaniline, N,N-diethylaniline, pyridine, 4-dimethylaminopyridine, imidazole, quinoline, pyrrolidine, piperidine, collidine, lutidine, morpholine, and 1,8-diazabicyclo[5.4.0]-7-undecene.

The base may be used alone or in combination thereof. The carboxylate salt may be commercially available one.

An amount of the base used is 0.00001 to 10,000 mol, more preferably from 0.0001 to 1,000 mol, and even more preferably from 0.001 to 100 mol, per mol of a total of the isopropenyl dimethylcyclobutane compound (5C), having an acyloxymethyl group, and the isopropylidene dimethylcyclobutane compound (6C).

Examples of a solvent used in the deprotection reaction include ethers such as diethyl ether, dibutyl ether, tetrahydrofuran, and 1,4-dioxane; hydrocarbons such as hexane, heptane, benzene, toluene, xylene, and cumene; chloride solvents such as methylene chloride, chloroform, and trichloroethylene; aprotic polar solvents such as N,N-dimethylformamide, 1,3-dimethyl-2-imidazolidinone, dimethyl sulfoxide, and hexamethylphosphoric triamide; nitriles such as acetonitrile and propionitrile; esters such as ethyl acetate and n-butyl acetate; alcohols such as methanol, ethanol, and t-butyl alcohol; and water.

The solvent may be used alone or in combination thereof. The solvent may be commercially available one.

An amount of the solvent used is preferably from 10 to 10,000 g per mol of a total of the isopropenyl dimethylcyclobutane compound (5C), having an acyloxymethyl group, and the isopropylidene dimethylcyclobutane compound (6C).

A reaction temperature in the deprotection reaction is preferably from −78 to 180° C., more preferably from −60 to 160° C., and even more preferably from −40 to 140° C.

A reaction time in the deprotection reaction may be set arbitrarily. It is desirable in view of the yield to monitor the reaction with gas chromatography (GC) or silica gel thin layer chromatography (TLC) to complete the reaction. A reaction time is usually about 0.5 to 24 hours.

A sex pheromone composition may be prepared from (1R,3R)-(3-isopropenyl-2,2-dimethylcyclobutyl)methyl acetate (5-1; $X^6$=an acetoxy group) obtained above, and an attractant for *Planococcus citri* (generic name: *Citrus* mealybug) may be produced from the pheromone composition.

First, the pheromone composition will be explained hereinafter.

The sex pheromone composition comprises at least (1R, 3R)-(3-isopropenyl-2,2-dimethylcyclobutyl) methyl acetate, which is a sex pheromone of *Planococcus citri*.

The cis-form enantiomer, (1S,3S)-(3-isopropenyl-2,2-dimethylcyclobutyl) methyl acetate is not a sex pheromone substance, but does not disturb the attraction (J. Econ. Entomol. 97, 361 (2004)). Therefore, the aforesaid cis-form may be included in the sex pheromone composition, and for example, a racemic mixture and a scalemic mixture with cis-(3-isopropenyl-2,2-dimethylcyclobutyl)methyl acetate may be used.

The pheromone composition may comprise a trans-from: (1S,3R)-(3-isopropenyl-2,2-dimethylcyclobutyl)methyl acetate and/or (1R,3S)-(3-isopropenyl-2,2-dimethylcyclobutyl)methyl acetate, and, if necessary, may further comprise a stereoisomer of (3-isopropylidene-2,2-dimethylcyclobutyl)methyl acetate (6; $X^6$=an acetoxy group): (R)-(3-isopropylidene-2,2-dimethylcyclobutyl)methyl acetate and/or (S)-(3-isopropylidene-2,2-dimethylcyclobutyl)methyl acetate.

A content of (S, 3S)-(3-isopropenyl-2,2-dimethylcyclobutyl)methyl acetate in the pheromone composition is 2 to 100 parts by weight, relative to 100 weight by parts of (1R,3R)-(3-isopropenyl-2,2-dimethylcyclobutyl)methyl acetate.

A content of (1S,3R)-(3-isopropenyl-2,2-dimethylcyclobutyl)methyl acetate in the pheromone composition is 4 to 97 parts by weight, relative to 100 weight by parts of (1R,3R)-(3-isopropenyl-2,2-dimethylcyclobutyl)methyl acetate.

A content of (1R,3S)-(3-isopropenyl-2,2-dimethylcyclobutyl)methyl acetate in the pheromone composition is 4 to 97 parts by weight, relative to 100 weight by parts of (1R,3R)-(3-isopropenyl-2,2-dimethylcyclobutyl)methyl acetate.

A content of (R)-(3-isopropylidene-2,2-dimethylcyclobutyl)methyl acetate in the pheromone composition is 0.1 to 97 parts by weight, relative to 100 weight by parts of (1R,3R)-(3-isopropenyl-2,2-dimethylcyclobutyl)methyl acetate.

A content of (S)-(3-isopropylidene-2,2-dimethylcyclobutyl)methyl acetate in the pheromone composition is 0.1 to 97 parts by weight, relative to 100 weight by parts of (1R,3R)-(3-isopropenyl-2,2-dimethylcyclobutyl)methyl acetate.

Further, the sex pheromone composition may comprise additives such as stabilizers, such as 2,6-di-tert-butyl-4-methylphenol (BHT); antioxidants such as butylhydroxytoluene, butylhydroxyanisole, hydroquinone, and vitamin E; and/or UV absorbers, for example, 2-hydroxy-4-octoxybenzophenone and 2-(2'-hydroxy-3'-tert-butyl-5'-methylphenyl)-5-chlorobenzotriazole.

The amount of each of the additives in the sex pheromone composition is preferably as follow: 1 to 15 parts by weight of the stabilizer, 1 to 15 parts by weight the antioxidant, 1 to 15 parts by weight of the UV absorber, relative to 100 weight by parts of (1R,3R)-(3-isopropenyl-2,2-dimethylcyclobutyl)methyl acetate.

Next, the attractant for *Planococcus citri* will be described hereinafter, which 6 attractant at least comprises the sex pheromone composition and a carrier which releasably carries the sex pheromone in the sex pheromone composition.

The carrier is not particularly limited as long as it stably holds the sex pheromone composition and releases at least the sex pheromone for a certain period of time, a such as septum, a cap, and a mineral.

The carrier sustained-releases the sex pheromone, and is preferably made of a polymer.

The polymer is not particularly limited as long as it allows the sex pheromone to permeate and released outside of the polymer membrane in an appropriate rate. Examples of a polymer include natural rubbers such as a cis-polyisoprene; synthetic rubbers such as isoprene rubber and butadiene rubber; polyolefins such as polyethylene and polypropylene; copolymers containing at least 80% by weight of ethylene such as ethylene-vinyl acetate copolymer and ethylene-acrylate copolymer; biodegradable polyesters; and polyvinyl chloride.

The amount loaded on the carrier varies depending on a manner of application and an amount applied, but is preferably 10 g to 1000 mg, more preferably 10 μg to 100 mg, per formulation.

The attractant having at least the carrier may be produced by a known technique such as kneading or impregnating into the carrier.

Next, a method for attracting *Planococcus citri* will be described hereinafter. The method comprises a step of placing the attractant in a field and allowing the active sex pheromone substance released.

The placement of the attractant in a field is not particularly limited. For example, the density of the attractant in the field is preferably 0.1 to 100 sites per ha, more preferably 1 to 50 sites per ha.

The release period of the sex pheromone for *Planococcus citri* in the field is not particularly limited as long as it allows attraction of the pest.

The amount released at one release cite varies, depending on the field environment and weather conditions, and is not generally specified, but is preferably 0.01 to 100 μg/day/ha.

Examples of a method to control *Planococcus citri* with the attraction include a mass trapping method, a lure & kill- or attract & kill-method, a lure & infect- or attract & infect-method.

EXAMPLES

The present invention will be further described with reference to the following Examples. It should be understood that the present invention is not limited to or by the Examples.

A sample for measuring the spectrum was obtained by purifying a crude product in some cases.

A crude yield refers to a yield of a crude product without being purified.

Example 1

Preparation of 3-(1-ethoxyethoxy)methyl-2,2-dimethylcyclobutanone

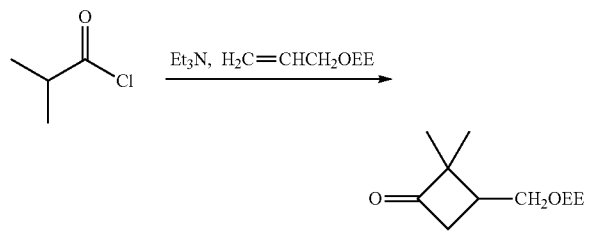

3-(1-Ethoxyethoxy)-1-propene (1761 g, 13.53 mol) and triethylamine (301.3 g, 2.978 mol) were placed in a reactor in a nitrogen atmosphere and stirred at 100° C. Isobutyryl chloride (288.4 g, 2.707 mol) was added dropwise in a portion of 48.07 g every 6 hours at an internal temperature in the reactor of 110° C. or below. After the completion of the dropwise addition, the mixture was stirred at 100° C. for 10 hours. Subsequently, water was added to the reaction mixture. The organic layer was separated and subjected to post-treatment by ordinary washing, drying and concentration. Then, the obtained concentrated liquid was subjected to distillation at a reduced pressure to obtain the target compound, 3-(1-ethoxyethoxy)methyl-2,2-dimethylcyclobutanone (280.8 g, 1.402 mol) in a yield of 52%.

The following is spectrum data of 3-(1-ethoxyethoxy)methyl-2,2-dimethylcyclobutanone (colorless or pale yellow oily liquid) thus produced.

IR (D-ATR): νmax=2973, 2932, 2871, 1779, 1463, 1446, 1380, 1341, 1268, 1133, 1087, 1062, 986, 946, 869 cm $^1$H-NMR (500 MHz CDCl$_3$): δ=1.11 (1.5H, s), 1.12 (1.5H, s), 1.19 (3H, t, J 7.1 Hz), 1.210 (1.5H, s), 1.211 (1.5H, s), 1.29 (3H, d, J=5.4 Hz), 2.27-2.34 (1H, m), 2.74 (0.5H, dd, J=1.4, 17.6 Hz), 2.75 (0.5H, dd, J=1.3, 17.6 Hz), 3.10 (0.5H, dd, J=2.9, 17.6 Hz), 3.12 (0.5H, dd, J=3.0, 17.6 Hz), 3.42-3.76 (4H, m), 4.66-4.70 (1H, m) ppm $^{13}$C-NMR (150 MHz, CDCl$_3$): δ=15.23, 15.25, 16.69, 16.72, 19.64, 19.70, 23.99, 24.03, 35.62, 35.65, 45.77, 60.67, 60.74, 60.93, 65.08, 65.55, 99.58, 99.75, 214.27, 214.29 ppm

Example 2

Preparation of 3-(1-allyloxyethoxy)methyl-2,2-dimethylcyclobutanone

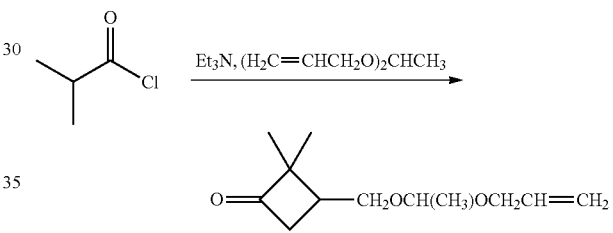

3-(1-Allyloxyethoxy)-1-propene (757.8 g, 5.329 mol) and triethylamine (255.8 g, 2.528 mol) were placed in a reactor in a nitrogen atmosphere and stirred at 100° C. Isobutyryl chloride (224.4 g, 2.106 mol) was added dropwise in a portion of 74.80 g every 10 hours at an internal temperature in the reactor of 110° C. or below. After the completion of the dropwise addition, the mixture was stirred at 100° C. for 12 hours. Subsequently, water was added to the reaction mixture. The organic layer was separated and subjected to post-treatment by ordinary washing, drying and concentration. Then, the obtained concentrated liquid was subjected to distillation at a reduced pressure to obtain the target compound, 3-(1-allyloxyethoxy)methyl-2,2-dimethylcyclobutanone, (228.0 g, 1.074 mol) in a yield of 51%.

The following is spectrum data of 3-(1-allyloxyethoxy)methyl-2,2-dimethylcyclobutanone (colorless or pale yellow oily liquid) thus produced.

IR (D-ATR): νmax=3081, 2963, 2930, 2869, 1779, 1647, 1463, 1383, 1344, 1267, 1132, 1098, 1066, 1040, 993, 923 cm$^{-1}$ $^1$H-NMR (500 MHz CDCl$_3$): δ=1.11 (1.5H, s), 1.12 (1.5H, s), 1.212 (1.5H, s), 1.214 (1.5H, s), 1.31 (3H, d, J=5.4 Hz), 2.28-2.34 (1H, m), 2.75 (0.5H, dd, J=1.5, 17.6 Hz), 2.76 (0.5H, dd; J=1.5, 17.6 Hz), 3.10 (0.5H, dd, J=3.0, 17.6 Hz), 3.12 (0.5H, dd, J=3.3, 17.6 Hz), 3.51 (0.5H, dd, =6.7, 9.8 Hz), 3.56 (0.5H, dd, J=7.5, 9.8 Hz), 3.69 (0.5H, dd, J=6.8, 9.8 Hz), 3.74 (0.5H, dd, J=7.6, 9.8 Hz), 3.96-4.00 (1H, m), 4.06-4.11 (1H, m), 472-4.76 (1H, m), 5.13-5.17 (1H, m), 5.24-5.29 (1H, m), 5.85-5.93 (1H, m) ppm $^{13}$C-NMR (150 MHz, CDCl$_3$): δ=16.72, 16.74, 19.53, 19.60, 23.98, 24.01, 35.60, 35.62, 45.76, 60.68, 65.04, 65.49, 66.09, 66.26, 99.21, 99.40, 116.65, 134.53, 134.55, 214.20, 214.22 ppm Example 3

Preparation of 2,2-dimethyl-3-(tetrahydropyran-2-yloxymethyl)cyclobutanone

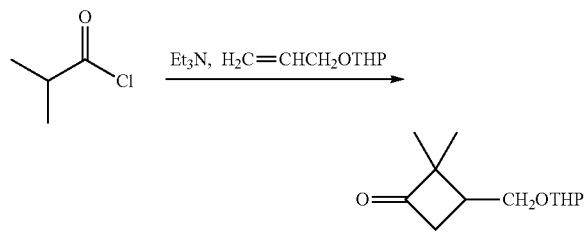

3-(Tetrahydropyran-2-yloxy)-1-propene (644.4 g, 4.486 mol) and triethylamine (215.3 g, 2.128 mol) were placed in a reactor in a nitrogen atmosphere and stirred at 100° C. Isobutyryl chloride (188.9 g, 1.773 mol) was added dropwise in a portion of 62.97 g every 8 hours at an internal temperature in the reactor of 110° C. or below. After the completion of the dropwise addition, the mixture was stirred at 100° C. for 10 hours. Subsequently, water was added to the reaction mixture. The organic layer was separated and subjected to post-treatment by ordinary washing, drying and concentration. Then, the obtained concentrated liquid was subjected to distillation at a reduced pressure to obtain the target compound, 2,2-dimethyl-3-(tetrahydropyran-2-yloxymethyl)cyclobutanone, (138.8 g, 0.6539 mol) in a yield of 37%.

The following is spectrum data of 2,2-dimethyl-3-(tetrahydropyran-2-yloxymethyl)cyclobutanone (colorless or pale yellow oily liquid) thus produced.

$^1$H-NMR (500 MHz CDCl$_3$): δ=1.12 (1.5H, s), 1.14 (1.5H, s), 1.212 (1.5H, s), 1.214 (1.5H, s), 1.46-1.64 (4H, m), 1.65-1.72 (1H, m), 1.72-1.84 (1H, m), 2.30-2.38 (1H, m), 2.77 (0.5H, dd, J=6.9, 17.6 Hz), 2.80 (0.5H, dd, J=6.9, 17.6 Hz), 3.10 (0.5H, dd, J)=1.6, 17.6 Hz), 3.12 (0.5H, dd, J=1.6, 17.6 Hz), 3.44-3.54 (2H, m), 3.79-3.85 (1H, m), 3.87 (0.5H, dd, J=6.7, 10.3 Hz), 3.93 (0.5H, dd, J=7.2, 10.3 Hz), 4.57-4.62 (1H, m) ppm Example 4

Preparation of 3-allyloxymethyl-2,2-dimethylcyclobutanone

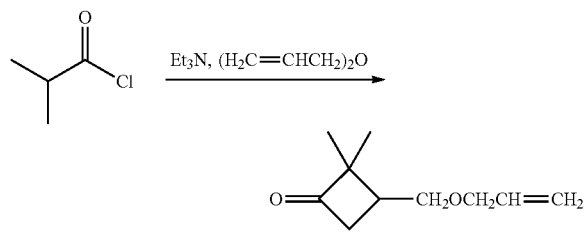

Diallyl ether (405.9 g, 4.136 mol) and triethylamine (90.72 g, 0.8966 mol) were placed in a reactor in a nitrogen atmosphere and stirred at 95° C. Isobutyryl chloride (86.85 g, 0.8151 mol) was added dropwise in a portion of 28.95 g every 6 hours at an internal temperature in the reactor of 100° C. or below. After the completion of the dropwise addition, the mixture was stirred at 95° C. for 10 hours. Subsequently, water was added to the reaction mixture. The organic layer was separated and subjected to post-treatment by ordinary washing, drying and concentration. Then, the obtained concentrated liquid was subjected to distillation at a reduced pressure to obtain the target compound, 3-allyloxymethyl-2,2-dimethylcyclobutanone, (53.55 g, 0.3183 mol) in a yield of 39%.

The following is spectrum data of 3-allyloxymethyl-2,2-dimethylcyclobutanone (colorless or pale yellow oily liquid) thus produced.

IR (D-ATR): νmax=3534, 3081, 2963, 2929, 2866, 1779, 1647, 1463, 1400, 1381, 1363, 1328, 1264, 1090, 1066, 994, 926, 561 cm$^{-1}$.

$^1$H-NMR (500 MHz CDCl$_3$): δ=1.12 (3H, s), 1.21 (3H, s), 2.30-2.37 (1H, m), 2.75 (1H, dd, J=6.8, 17.6 Hz), 3.10 (1H, dd, J=9.2, 17.6 Hz), 3.52 (1H, dd, J=6.5, 9.6 Hz), 3.58 (1H, dd, J=7.6, 9.6 Hz), 3.93-4.01 (2H, m), 5.15-5.19 (1H, m), 5.23-5.28 (1H, m), 5.84-5.93 (1H, m) ppm $^{13}$C-NMR (150 MHz, CDCl$_3$): δ=16.65, 23.99, 35.60, 45.60, 60.78, 70.43, 72.01, 116.98, 134.56, 214.27 ppm Example 5

Preparation of ethyl 2-(3-benzyloxymethyl-2,2-dimethylcyclobutylidene)propanoate

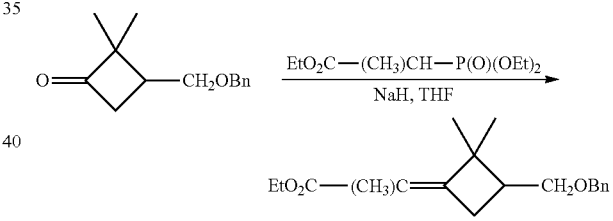

Sodium hydride (1.38 g, 57.4 mmol) and tetrahydrofuran (THF) (140 g) were placed in a reactor in a nitrogen atmosphere and stirred at 25° C. to prepare a suspension. A solution of triethyl 2-phosphonopropionate (13.7 g, 57.4 mmol) in THF (10 g) was added dropwise to the suspension at an internal temperature in the reactor of 35° C. or below. After the completion of the dropwise addition, the mixture was stirred at 55° C. for 1 hour. Then, a solution of 3-benzyloxymethyl-2,2-dimethylcyclobutanone (10.9 g, 49.9 mmol) in THF (30 g) was added dropwise at an internal temperature in the reactor of 60° C. or below and the mixture was refluxed with stirring for 10 hours. Subsequently, water was added to the reaction mixture. The organic layer was separated and subjected to post-treatment by ordinary washing, drying and concentration. Then, the obtained concentrated liquid was purified by silica gel column chromatography (hexane:ethyl acetate=40:1) to obtain the target compound, ethyl 2-(3-benzyloxymethyl-2,2-dimethylcyclobutylidene)propanoate, as a geometric isomer mixture at E:Z=30:70, (12.2 g, 40.4 mmol) in a yield of 81%.

The following is spectrum data of ethyl 2-(3-benzyloxymethyl-2,2-dimethylcyclobutylidene)propanoate (colorless or pale yellow oily liquid) thus produced.

$^1$H-NMR (500 MHz CDCl$_3$): δ=1.22-1.35 (9H, m), 1.67-1.69, 1.77-1.80 (3H, m), 2.27-3.16 (3H, m), 3.45-3.50 (1H, m), 3.57-3.65 (1H, m), 4.10-4.25 (2H, m), 4.47-4.44 (2H, m), 7.26-7.38 (5H, m) ppm Example 6

Preparation of Ethyl 2-(3-methoxymethoxymethyl-2,2-dimethylcyclobutylidene)propanoate

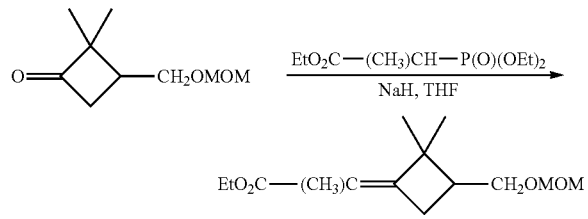

Sodium hydride (386 mg, 16.1 mmol) and tetrahydrofuran (THF) (70 g) were placed in a reactor in a nitrogen atmosphere and stirred at 25° C. to prepare a suspension. A solution of triethyl 2-phosphonopropionate (3.84 g, 16.1 mmol) in THF (9 g) was added dropwise to the suspension at an internal temperature in the reactor of 30° C. or below. After the completion of the dropwise addition, the mixture was stirred at 55° C. for 1 hour. Then a solution of 3-methoxymethoxymethyl-2,2-dimethylcyclobutanone (2.63 g, 15.3 mmol) in THF (30 g) was added dropwise at an internal temperature in the reactor of 60° C. or below. After the completion of the dropwise addition, the mixture was refluxed with stirring for 7 hours. Subsequently, water was added to the reaction mixture. The organic layer was separated and subjected to post-treatment by ordinary washing, drying and concentration. Then, the obtained concentrated liquid was purified by silica gel column chromatography (hexane:ethyl acetate=20:1) to obtain the target compound, ethyl 2-(3-methoxymethoxymethyl-2,2-dimethylcyclobutylidene)propanoate, as a geometric isomer mixture at E:Z=30:70, (2.55 g, 9.95 mmol) in a yield of 65%.

The following is spectrum data of ethyl 2-(3-methoxymethoxymethyl-2,2-dimethylcyclobutylidene)propanoate (colorless or pale yellow oily liquid) thus produced.

$^1$H-NMR (500 MHz CDCl$_3$): δ=1.20-1.33 (9H, m), 1.67, 1.78 (3H, t, J=1.1 Hz, t, J=2.1 Hz), 2.21-2.38 (2H, m), 2.58-2.65, 2.73-2.80 (1H, m), 3.36 (3H, s), 3.47-3.58 (1H, m), 3.63-3.76 (1H, m), 4.11-4.23 (2H, m), 4.60, 4.68 (2H, m) ppm Example 7

Preparation of Ethyl 2-[2,2-dimethyl-3-(tetrahydropyran-2-yloxymethyl)cyclobutylidene]propanoate

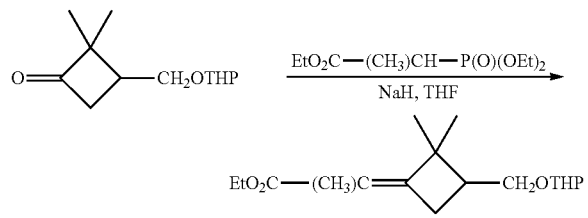

Sodium hydride (10.7 g, 449 mmol) and tetrahydrofuran (THF) (1500 g) were placed in a reactor in a nitrogen atmosphere and stirred at 25° C. to prepare a suspension. Triethyl 2-phosphonopropionate (107 g, 449 mmol) was added dropwise to the suspension at an internal temperature in the reactor of 30° C. or below. After the completion of the dropwise addition, the mixture was stirred at 55° C. for 1 hour. Then, 2,2-dimethyl-3-(tetrahydropyran-2-yloxymethyl)cyclobutanone (90.9 g, 428 mmol) was added dropwise at an internal temperature in the reactor of 60° C. or below. After the completion of the dropwise addition, the mixture was refluxed with stirring for 9 hours. Subsequently, water was added to the reaction mixture. The organic layer was separated and subjected to post-treatment by ordinary washing, drying and concentration. Then, the obtained concentrated liquid was subjected to distillation at a reduced pressure to obtain the target compound, ethyl 2-[2,2-dimethyl-3-(tetrahydropyran-2-yloxymethyl)cyclobutylidene]propanoate, as a diastereomer mixture (80.0 g, 270 mmol) in a yield of 63%.

The following is spectrum data of ethyl 2-[2,2-dimethyl-3-(tetrahydropyran-2-yloxymethyl)cyclobutylidene]propanoate (colorless or pale yellow oily liquid) thus produced.

$^1$H-NMR (500 MHz CDCl$_3$): δ=1.20-1.35 (9H, m), 1.45-1.92 (9H, m), 2.22-2.38, 2.59-2.66, 2.72-2.80, 3.06-3.14, 3.34-3.40, 3.44-3.54, 3.74-3.80, 3.82-3.91, 4.10-4.20, 4.55-4.59, 4.93-4.96 (10H, m) ppm Example 8

Preparation of Ethyl 2-(3-hydroxymethyl-2,2-dimethylcyclobutylidene)propanoate

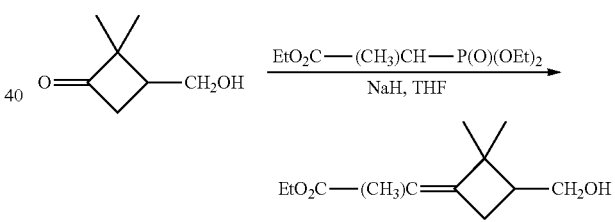

Sodium hydride (996 mg, 41.5 mmol) and tetrahydrofuran (THF) (50 g) were placed in a reactor in a nitrogen atmosphere and stirred at 10° C. to prepare a suspension. A solution of triethyl 2-phosphonopropionate (9.89 g, 41.5 mmol) in THF (10 g) was added dropwise to the suspension at an internal temperature in the reactor of 20° C. or below. After the completion of the dropwise addition, the mixture was stirred at 55° C. for 1 hour. Then, a solution of 3-hydroxymethyl-2,2-dimethylcyclobutanone (2.47 g, 19.3 mmol) in THF (10 g) was added dropwise at an internal temperature in the reactor of 60° C. or below. After the completion of the dropwise addition, the mixture was refluxed with stirring for 9 hours. Subsequently, water was added to the reaction mixture. The organic layer was separated and subjected to post-treatment by ordinary washing, drying and concentration. Then, the obtained concentrated liquid was purified by silica gel column chromatography (hexane:ethyl acetate=10:1) to obtain the target compound, ethyl 2-(3-hydroxymethyl-2,2-dimethylcyclobutylidene)propanoate, as a geometric isomer mixture at 50:50, (2.05 g, 9.65 mmol) in a yield of 50%.

The following is spectrum data of ethyl 2-(3-hydroxymethyl-2,2-dimethylcyclobutylidene)propanoate (colorless or pale yellow oily liquid) thus produced.

IR (D-ATR): νmax=3433, 2958, 2928, 2869, 1702, 1448, 1417, 1366, 1304, 1281, 1254, 1148, 1096, 1065, 1039, 905, 864, 772 cm$^{-1}$ $^1$H-NMR (500 MHz CDCl$_3$): δ=1.23-1.31 (9H, m), 1.32 (3H, s), 1.33 (3H, s), 1.67, 1.77 (3H, t, J=1.5 Hz, t, J=2.1 Hz), 1.72 (1H, brs), 2.13-2.22 (1H, m), 2.28-2.34, 2.56-2.63 (1H, m), 2.71-2.78, 3.04-3.12 (1H, m), 3.61-3.68 (1H, m), 3.75-3.82 (1H, m), 4.07-4.21 (2H, m) ppm

Example 9

Preparation of Ethyl 2-(3-acetoxymethyl-2,2-dimethylcyclobutylidene)propanoate

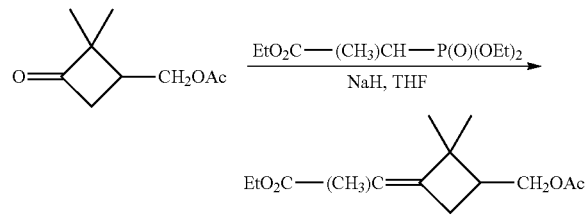

Sodium hydride (224 mg, 9.33 mmol) and tetrahydrofuran (THF) (30 g) were placed in a reactor in a nitrogen atmosphere and stirred at 20° C. to prepare a suspension. A solution of triethyl 2-phosphonopropionate (2.22 g, 9.33 mmol) in THF (6 g) was added dropwise to the suspension at an internal temperature in the reactor of 30° C. or below. After the completion of the dropwise addition, the mixture was stirred at 55° C. for 1 hour. Then, a solution of (2,2-dimethyl-3-oxocyclobutyl)methyl acetate (1.38 g, 8.11 mmol) in THF (8 g) was added dropwise at an internal temperature in the reactor of 60° C. or below. After the completion of the dropwise addition, the mixture was refluxed with stirring for 7 hours. Subsequently, water was added to the reaction mixture. The organic layer was separated and subjected to post-treatment by ordinary washing, drying and concentration. Then, the obtained concentrated liquid was purified by silica gel column chromatography (hexane:ethyl acetate=6:1) to obtain the target compound, ethyl 2-(3-acetoxymethyl-2,2-dimethylcyclobutylidene)propanoate, as a geometric isomer mixture at 50:50, (654 mg, 2.57 mmol) in a yield of 32%.

The following is spectrum data of ethyl 2-(3-acetoxymethyl-2,2-dimethylcyclobutylidene)propanoate (one geometric isomer) (colorless or pale yellow oily liquid) thus produced.

$^1$H-NMR (500 MHz CDCl$_3$): δ=1.10 (3H, s), 1.25 (3H, s), 1.28 (3H, t, J=7.1 Hz), 1.84-1.86 (3H, m), 1.92-1.94 (3H, m), 2.19-2.23 (2H, m), 2.32-2.40 (1H, m), 3.86 (1H, t, J=9.4 Hz), 4.17 (2H, q, J=7.1 Hz), 4.26 (1H, dd, J=7.3, 9.2 Hz) ppm $^{13}$C-NMR (150 MHz, CDCl$_3$): δ=14.17, 15.62, 18.22, 20.91, 23.31, 32.72, 41.46, 44.52, 60.29, 69.28, 125.29, 140.83, 169.34, 181.76 ppm The following is spectrum data of ethyl 2-(3-acetoxymethyl-2,2-dimethylcyclobutylidene)propanoate (another geometric isomer)(colorless or pale yellow oily liquid) thus produced.

$^1$H-NMR (500 MHz CDCl$_3$): δ=1.07 (3H, s), 1.23 (3H, s), 1.27 (3H, t, J=7.1 Hz), 1.76-1.78 (3H, m), 1.84 (3H, brs), 2.27-2.31 (1H, m), 2.33-2.40 (1H, m), 2.69 (1H, dd, J=10.9, 12.8 Hz), 4.03 (1H, t, J=9.8 Hz), 4.13-4.19 (3H, m) ppm $^{13}$C-NMR (150 MHz, CDCl$_3$): δ=14.23, 15.97, 18.11, 20.18, 23.20, 32.65, 41.44, 44.81, 60.29, 69.43, 125.54, 141.95, 168.99, 182.26 ppm

Example 10

Preparation of Ethyl 2-[3-(1-ethoxyethoxy)methyl-2,2-dimethylcyclobutylidene]propanoate

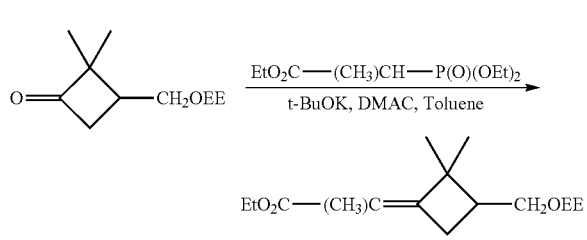

Potassium t-butoxide (120 g, 1.07 mol), toluene (1420 g) and N,N-dimethylacetamide (DMAC) (710 g) were placed in a reactor in a nitrogen atmosphere and stirred at 20° C. Triethyl 2-phosphonopropionate (255 g, 1.07 mol) was added dropwise at an internal temperature in the reactor of 30° C. or below. After the completion of the dropwise addition, the mixture was stirred at 75° C. for 1 hour. Then, 3-(1-ethoxyethoxy)methyl-2,2-dimethylcyclobutanone (164 g, 819 mmol) was added dropwise at an internal temperature in the reactor of 80° C. or below. After the completion of the dropwise addition, the mixture was stirred at 75° C. for 18 hours. Subsequently, brine was added to the reaction mixture. The organic layer was separated and subjected to post-treatment by ordinary washing, drying and concentration. Then, the obtained concentrated liquid was subjected to distillation at a reduced pressure to obtain the target compound, ethyl 2-[3-(1-ethoxyethoxy)methyl-2,2-dimethylcyclobutylidene]propanoate, as a geometric isomer mixture at E:Z=70:30, (182 g, 639 mmol) in a yield of 78%.

The following is spectrum data of ethyl 2-[3-(1-ethoxyethoxy)methyl-2,2-dimethylcyclobutylidene]propanoate (colorless or pale yellow oily liquid) thus produced.

IR (D-ATR): νmax=2977, 2930, 2870, 1780, 1704, 1669, 1460, 1381, 1366, 1304, 1281, 1254, 1137, 1097, 1059, 1043, 982, 947, 930, 874, 766 cm-1

$^1$H-NMR (500 MHz CDCl$_3$): δ=1.17-1.34 (15H, m), 1.67 (0.9H, t, J=1.5 Hz), 1.77 (2.1H, t, J=1.9 Hz), 2.11-2.34 (1.3H, m), 2.54-2.70 (0.7H, m), 2.72-2.79 (0.3H, m), 3.00-3.13 (0.7H, m), 3.37-3.70 (4H, m), 4.00-4.22 (2H, m), 4.63-4.69 (1H, m) ppm

Example 11

Preparation of 2-(3-benzyloxymethyl-2,2-dimethylcyclobutylidene)propan-1-ol

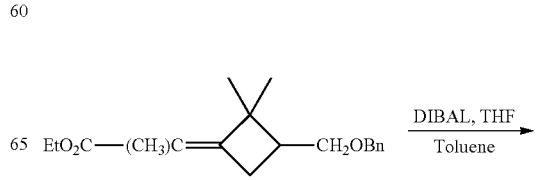

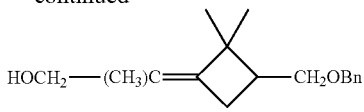

A 1.00 M solution of diisobutylaluminum hydride (DIBAL)(120 ml, 120 mmol) in toluene solution and tetrahydrofuran (THF) (322 g) were placed in a reactor in a nitrogen atmosphere and stirred at −60° C. The geometric isomer mixture of E:Z=30:70 of ethyl 2-(3-benzyloxymethyl-2,2-dimethylcyclobutylidene)propanoate (12.2 g, 40.2 mmol) obtained in Example 5 was added dropwise at an internal temperature in the reactor of −50° C. or below. After the completion of the dropwise addition, the mixture was stirred for 3 hours while heating gradually up to 10° C. Subsequently, an aqueous solution of a saturated Rochelle salt was added to the mixture. The organic layer was separated and subjected to post-treatment by ordinary washing, drying and concentration. Then, the obtained concentrated liquid was purified by silica gel column chromatography (hexane:ethyl acetate=4:1) to obtain the target compound, 2-(3-benzyloxymethyl-2,2-dimethylcyclobutylidene)propan-1-ol, as a geometric isomer mixture at E:Z=30:70, (9.30 g, 35.7 mmol) in a yield of 89%.

The following is spectrum data of 2-(3-benzyloxymethyl-2,2-dimethylcyclobutylidene)propan-1-ol (colorless or pale yellow oily liquid) thus produced.

$^1$H-NMR (500 MHz CDCl$_3$): δ=1.17 (3H, s), 1.29, 1.30 (3H, s), 1.48 (1H, brs), 1.56-1.58, 1.67-1.69 (3H, m), 2.15-2.38 (2H, m), 2.60-2.75 (1H, m), 3.40-3.50 (1H, m), 3.58 (1H, dd, J=8.0, 9.6 Hz), 3.90, 4.01 (1H, d, J=11.4 Hz, d, J 11.5 Hz), 3.92, 4.05 (1H, d, J=11.4 Hz, d, J=11.5 Hz), 4.43-4.53 (2H, m), 7.26-7.38 (5H, m) ppm

Example 12

Preparation of 2-(3-methoxymethoxymethyl-2,2-dimethylcyclobutylidene)propan-1-ol

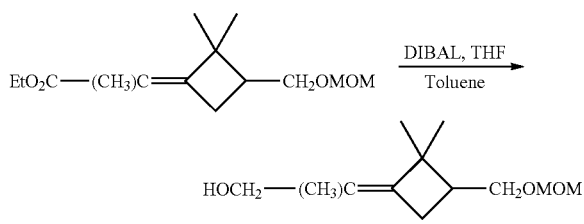

A 1.00 M solution of Diisobutylaluminum hydride (DIBAL) (40.0 ml, 40.0 mmol) in toluene and tetrahydrofuran (THF) (150 g) were placed in a reactor in a nitrogen atmosphere and stirred at −60° C. The geometric isomer mixture of E:Z=30:70 of ethyl 2-[2,2-dimethyl-3-(tetrahydropyran-2-yloxymethyl)cyclobutylidene]propanoate obtained in Example 6 was added dropwise at an internal temperature in the reactor of −50° C. or below. After the completion of the dropwise addition, the mixture was stirred for 3 hours while heating gradually up to 10° C. Subsequently, an aqueous solution of a saturated Rochelle salt was added to the mixture. The organic layer was separated and subjected to post-treatment by ordinary washing, drying and concentration. Then, the obtained concentrated liquid was purified by silica gel column chromatography (hexane:ethyl acetate=3:1) to obtain the target compound, 2-(3-methoxymethoxymethyl-2,2-dimethylcyclobutylidene)propan-1-ol, as a geometric isomer mixture at E:Z=30:70, (2.02 g, 9.43 mmol) in a yield of 96%.

The following is spectrum data of 2-(3-methoxymethoxymethyl-2,2-dimethylcyclobutylidene)propan-1-ol (colorless or pale yellow oily liquid) thus produced.

$^1$H-NMR (500 MHz CDCl$_3$): δ=1.16 (3H, s), 1.27 (3H, s), 1.51 (1H, brs), 1.55-1.56, 1.65-1.67 (3H, m), 2.14-2.25 (2H, m), 2.59-2.72 (1H, m), 3.35 (3H, s), 3.45-3.57 (1H, m), 3.61-3.68 (1H, m), 3.90, 4.00 (1 Hz, d, J=3.8 Hz, d, J=8.0 Hz), 4.59, 4.67 (2H, s) ppm

Example 13

Preparation of 2-[2,2-dimethyl-3-(tetrahydropyran-2-yloxymethyl)cyclobutylidene]propan-1-ol

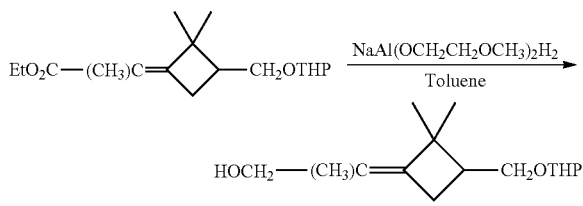

A 3.60 M solution of sodium bis (2-methoxyethoxy) aluminum hydride (120 ml, 432 mmol) in toluene and toluene (122 g) were placed in a reactor in a nitrogen atmosphere and stirred at 0° C. The diastereomer mixture mixture of E:Z=30:70 of ethyl 2-[2,2-dimethyl-3-(tetrahydropyran-2-yloxymethyl)cyclobutylidene]propanoate (71.4 g, 241 mmol) obtained as in Example 7 was added dropwise at an internal temperature in the reactor of −10° C. or below. After the completion of the dropwise addition, the mixture was stirred for 9 hours while heating gradually up to 26° C. Subsequently, a caustic soda aqueous solution was added to the mixture. The organic layer was separated and subjected to post-treatment by ordinary washing, drying and concentration to obtain a crude product of the target compound, 2-[2,2-dimethyl-3-(tetrahydropyran-2-yloxymethyl)cyclobutylidene]propan-1-ol, as a diastereomer mixture, (50.4 g, 198 mmol) in a yield of 82%.

The following is spectrum data of 2-[2,2-dimethyl-3-(tetrahydropyran-2-yloxymethyl)cyclobutylidene]propan-1-ol (colorless or pale yellow oily liquid) thus produced.

$^1$H-NMR (500 MHz CDCl$_3$): δ=1.15, 1.18, 1.19 (3H, s, s, s), 1.27 (3H, s), 1.40-1.85 (10H, m), 2.09-2.28 (2H, m), 2.58-2.73 (1H, m), 3.32-3.37 (2, m), 3.71-3.78, 3.82-3.93, 3.98-4.60 (4H, m), 4.53-4.59 (4H, m) ppm

Example 14

Preparation of 2-(3-hydroxymethyl-2,2-dimethylcyclobutylidene)propan-1-ol

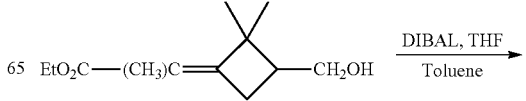

-continued

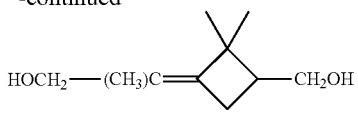

A 1.01 M solution of diisobutylaluminum hydride (DIBAL) (100 ml, 101 mmol) in toluene and tetrahydrofuran (THF, 300 g) were placed in a reactor in a nitrogen atmosphere and stirred at −60° C. The geometric isomer mixture of E:Z=50:50 of ethyl 2-(3-hydroxymethyl-2,2-dimethylcyclobutylidene)propanoate (5.36 g, 25.3 mmol) was added dropwise to the solution at an internal temperature in the reactor of − 50° C. or below. After the completion of the dropwise addition, the mixture was stirred for 8 hours while heating gradually up to 10° C. Subsequently, an aqueous solution of a saturated Rochelle salt was added to the mixture. The organic layer was separated and subjected to post-treatment by ordinary washing, drying and concentration to obtain a crude product of the target compound, 2-(3-hydroxymethyl-2,2-dimethylcyclobutylidene)propan-1-ol, as a geometric isomer mixture at E:Z=50:50, (4.31 g, 25.3 mmol) in a crude yield of 100%.

The following is spectrum data of (E)-2-(3-hydroxymethyl-2,2-dimethylcyclobutylidene)propan-1-ol (colorless or pale yellow oily liquid) thus produced.

IR (D-ATR): vmax=3322, 2955, 2922, 2864, 1703, 1459, 1382, 1361, 1311, 1276, 1224, 1167, 1101, 1053, 1031, 1005, 942, 886 cm$^{-1}$ $^1$H-NMR (500 MHz CDCl$_3$): δ=1.18 (3H, s), 1.28 (3H, s), 1.66 (3H, t, J=1.9 Hz), 1.76 (2H, brs), 2.06-2.13 (1H, m), 2.19-2.26 (1H, m), 2.66-2.72 (1H, m), 3.61 (1H, dd, J=7.2, 10.7 Hz), 3.75 (1H, dd, J=7.6, 10.7 Hz), 3.89 (2H, brs) ppm $^{13}$C-NMR (150 MHz, CDCl$_3$): δ=14.19, 20.51, 27.54, 28.24, 42.71, 44.40, 63.78, 63.88, 125.64, 142.47 ppm The following is spectrum data of (Z)-2-(3-hydroxymethyl-2,2-dimethylcyclobutylidene)propan-1-ol (colorless or pale yellow oily liquid) thus produced.

IR (D-ATR): vmax=3329, 2954, 2925, 2865, 1702, 1445, 1374, 1362, 1312, 1272, 1249, 1166, 1121, 1066, 1026, 1003, 888 cm$^1$ $^1$H-NMR (500 MHz CDCl$_3$): δ=1.18 (3H, s), 1.28 (3H, s), 1.56 (3H, t, J=1.3 Hz), 1.57 (2H, brs), 2.07-2.23 (21-, m), 2.59-2.65 (1H, m), 3.62 (1H, dd, J=6.8, 10.7 Hz), 3.76 (1H, dd, J=7.6, 10.7 Hz), 3.98-4.05 (2H, m) ppm $^{13}$C-NMR (150 MHz, CDCl$_3$): δ=15.07, 21.90, 27.63, 29.56, 42.49, 44.58, 62.51, 63.97, 126.32, 143.79 ppm Example 15

Preparation of 2-(3-hydroxymethyl-2,2-dimethylcyclobutylidene)propan-1-ol

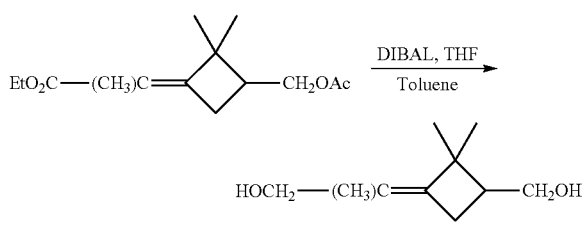

A 1.01 M solution of diisobutylaluminum hydride (DIBAL) (100 ml, 101 mmol) in toluene and tetrahydrofuran (THF, 200 g) were placed in a reactor in a nitrogen atmosphere and stirred at −60° C. The geometric isomer mixture of E:Z=50:50 of ethyl 2-(3-acetoxymethyl-2,2-dimethylcyclobutylidene)propanoate obtained as in Example 9 (4.28 g, 16.8 mmol) was added dropwise at an internal temperature in the reactor of − 50° C. or below. After the completion of the dropwise addition, the mixture was stirred for 8 hours while heating gradually up to 10° C. Subsequently, an aqueous solution of a saturated Rochelle salt was added to the mixture. The organic layer was separated and subjected to post-treatment by ordinary washing, drying and concentration to obtain a crude product of the target compound, 2-(3-hydroxymethyl-2,2-dimethylcyclobutylidene)propan-1-ol, as a geometric isomer mixture at E:Z=50:50, (2.86 g, 16.8 mmol) in a crude yield of 100%. The spectrum data of 2-(3-hydroxymethyl-2,2-dimethylcyclobutylidene)propan-1-ol thus obtained (colorless or pale yellow oily liquid) had the same spectra as in Example 14.

Example 16

Preparation of 2-[3-(1-ethoxyethoxy)methyl-2,2-dimethylcyclobutylidene]propan-1-ol

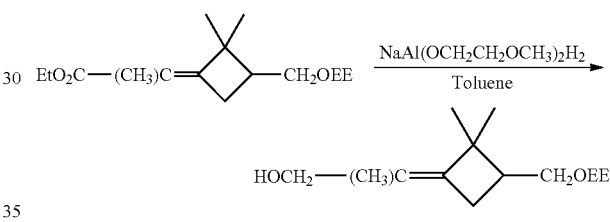

A 3.60 M solution of sodium bis(2-methoxyethoxy)aluminum hydride in toluene (258 ml, 928 mmol) and toluene (534 g) were placed in a reactor in a nitrogen atmosphere and stirred at 20° C. The geometric isomer mixture of E:Z=70:30 of ethyl 2-[3-(I-ethoxyethoxy)methyl-2,2-dimethylcyclobutylidene]propanoate (175 g, 615 mmol) was added dropwise at an internal temperature in the reactor of 30° C. or below. After the completion of the dropwise addition, the mixture was stirred for 4 hours while heating gradually up to 65° C. Subsequently, a caustic soda aqueous solution was added to the mixture. The organic layer was separated and subjected to post-treatment by ordinary washing, drying and concentration to obtain a crude product of the target compound, 2-[3-(1-ethoxyethoxy)methyl-2,2-dimethylcyclobutylidene]propan-1-ol, as a geometric isomer mixture at E:Z=70:30, (149 g, 615 mmol) in a crude yield of 100%.

The following is spectrum data of (E)-2-[3-(1-ethoxyethoxy)methyl-2,2-dimethylcyclobutylidene]propan-1-ol (colorless or pale yellow oily liquid) thus produced.

IR (D-ATR): vmax=3404, 2956, 2923, 2866, 1459, 1445, 1380, 1361, 1342, 1275, 1223, 1133, 1087, 1058, 1001, 945, 930, 875 cm$^{-1}$ $^1$H-NMR (500 MHz CDCl$_3$): δ=1.14-1.24 (6H, m), 1.24-1.35 (6H, m), 1.60 (1H, s), 1.62-1.67 (3H, m), 2.07-2.26 (2H, m), 2.66-2.71 (1H, m), 3.34-3.92 (6H, m), 4.61-4.69 (1H, m) ppm The following is spectrum data of (Z)-2-[3-(1-ethoxyethoxy)methyl-2,2-dimethylcyclobutylidene]propan-1-ol (colorless or pale yellow oily liquid) thus produced.

IR (D-ATR): νmax=3416, 2957, 2926, 2866, 1458, 1445, 1379, 1362, 1342, 1223, 1133, 1087, 1058, 1038, 1002, 930, 875 cm$^{-1}$ $^1$H-NMR (500 MHz CDCl$_3$): δ=1.14-1.24 (6H, m), 1.24-1.34 (6H, m), 1.50 (1H, s), 1.52-1.56 (3H, m), 2.07-2.28 (2H, m), 2.59-2.67 (1H, m), 3.35-4.05 (6H, m), 4.60-4.78 (1H, m) ppm Example 17

Preparation of [3-(2-chloro-1-methylethylidene)-2,2-dimethylcyclobutyl]methoxymethylbenzene

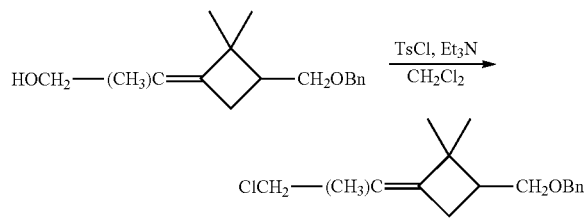

The geometric isomer mixture of E:Z=30:70 of 2-(3-benzyloxymethyl-2,2-dimethylcyclobutylidene)propan-1-ol (1.35 g, 5.17 mmol) obtained in Example 11, methylene chloride (50 g) and triethylamine (1.57 g, 15.5 mmol) were placed in a reactor in a nitrogen atmosphere and stirred at 0° C. Paratoluenesulfonyl chloride (1.18 g, 6.20 mmol) was added to the solution, and the mixture was stirred for 24 hours while heating gradually up to 25° C. Subsequently, water was added to the reaction mixture. The organic layer was separated and subjected to post-treatment by ordinary washing, drying and concentration. Then, the obtained concentrated liquid was purified by silica gel column chromatography (hexane:ethyl acetate=30:1) to obtain the target compound, [3-(2-chloro-1-methylethylidene)-2,2-dimethylcyclobutyl]methoxymethylbenzene, as a geometric isomer mixture at E:Z=30:70, (586 mg, 2.10 mmol) in a yield of 41%.

The following is spectrum data of [3-(2-chloro-1-methylethylidene)-2,2-dimethylcyclobutyl]methoxymethylbenzene (colorless or pale yellow oily liquid) thus produced.

$^1$H-NMR (500 MHz CDCl$_3$): δ=1.21 (3H, s), 1.33 (3H, s), 1.59-1.61 (3H, m), 2.17-2.33 (2H, m), 2.63-2.69 (1H, m), 3.47 (1H, dd, J=6.5, 9.5 Hz), 3.58 (1H, dd, J=8.0, 9.5 Hz), 4.00-40.08 (2H, m), 4.51 (2H, s), 7.26-7.38 (5H, m) ppm Example 18

Preparation of [3-(2-bromo-1-methylethylidene)-2,2-dimethylcyclobutyl]methoxymethylbenzene

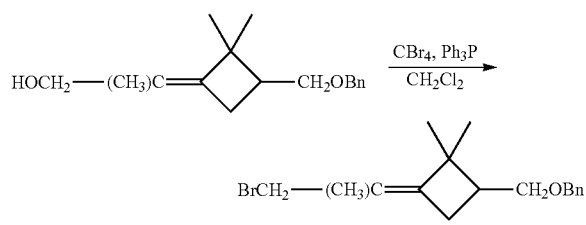

The geometric isomer mixture of E:Z=30:70 of 2-(3-benzyloxymethyl-2,2-dimethylcyclobutylidene)propan-1-ol (469 mg, 1.80 mmol) obtained in Example 11, methylene chloride (30 g) and triphenylphosphine (734 mg, 2.80 mmol) were placed in a reactor in a nitrogen atmosphere and stirred at 0° C. Carbon tetrabromide (929 mg, 2.80 mmol) was added to the mixture, and the mixture was stirred for 15 hours while heating gradually up to 25° C. Subsequently, 3 ml of ethanol was added to the reaction mixture, and then concentrated and the precipitated triphenylphosphine oxide was removed by filtration using hexane. Then, the obtained filtrate was concentrated and purified by silica gel column chromatography (hexane:ethyl acetate=50:1) to obtain the target compound, [3-(2-bromo-1-methylethylidene)-2,2-dimethylcyclobutyl]methoxymethylbenzene, as a geometric isomer mixture at E:Z=30:70, (454 mg, 1.40 mmol) in a yield of 78%.

The following is spectrum data of [3-(2-bromo-1-methylethylidene)-2,2-dimethylcyclobutyl]methoxymethylbenzene (colorless or pale yellow oily liquid) thus produced.

$^1$H-NMR (500 MHz CDCl$_3$): δ==1.17, 1.22 (3H, s, s), 1.28, 1.34 (3H, s, s), 1.61, 1.72 (3H, t, J=1.5 Hz, t, J=1.9 Hz), 2.16-2.33 (2H, m), 2.64, 2.67-2.73 (1H, dd, J=8.8, 16.0 Hz, m), 3.47 (1H, dd, J=6.9, 9.6 Hz), 3.59 (1H, dd, J=8.2, 9.4 Hz), 3.86, 3.99 (2H, s, s), 4.51 (2H, s) ppm Example 19

Preparation of 2-(3-benzyloxymethyl-2,2-dimethylcyclobutylidene)propyl(triphenyl)phosphonium Bromide

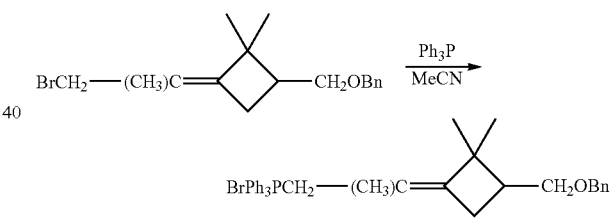

The geometric isomer mixture of E:Z=25:75 of [3-(2-bromo-1-methylethylidene)-2,2-dimethylcyclobutyl]methoxymethylbenzene (220 mg, 0.680 mmol) obtained in Example 18, acetonitrile (8 g) and triphenylphosphine (232 mg, 0.884 mmol) were placed in a reactor in a nitrogen atmosphere and stirred with heating under reflux for 13 hours. The reaction mixture was concentrated at a reduced pressure. Next, toluene (18 g) was added to the concentrated solution, and the operation of concentration at a reduced pressure was repeated twice to obtain a crude product of the target product, 2-(3-benzyloxymethyl-2,2-dimethylcyclobutylidene)propyl(triphenyl)phosphonium bromide as a geometric isomer mixture at E:Z=25:75, (500 mg).

The following is spectrum data of 2-(3-benzyloxymethyl-2,2-dimethylcyclobutylidene)propyl(triphenyl)phosphonium bromide (colorless solid) thus produced.

$^1$H-NMR (500 MHz CD$_3$CN): δ=0.69, 1.06 (3H, s, s), 0.86, 1.17 (3H, s, s), 1.28-1.31, 1.43-1.46 (3H, m), 2.00-2.25 (2H, m), 2.58-2.67 (1H, m), 3.16, 3.30 (1H, dd, J=6.5, 9.6 Hz, dd, J=6.5, 9.5 Hz), 3.34, 3.38 (1H, dd, J=7.6, 9.6 Hz, dd, J=8.0, 9.6 Hz), 4.36, 4.39 (2H, s, s), 7.20-7.80 (20H, m) ppm

Example 20

Preparation of 2-(3-methoxymethoxymethyl-2,2-dimethylcyclobutylidene)propyl acetate

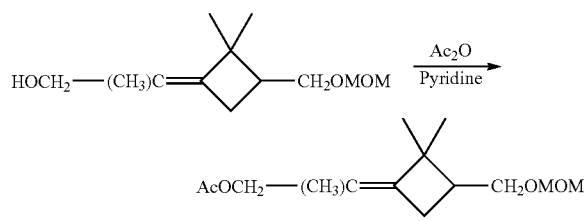

The geometric isomer mixture of E:Z=30:70 of 2-(3-methoxymethoxymethyl-2,2-dimethylcyclobutylidene)propan-1-ol (812 mg, 3.79 mmol) obtained in Example 12 and pyridine (3.0 g, 38 mmol) were placed in a reactor in a nitrogen atmosphere and stirred at 25° C. Then, acetic anhydride (2.00 g, 19.6 mmol) was added dropwise at an internal temperature in the reactor of 30° C. or below. After the completion of the dropwise addition, the mixture was stirred at 25° C. for 4 hours. Subsequently, water was added to the mixture. The organic layer was separated and subjected to post-treatment by ordinary washing, drying and concentration. Then, the obtained concentrated liquid was purified by silica gel column chromatography (hexane:ethyl acetate=20:1) to obtain the target compound, 2-(3-methoxymethoxymethyl-2,2-dimethylcyclobutylidene)propyl acetate, as a geometric isomer mixture at E:Z=30:70, (952 mg, 3.71 mmol) in a yield of 98%.

The following is spectrum data of 2-(3-methoxymethoxymethyl-2,2-dimethylcyclobutylidene)propyl acetate (colorless or pale yellow oily liquid) thus produced.

$^1$H-NMR (500 MHz CDCl$_3$): δ=1.16 (3H, s), 1.27 (3H, s), 1.52, 1.60-1.62 (3H, brs, m), 2.04, 2.05 (3H, s, s)), 2.16-2.25 (2H, m), 2.62-2.73 (1H, m), 3.35 (3H, s), 3.46-3.59 (1H, m), 3.61-3.68 (1H, m), 4.35, 4.48 (2H, brs, brs), 4.59, 4.67 (2H, s, s) ppm

Example 21

Preparation of 2-[2,2-dimethyl-3-(tetrahydropyran-2-yloxymethyl)cyclobutylidene]propyl Acetate

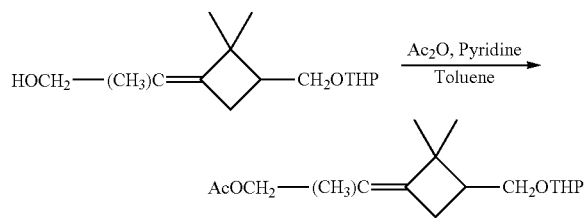

The diastereomer mixture of 2-[2,2-dimethyl-3-(tetrahydropyran-2-yloxymethyl)cyclobutylidene]propan-1-ol obtained in Example 13, pyridine (81 g, 1.0 mol) and toluene (311 g) were placed in a reactor in a nitrogen atmosphere and stirred at 25° C. Then, acetic anhydride (41.6 g, 408 mmol) was added dropwise was added dropwise at an internal temperature in the reactor of 30° C. or below. After the completion of the dropwise addition, the mixture was stirred at 25° C. for 24 hours. Subsequently, water was added to the mixture. The organic layer was separated and subjected to post-treatment by ordinary washing, drying and concentration. The concentrated one was subjected to distillation at a reduced pressure to obtain the target compound, 2-[2,2-dimethyl-3-(tetrahydropyran-2-yloxymethyl)cyclobutylidene]propyl acetate, as a diastereomer mixture (54.5 g, 184 mmol) in a yield of 94%.

The following is spectrum data of 2-[2,2-dimethyl-3-(tetrahydropyan-2-yloxymethyl)cyclobutylidene]propyl acetate (colorless or pale yellow oily liquid) thus produced.

$^1$H-NMR (500 MHz CDCl$_3$): δ=1.14-1.19 (3H, m), 1.24-1.29 (3H, m), 1.44-1.59 (6H, m), 1.60-1.62 (1H, m), 1.63-1.71 (1H, m), 1.74-1.83 (1H, m), 2.00-2.06 (3H, m), 2.15-2.29 (2H, m), 2.60-2.73 (1H, m), 3.31-3.37, 3.42-3.51 (2H, m), 3.71-3.77, 3.81-3.87 (2H, m), 4.32-4.38, 4.47-4.48 (2H, m), 4.52-4.58 (1H, m) ppm

Example 22

Preparation of 2-(3-hydroxymethyl-2,2-dimethylcyclobutylidene)propan-1-ol

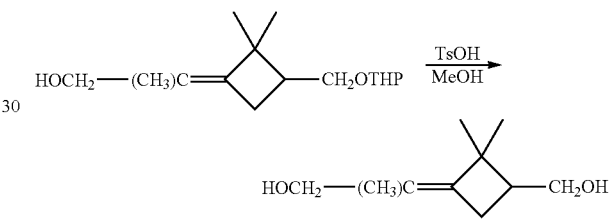

The diastereomer mixture of 2-[2,2-dimethyl-3-(tetrahydropyran-2-yloxymethyl)cyclobutylidene]propan-1-ol (45.0 g, 177 mmol) obtained in Example 13, p-toluenesulfonic acid (189 mg, 0.0011 mmol) and methanol (1100 g) were placed in a reactor in a nitrogen atmosphere and stirred at 20° C. or 24 hours. Subsequently, sodium bicarbonate (200 mg) was added to the reaction mixture, and the mixture was concentrated to obtain a crude product of the target compound, 2-(3-hydroxymethyl-2,2-dimethylcyclobutylidene) propan-1-ol, as a geometric isomer mixture (30.1 g, 177 mmol) in a crude yield of 100%. The spectrum data of 2-(3-hydroxymethyl-2,2-dimethylcyclobutylidene)propan-1-ol thus obtained (colorless or pale yellow oily liquid) had the same spectra as in Example 14.

Example 23

Preparation of 2-(3-hydroxymethyl-2,2-dimethylcyclobutylidene)propan-1-ol

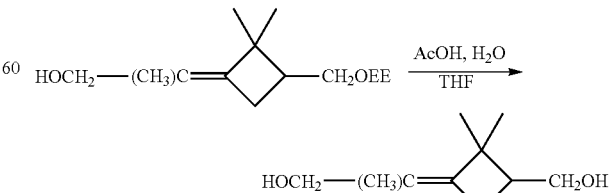

The crude product of the geometrical isomer of E:Z=70:30 of 2-[3-(1-ethoxyethoxy)methyl-2,2-dimethylcyclobutylidene]propan-1-ol (149 g, 615 mmol) obtained in Example 16, tetrahydrofuran (THF) (306 g), acetic acid (34 g), and water (102 g) were placed in a reactor in a nitrogen atmosphere and stirred at 20° C. Subsequently, the mixture was heated up to 75° C. while reducing a pressure so as to maintain mild reflux to distill off low-boiling components. After the completion of the distillation, brine was added to the reaction mixture. The organic layer was separated and subjected to post-treatment by ordinary washing, drying and concentration to obtain a crude product of the target compound, 2-(3-hydroxymethyl-2,2-dimethylcyclobutylidene)propan-1-ol, as a geometric isomer mixture at E:Z=70:30, (105 g, 615 mmol) in a crude yield of 100%. The spectrum data of 2-(3-hydroxymethyl-2,2-dimethylcyclobutylidene)propan-1-ol thus obtained (colorless or pale yellow oily liquid) had the same spectra as in Example 14.

Example 24

Preparation of [3-(2-acetoxy-1-methylethylidene)-2,2-dimethylcyclobutyl]methyl Acetate

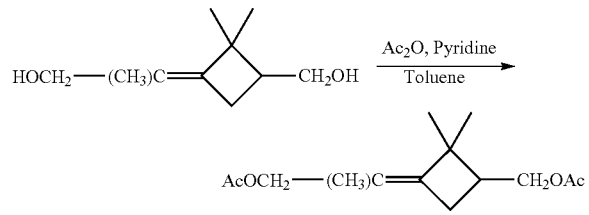

The geometric isomer mixture of E:Z=57:43 of 2-(3-hydroxymethyl-2,2-dimethylcyclobutylidene)propan-1-ol (24.5 g), 0.144 mol) obtained in Example 14, toluene (202 g) and pyridine (114 g, 1.44 mol) were placed in a reactor in a nitrogen atmosphere and stirred at 10° C. Acetic anhydride (73.6 g, 0.721 mol) was added dropwise at an internal temperature in the reactor of 20° C. or below. After the completion of the dropwise addition, the mixture was stirred at 15° C. for 6 hours. Subsequently, water was added to the mixture. The organic layer was separated and subjected to post-treatment by ordinary washing, drying and concentration. Then, the obtained concentrated liquid was subjected to distillation at a reduced pressure to obtain a target product, [3-(2-acetoxy-1-methylethylidene)-2,2-dimethylcyclobutyl]methyl acetate, as a geometric isomer mixture at E:Z=57:43, (30.0 g, 0.118 mol) in a yield of 82%.

The following is spectrum data of [(E)-3-(2-acetoxy-1-methylethylidene)-2,2-dimethylcyclobutyl]methyl acetate (colorless or pale yellow oily liquid) thus produced.

IR (D-ATR): vmax=2958, 1740, 1459, 1380, 1365, 1235, 1171, 1023, 974, 893, 830, 605 cm$^{-1}$ $^1$H-NMR (500 MHz CDCl$_3$): δ=1.16 (3H, s), 1.27 (3H, s), 1.61 (311, t, J=1.9 Hz), 2.02 (3H, s), 2.04 (3H, s)), 2.20-2.29 (2H, m), 2.68-2.75 (1H, m), 4.06-4.14 (2H, m), 4.32 (11, d, J 11.8 Hz), 4.35 (1H, d, J 11.8 Hz) ppm $^{13}$C-NMR (150 MHz, CDCl$_3$): δ=14.51, 20.54, 20.92, 20.95, 27.72, 27.85, 39.05, 44.62, 65.25, 65.31, 121.57, 144.58, 171.06, 171.11 ppm The following is spectrum data of [(Z)-3-(2-acetoxy-1-methylethylidene)-2,2-dimethylcyclobutyl]methyl acetate (colorless or pale yellow oily liquid) thus produced.

IR (D-ATR): vmax=2957, 1741, 1462, 1366, 1236, 1024, 975, 891, 631, 606 cm$^{-1}$ $^1$H-NMR (500 MHz CDCl$_3$): δ=1.15 (3H, s), 1.26 (3H, s), 1.51-1.52 (3H, m), 2.02 (3H, s), 2.04 (3H, s), 2.17-2.27 (2H, m), 2.61-2.69 (1H, m), 4.09 (1H, d, J=5.4 Hz), 4.12 (1H, d, J)=5.4 Hz), 4.47 (2H, brs) ppm $^{13}$C-NMR (150 MHz, CDCl$_3$): δ=15.46, 20.91, 20.94, 21.65, 27.80, 28.82, 38.88, 44.79, 64.06, 65.23, 121.91, 145.70, 171 0.05, 171.14 ppm Example 25

Preparation of (3-[2-(2-methylbutanoyloxy)-1-methylethylidene]-2,2-dimethylcyclobutyl)methyl 2-methylbutanoate

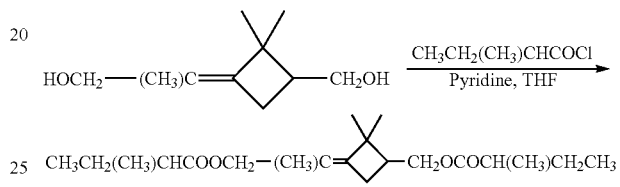

The geometric isomer mixture of E:Z=50:50 of 2-(3-hydroxymethyl-2,2-dimethylcyclobutylidene)propan-1-ol (1.72 g, 10.1 mmol) obtained in Example 14, tetrahydrofuran (THF) (36 g) and pyridine (16 g, 200 mmol) were placed in a reactor in a nitrogen atmosphere and stirred at 0° C. 2-Methylbutanoyl chloride (4.85 g, 40.2 mmol) was added dropwise at an internal temperature in the reactor of 20° C. or below. After the completion of the dropwise addition, the mixture was stirred at 20° C. for 3 hours. Subsequently, water was added to the mixture. The organic layer was separated and subjected to post-treatment by ordinary washing, drying and concentration. Then, the obtained concentrated liquid was purified by silica gel column chromatography (hexane:ethyl acetate=30:1) to obtain the target compound, (3-[2-(2-methylbutanoyloxy)-1-methylethylidene]-2,2-dimethylcyclobutyl)methyl 2-methylbutanoate, as a geometric isomer mixture at E:Z=50:50, (1.88 g, 5.56 mmol) in a yield of 55%.

The following is spectrum data of (3-[2-(2-methylbutanoyloxy)-1-methylethylidene]-2,2-dimethylcyclobutyl)methyl 2-methylbutanoate (colorless or pale yellow oily liquid) thus produced.

$^1$H-NMR (500 MHz CDCl$_3$): δ=0.87-0.91 (6H, m), 1.12 (3H, d, J=4.2 Hz), 1.13 (3H, d, J=4.6 Hz), 1.14, 1.16 (3H, s, s), 1.26, 1.27 (3H, s, s), 1.40-1.52, 1.61-1.72 (7H, m), 2.19-2.41 (4H, m), 2.62-2.76 (1H, m), 4.08-4.27 (2H, m), 4.32-4.40, 4.44-4.50 (2H, m) ppm Example 26

Preparation of 1-chloromethyl-3-(2-chloro-1-methylethylidene)-2,2-dimethylcyclobutane

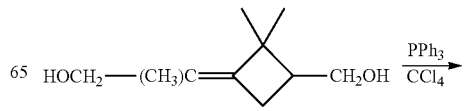

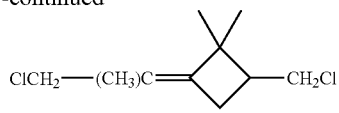

The geometric isomer mixture of E:Z=50:50 of 2-(3-hydroxymethyl-2,2-dimethylcyclobutylidene)propan-1-ol (1.64 g, 9.61 mmol) obtained in Example 14 and carbon tetrachloride (48 g, 0.31 mol) were placed in a reactor in a nitrogen atmosphere and stirred at 0° C. Then, triphenylphosphine (7.56 g, 28.8 mmol) was added, and the mixture was stirred for 24 hours while heating gradually up to 20° C. Subsequently, methanol (5 g) was added to the reaction mixture and stirred at ambient temperature for 1 hour. The reaction mixture was concentrated, followed by addition of hexane, and removal of the precipitate by filtration. The filtrate was concentrated, and purified by silica gel column chromatography (hexane) to obtain the target compound, 1-(2-chloro-1-methylethylidene)-3-chloromethyl-2,2-dimethylcyclobutane, as a geometric isomer mixture at E:Z=50:50, (1.06 g, 5.13 mmol) in a yield of 53%.

The following is spectrum data of 1-chloromethyl-3-(2-chloro-1-methylethylidene)-2,2-dimethylcyclobutane (colorless or pale yellow oily liquid) thus produced.

$^1$H-NMR (500 MHz CDCl$_3$): δ=1.20, 1.23 (3H, s), 1.31, 1.35 (3H, s), 1.59, 1.71 (3H, m), 2.21-2.37 (2H, s) m), 2.70-2.85 (1H, m), 3.50-3.54 (1H, m), 3.61-3.66 (1H, m), 3.89, 4.02 (2H, m) ppm

Example 27

Preparation of 2-(3-hydroxymethyl-2,2-dimethylcyclobutylidene)propyl(triphenyl)phosphonium Bromide

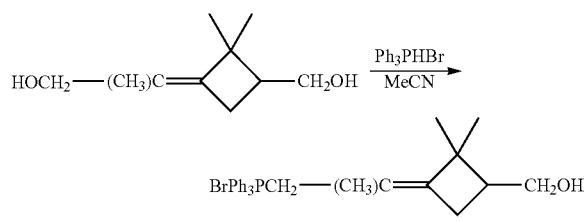

2-(3-Hydroxymethyl-2,2-dimethylcyclobutylidene)propan-1-ol (300 mg, 1.76 mmol) obtained in Example 14, acetonitrile (12 g), and triphenylphosphine hydrobromide (670 mg, 1.95 mmol) were placed in a reactor in a nitrogen atmosphere and stirred with heating under reflux for 5 hours. Pyridine (1.0 g, 13 mmol) was added to a solution of [2-(3-hydroxymethyl-2,2-dimethylcyclobutylidene)propyl] triphenylphosphonium bromide thus obtained and then concentrated at a reduced pressure. Subsequently, toluene (12 g) was added to the concentrated solution, and the operation of 6 concentration at a reduced pressure was repeated twice to obtain a crude product of the target product, triphenyl[2-(3-hydroxymethyl-2,2-dimethylcyclobutylidene)propyl]phosphonium bromide, (872 mg, 1.76 mmol) in a crude yield of 100%.

The following is spectrum data of 2-(3-hydroxymethyl-2,2-dimethylcyclobutylidene)propyl(triphenyl)phosphonium bromide (colorless or pale yellow oily liquid) thus produced.

$^1$H-NMR (500 MHz CD$_3$CN): =0.72, 1.06 (3H, s), 0.85, 1.17 (3H, s), 1.28-1.32, 1.43-1.47 (3H, m), 1.47-2.70 (3H, m), 3.18-3.22, 3.32-3.46 (2H, m), 3.83, 3.91 (2H, d, J=14.6 Hz, d, J=14.6 Hz), 7.26-7.92 (15H, m) ppm

Example 28

Preparation of [2,2-dimethyl-3-(2-bromo-1-methylethylidene)cyclobutyl]methyl Acetate

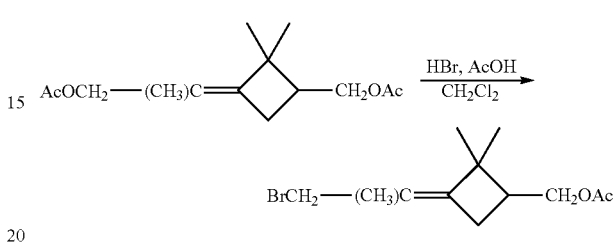

The geometric isomer mixture of E:Z=50:50 of [3-(2-acetoxy-1-methylethylidene)-2,2-dimethylcyclobutyl] methyl acetate (1.78 g, 6.99 mmol) obtained in Example 24, methylene chloride (30 g), and a 30% solution of hydrogen bromide in acetic acid (2.83 g, 10.5 mmol) were placed in a reactor in a nitrogen atmosphere and stirred at 20° C. for 6 hours. Subsequently, a saturated aqueous solution of hydrogen bicarbonate was added to the reaction mixture. The organic layer was separated and subjected to post-treatment by ordinary washing, drying and concentration. Then, the obtained concentrated liquid was purified by silica gel column chromatography (hexane:ethyl acetate=30:1) to obtain the target compound, [2,2-dimethyl-3-(2-bromo-1-methylethylidene)cyclobutyl]methyl acetate, as a geometric isomer mixture at E:Z=50:50, (1.70 g, 6.18 mmol) in a yield of 88%.

The following is spectrum data of [2,2-dimethyl-3-(2-bromo-1-methylethylidene)cyclobutyl]methyl acetate (colorless or pale yellow oily liquid) thus produced.

$^1$H-NMR (500 MHz CDCl$_3$): δ=1.15, 1.20 (3H, s, s), 1.26, 1.31 (3H, s, s), 1.59-1.60, 1.70-171 (3H, m), 2.03 (3H, s), 2.15-2.29 (2H, m), 2.60-2.75 (1H, m), 3.82, 3.94, 3.97 (2H, s, d, J=9.6 Hz, d, J=9.6 Hz), 4.08-4.15 (2H, m) ppm

Example 29

Preparation of (3-isopropenyl-2,2-dimethylcyclobutyl)methoxymethylbenzene and (3-isopropylidene-2,2-dimethylcyclobutyl)methoxymethylbenzene

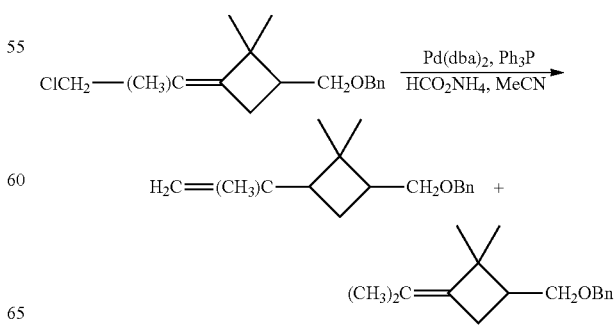

The geometric isomer mixture of E:Z=12:88 of [3-(2-chloro-1-methylethylidene)-2,2-dimethylcyclobutyl]methoxymethylbenzene (502 mg, 1.80 mmol) obtained in Example 17, acetonitrile (24 g), triphenylphosphine (200 mg, 0.763 mmol), and bis(dibenzylideneacetone)palladium (200 mg, 0.348 mmol) were placed in a reactor in a nitrogen atmosphere and stirred at 20° C. Then, ammonium formate (400 mg, 6.34 mmol) was added, and the mixture was stirred at 60° C. for 6 hours. Subsequently, water was added to the mixture. The organic layer was separated and subjected to post-treatment by ordinary washing, drying and concentration. Then, the obtained concentrated liquid was purified by silica gel column chromatography (hexane:ethyl acetate=40:1) to obtain the target compound, (3-isopropenyl-2,2-dimethylcyclobutyl)methoxymethylbenzene and (3-isopropylidene-2,2-dimethylcyclobutyl)methoxymethylbenzene, as an isomer mixture of 68:30:2 of the cis form, the trans form, and the regioisomer at the double bond (i.e., (3-isopropylidene-2,2-dimethylcyclobutyl)methoxymethylbenzene), (415 mg, 1.70 mmol) in a yield of 94%.

The following is spectrum data of cis-(3-isopropenyl-2,2-dimethylcyclobutyl)methoxymethylbenzene (colorless or pale yellow oily liquid) thus produced.

$^1$H-NMR (500 MHz CDCl$_3$): δ=0.81 (3H, s), 1.24 (3H, s), 1.55-1.64 (1H, m), 1.65-1.69 (3H, m), 1.91 (1H, dt, J=7.6, 10.7 Hz), 2.18-2.28 (1H, m), 2.40 (1H, dd, J=7.6, 10.7 Hz), 3.37 (1H, dd, J=6.5, 9.6 Hz), 3.44 (1H, dd, J=8.4, 9.6 Hz), 4.47 (1H, d, J=11.9 Hz), 4.51 (1H, d, J=11.9 Hz), 4.57 (1H, brs), 4.79-4.82 (1H, m), 7.26-7.37 (5H, m) ppm $^{13}$C-NMR (150 MHz, CDCl$_3$): δ=15.68, 21.69, 28.41, 29.06, 40.17, 45.04, 45.78, 71.59, 73.22, 123.32, 127.65, 127.72, 128.47, 138.67, 147.37 ppm Example 30

Preparation of (3-isopropenyl-2,2-dimethylcyclobutyl)methoxymethylbenzene

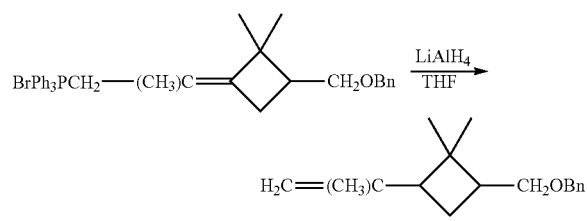

Lithium aluminum hydride (650 mg, 17.1 mmol) and tetrahydrofuran (THF) (24 g) were placed in a reactor in a nitrogen atmosphere and stirred at 0° C. A solution of the crude product of 2-(3-benzyloxymethyl-2,2-dimethylcyclobutylidene)propyl(triphenyl)phosphonium bromide (500 mg) obtained in Example 19 in THF (32 g) was added dropwise at an internal temperature in the reactor of 10° C. or below. After the completion of the dropwise addition, the mixture was stirred for 1.5 hours while heating gradually up to 30° C. Subsequently, water (650 mg) and a 15% by weight solution of sodium hydroxide (650 mg) were added, and then water (1.95 g) was added. Then, the mixture was subjected to filtration, and the obtained filtrate was concentrated at a reduced pressure. The concentrate was purified by silica gel column chromatography (hexane:ethyl acetate=50:1) to obtain the target compound, (3-isopropenyl-2,2-dimethylcyclobutyl)methoxymethylbenzene (143 mg, 0.585 mmol), as a diastereomeric mixture of cis form:trans form=74:26. The yield was 86% after the two steps from [3-(2-bromo-1-methylethylidene)-2,2-dimethylcyclobutyl]methoxymethylbenzene. No double bond regioisomer, (3-isopriden-2,2-dimethylcyclobutyl)methoxymethylbenzene, was detected by GC.

The following is spectrum data of cis-(3-isopropenyl-2,2-dimethylcyclobutyl)methoxymethylbenzene (colorless or pale yellow oily liquid) thus produced.

$^1$H-NMR (500 MHz CDCl$_3$): δ=0.81 (3H, s), 1.24 (3H, s), 1.56 (1H, d, J=10.7 Hz), 1.60 (1H, d, J=10.7 Hz), 1.65-1.69 (3H, m), 1.91 (1H, dt, J=7.6, 10.7 Hz), 2.18-2.28 (1H, m), 2.40 (1H, dd, J=7.6, 10.7 Hz), 3.37 (1H, dd, J=6.5, 9.6 Hz), 3.44 (1H, dd, J=8.4, 9.6 Hz), 4.47 (1H, d, J=11.9 Hz), 4.51 (1H, d, J=11.9 Hz), 4.57 (1H, brs), 4.79-4.82 (1H, m), 7.26-7.37 (5H, m) ppm $^{13}$C-NMR (150 MHz, CDCl$_3$): δ=15.68, 21.69, 28.41, 29.06, 40.17, 45.04, 45.78, 71.59, 73.22, 123.32, 127.65, 127.72, 128.47, 138.67, 147.37 ppm Example 31

Preparation of (3-isopropylidene-2,2-dimethylcyclobutyl)methoxymethylbenzene

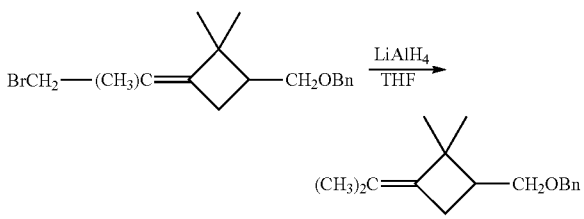

Lithium aluminum hydride (630 mg, 16.6 mmol) and tetrahydrofuran (THF) (120 g) were placed in a reactor and stirred at 0° C. A solution of [3-(2-Bromo-1-methylethylidene)-2,2-dimethylcyclobutyl]methoxymethylbenzene (440 mg, 1.36 mmol) obtained in Example 18 in THF (200 g) was added dropwise at an internal temperature in the reactor of 10° C. or below. After the completion of the dropwise addition, the mixture was stirred for 4 hours while heating gradually up to 30° C. Subsequently, water (630 mg), a 15% by weight aqueous solution of sodium hydroxide (630 mg), and then water (1.89 g) were added. Then, the mixture was subjected to filtration, and the obtained filtrate was concentrated at a reduced pressure. The concentrate was purified by silica gel column chromatography (hexane:ethyl acetate=50:1) to obtain the target compound, (3-isopropylidene-2,2-dimethylcyclobutyl)methoxymethylbenzene, (269 mg, 1.10 mmol) in a yield of 81%. No double bond regioisomer, (3-isopropenyl-2,2-dimethylcyclobutyl)methoxymethylbenzene, was detected in GC.

The following is spectrum data of (3-isopropylidene-2,2-dimethylcyclobutyl)methoxymethylbenzene (colorless or pale yellow oily liquid) thus produced.

$^1$H-NMR (500 MHz CDCl$_3$): δ=1.16 (3H, s), 1.29 (3H, s), 1.46-1.49, 1.59-1.61 (6H, m), 2.10-2.17, 2.21-2.28, 2.58-2.65 (3H, m), 3.47 (1H, dd, J=6.8, 9.6 Hz), 3.60 (1H, dd, J=8.2, 9.3 Hz), 4.52 (2H, s), 7.26-7.40 (5H, m) ppm

Example 32

Preparation of (3-isopropenyl-2,2-dimethylcyclobutyl)methanol and (3-isopropylidene-2,2-dimethylcyclobutyl)methanol

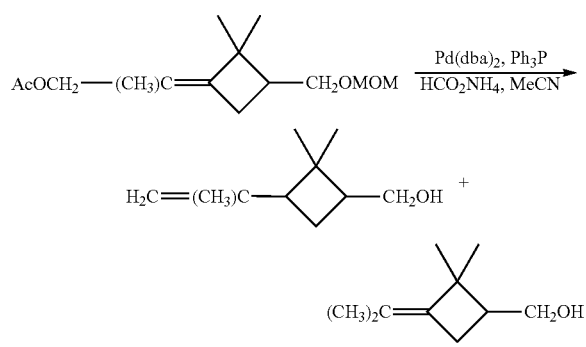

The geometric isomer mixture of E:Z=30:70 of 2-(3-methoxymethoxymethyl-2,2-dimethylcyclobutylidene)propyl acetate obtained in Example 20, acetonitrile (24 g), triphenylphosphine (200 mg, 0.763 mmol), and bis(dibenzylideneacetone)palladium (200 mg, 0.348 mmol) were placed in a reactor in a nitrogen atmosphere and stirred at 20° C. Then, ammonium formate (670 mg, 10.6 mmol) was added, and the mixture was stirred with heating under reflux for 12 hours. Subsequently, water was added to the reaction mixture. The organic layer was separated and subjected to post-treatment by ordinary washing, drying and concentration. Then, the obtained concentrated liquid was purified by silica gel column chromatography (hexane:ethyl acetate=10:1) to obtain the target compound, (3-isopropenyl-2,2-dimethylcyclobutyl)methanol and (3-isopropylidene-2,2-dimethylcyclobutyl)methanol, as an isomer mixture of 68:30:2 of the cis form, the trans form, and the regioisomer at the double bond (i.e., (3-isopropylidene-2,2-dimethylcyclobutyl) methanol), (152 mg, 0.986 mmol) in a yield of 28%.

The following is spectrum data of cis-(3-isopropenyl-2,2-dimethylcyclobutyl)ethanol (colorless or pale yellow oily liquid) thus produced.

$^1$H-NMR (500 MHz CDCl$_3$): δ=0.82 (3H, s), 1.22 (3H, s), 1.55 (1H, q, J=10.7 Hz), 1.65 (3H, s), 1.85-1.91 (1H, m), 2.03-2.10 (1H, m), 2.34-2.39 (1H, m), 3.52 (1H, dd, J=6.5, 10.7 Hz), 3.59 (1H, dd, J=8.3, 10.7 Hz), 4.55 (1H, brs), 4.78-4.81 (1H, m) ppm The following is spectrum data of trans-(3-isopropenyl-2,2-dimethylcyclobutyl)methanol (colorless or pale yellow oily liquid) thus produced.

$^1$H-NMR (500 MHz CDCl$_3$): δ=0.95 (3H, s), 1.12 (3H, s), 1.51 (1H, brs), 1.58-1.63 (1H, m), 1.65 (3H, s), 1.76-1.90 (1H, m), 2.03-2.14 (1H, m), 2.53-2.59 (1H, m), 3.69 (1H, dd, J=7.6, 10.7 Hz), 3.85 (1H, dd, J=7.3, 10.7 Hz), 4.62 (1H, brs), 4.81-4.84 (1H, m) ppm

Example 33

Preparation of 2-[(3-isopropenyl-2,2-dimethylcyclobutyl)methoxy]tetrahydropyran and 2-[(3-isopropylidene-2,2-dimethylcyclobutyl)methoxy]tetrahydropyran

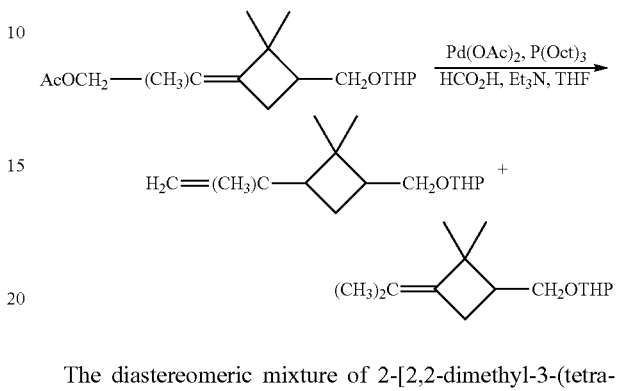

The diastereomeric mixture of 2-[2,2-dimethyl-3-(tetrahydropyran-2-yloxymethyl)cyclobutylidene]propyl acetate (46.2 g, 156 mmol) obtained in Example 21, tetrahydrofuran (THF) (440 g), trioctylphosphine (2.31 g, 6.24 mmol), and palladium acetate (350 mg, 1.56 mmol) were placed in a reactor in a nitrogen atmosphere and stirred at 20° C. Then, triethylamine (63.1 g, 623 mmol) and formic acid (21.5 g, 467 mmol) were added to form triethylammonium formate in the reaction system, followed by stirring at 35° C. for 15 hours. Subsequently, water was added to the reaction mixture. The organic layer was separated and subjected to post-treatment by ordinary washing, drying and concentration. Then, the obtained concentrated liquid was subjected to distillation at a reduced pressure to obtain the target compound, 2-[(3-isopropenyl-2,2-dimethylcyclobutyl)methoxy]tetrahydropyran and 2-[(3-isopropylidene-2,2-dimethylcyclobutyl)methoxy]tetrahydropyran, as an isomer mixture of 64:35:1 of the cis form, the trans form, and the regioisomer at the double bond (i.e., 2-[(3-isopropylidene-2,2-dimethylcyclobutyl)methoxy]tetrahydropyran), (35.3 g, 148 mmol) in a yield of 95%.

The following is spectrum data of 2-[(3-isopropenyl-2,2-dimethylcyclobutyl)methoxy]tetrahydropyran (colorless or pale yellow oily liquid) thus produced.

$^1$H-NMR (500 MHz CDCl$_3$): δ=0.78-1.25 (6H, m), 1.40-1.75 (10H, m), 1.76-2.62 (3H, m), 3.24-3.97 (4H, m) m), 4.50-4.65 (2H, m), 4.77-4.83 (1H, m) ppm

Example 34

Preparation of 2-[(3-isopropenyl-2,2-dimethylcyclobutyl)methoxy]tetrahydropyran

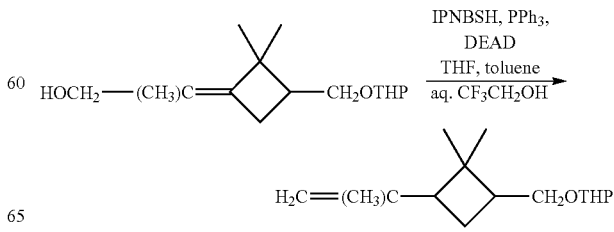

The diastereomeric mixture of 2-[2,2-dimethyl-3-(tetrahydropyran-2-yloxymethyl)cyclobutylidene]propan-1-ol (560 mg, 2.20 mmol) obtained in Example 13, tetrahydrofuran (THF) (24 g), triphenylphosphine (761 mg, 2.90 mmol), and N'-isopropylidene-2-nitrobenzenesulfonohydrazide (IPNBSH) (746 mg, 2.90 mmol) were placed in a reactor in a nitrogen atmosphere and stirred at 0° C. Then, a 40% solution of diethyl azodicarboxylate (DEAD) (1.22 g, 2.80 mmol) in toluene was added, and the mixture was stirred for 2 hours while heating gradually up to 30° C. Subsequently, a mixed liquid of trifluoroethanol (14 g) and water (14 g) was added to the reaction mixture, and the mixture was stirred at 30° C. for 6 hours. A saturated solution of hydrogen bicarbonate was added, followed by extraction with ether. The separated organic layer was subjected to post-treatment by ordinary washing, drying and concentration. Then, the obtained concentrated liquid was purified by silica gel column chromatography (hexane:ethyl acetate=40:1) to obtain the target compound, 2-[(3-isopropenyl-2,2-dimethylcyclobutyl)methoxy]tetrahydropyran, as an isomer mixture of cis form:trans form=51:49 (202 mg, 0.846 mmol) in a yield of 38%. No double bond regioisomer, 2-[(3-isopropylidene-2,2-dimethylcyclobutyl)methoxy]tetrahydropyran, was detected in GC.

Example 35

Preparation of (3-isopropenyl-2,2-dimethylcyclobutyl)methyl Acetate and (3-isopropylidene-2,2-dimethylcyclobutyl)methylacetate

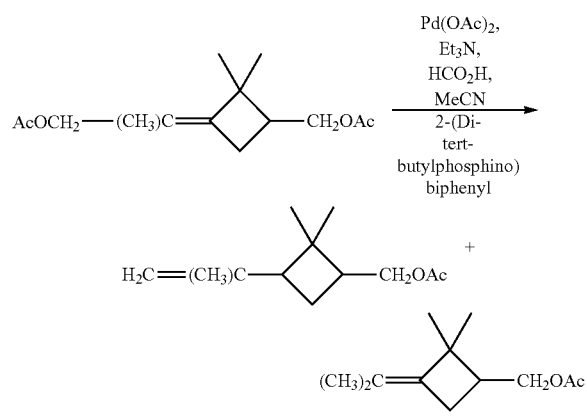

The geometric isomer mixture of E:Z=57:43 of [3-(2-acetoxy-1-methylethylidene)-2,2-dimethylcyclobutyl] methyl acetate (483 mg, 1.90 mmol) obtained in Example 24, acetonitrile (12 g), 2-(di-tert-butylphosphino)biphenyl (230 mg, 0.771 mmol), and palladium acetate (40 mg, 0.18 mmol) were placed in a reactor in a nitrogen atmosphere and stirred at 20° C. Then, triethylamine (770 mg, 7.61 mmol) and formic acid (260 mg, 5.65 mmol) were added to form triethylammonium formate in the reaction system, followed by stirring at 30° C. for 19 hours. Subsequently, water was added to the reaction mixture. The organic layer was separated and subjected to post-treatment by ordinary washing, drying and concentration. Then, the obtained concentrated liquid was purified by silica gel column chromatography (hexane:ethyl acetate=50:1) to obtain the target compound, (3-isopropenyl-2,2-dimethylcyclobutyl)methyl acetate and (3-isopropylidene-2,2-dimethylcyclobutyl)methy acetate, as an isomer mixture of 78:18:4 of the cis form, the trans form, and the regioisomer at the double bond (i.e., (3-isopropylidene-2,2-dimethylcyclobutyl)methyl acetate), (328 mg, 1.67 mmol) in a yield of 88%.

The following is spectrum data of cis-(3-isopropenyl-2,2-dimethylcyclobutyl)methyl acetate (colorless or pale yellow oily liquid) thus produced.

IR (D-ATR): νmax=3080, 2957, 2870, 1743, 1647, 1460, 1385, 1368, 1240, 1162, 1031, 972, 886, 641, 607, 556 cm$^{-1}$ $^1$H-NMR (500 MHz CDCl$_3$): δ=0.81 (3H, s), 1.19 (3H, s), 1.59 (1H, q, J=10.7 Hz) 1.64 (3H, t, J=0.8 Hz), 1.89 (1H, dt, J=7.6, 10.7 Hz), 2.02 (3H, s), 2.13-2.22 (1H, m), 2.37-2.41 (1H, m), 3.94 (1H, dd, J=8.6, 11.3 Hz), 4.04 (1H, dd, J=6.3, 11.3 Hz), 4.56 (1H, brs), 4.79-4.82 (1H, m) ppm $^{13}$C-NMR (150 MHz, CDCl$_3$): δ=16.07, 21.02, 22.92, 22.96, 30.92, 39.74, 41.05, 48.83, 64.95, 109.42, 144.93, 171.05 ppm Example 36

Preparation of (3-isopropenyl-2,2-dimethylcyclobutyl)methyl Acetate and (3-isopropylidene-2,2-dimethylcyclobutyl)methylacetate

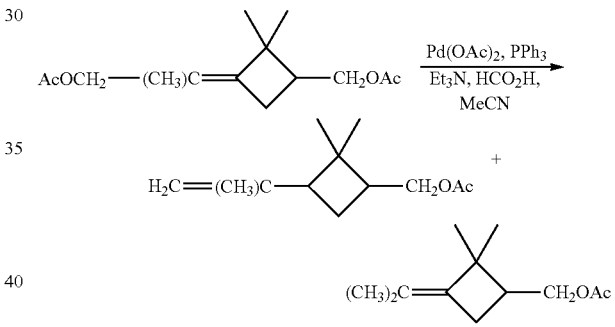

The geometric isomer mixture of E:Z=57:43 of [3-(2-acetoxy-1-methylethylidene)-2,2-dimethylcyclobutyl] methyl acetate (483 mg, 1.90 mmol) obtained in Example 24, acetonitrile (12 g), triphenylphosphine (200 mg, 0.763 mmol), and palladium acetate (40 mg, 0.18 mmol) were were placed in a reactor in a nitrogen atmosphere and stirred at 20° C. Then, triethylamine (770 mg, 7.61 mmol) and formic acid (260 mg, 5.65 mmol) were added to form triethylammonium formate in the reaction system, followed by stirring with heating under reflux for 24 hours. Subsequently, water was added to the reaction mixture. The organic layer was separated and subjected to post-treatment by ordinary washing, drying and concentration. Then, the obtained concentrated liquid was purified by silica gel column chromatography (hexane:ethyl acetate=50:1) to obtain the target compound, (3-isopropenyl-2,2-dimethylcyclobutyl)methyl acetate and (3-isopropylidene-2,2-dimethylcyclobutyl)methyl acetate, as an isomer mixture of 68:30:2 of the cis form, the trans form, and the regioisomer at the double bond (i.e., (3-isopropylidene-2,2-dimethylcyclobutyl)methyl acetate), (321 mg, 1.63 mmol) in a yield of 86%. The spectrum data of cis-(3-isopropenyl-2,2-dimethylcyclobutyl)methyl acetate (colorless or pale yellow oily liquid) had the same spectra as in Example 35.

Example 37

Preparation of (3-isopropenyl-2,2-dimethylcyclobutyl)methyl Acetate and (3-isopropylidene-2,2-dimethylcyclobutyl)methylacetate

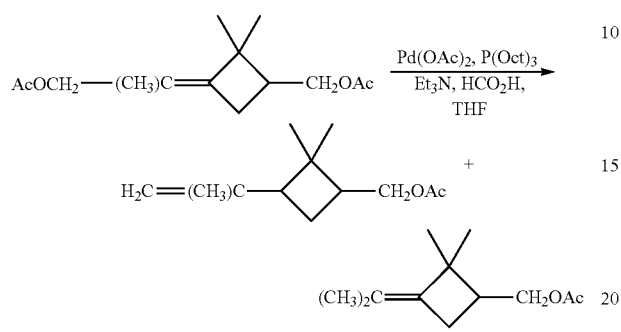

The geometric isomer mixture of E:Z=57:43 of [3-(2-acetoxy-1-methylethylidene)-2,2-dimethylcyclobutyl]methyl acetate (1.86 g, 7.33 mmol) obtained in Example 24, tetrahydrofuran (THF) (19 g), trioctylphosphine (220 mg, 0.594 mmol), and palladium acetate (33 mg, 0.15 mmol) were placed in a reactor in a nitrogen atmosphere and stirred at 20° C. Then, triethylamine (2.97 g, 29.3 mmol) and formic acid (1.01 g, 22.0 mmol) were added to form triethylammonium formate in the reaction system, followed by stirring at 35° C. for 5 hours. Subsequently, water was added to the reaction mixture. The organic layer was separated and subjected to post-treatment by ordinary washing, drying and concentration. Then, the obtained concentrated liquid was purified by silica gel column chromatography (hexane:ethyl acetate=50:1) to obtain the target compound, (3-isopropenyl-2,2-dimethylcyclobutyl)methyl acetate and (3-isopropylidene-2,2-dimethylcyclobutyl)methyl acetate, as an isomer mixture of 65:34:1 of the cis form, the trans form, and the regioisomer at the double bond (i.e., (3-isopropylidene-2,2-dimethylcyclobutyl)methyl acetate), (1.27 g, 6.45 mmol) in a yield of 88%. The spectrum data of cis-(3-isopropenyl-2,2-dimethylcyclobutyl)methyl acetate thus obtained (colorless or pale yellow oily liquid) had the same spectra as in Example 35.

Example 38

Preparation of (3-isopropenyl-2,2-dimethylcyclobutyl)methyl Acetate and (3-isopropylidene-2,2-dimethylcyclobutyl)methylacetate

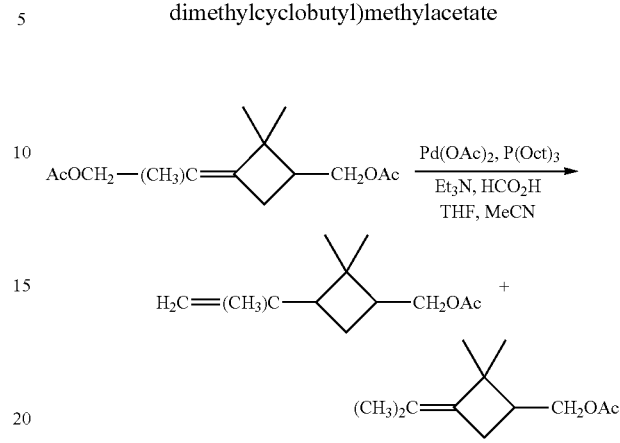

Palladium acetate (1.86 g, 8.27 mmol), tetrahydrofuran (THF) (1602 g), trioctylphosphine (12.3 g, 33.1 mmol), and a geometric isomer mixture of E:Z=70:30 of [3-(2-acetoxy-1-methylethylidene)-2,2-dimethylcyclobutyl]methyl acetate (420 g, 1.65 mol) were placed in a reactor in a nitrogen atmosphere and stirred at 45° C. Subsequently, triethylamine (335 g, 3.31 mol) and a solution of formic acid (114 g, 2.48 mol) in acetonitrile (MeCN) (335 g) were added dropwise at an internal temperature in the reactor of 50° C. or below. After the completion of the dropwise addition, the mixture was stirred at 45° C. for 4 hours. Subsequently, acetic acid was added to the reaction mixture and then brine was added, and the separated organic layer was subjected to post-treatment by ordinary washing, drying and concentration. Then, the obtained concentrated liquid was subjected to distillation at a reduced pressure to obtain the target compound, (3-isopropenyl-2,2-dimethylcyclobutyl)methyl acetate and (3-isopropylidene-2,2-dimethylcyclobutyl) methyl acetate, as an isomer mixture of 68:31:1 of the cis form, the trans form, and the regioisomer at the double bond (i.e., (3-isopropylidene-2,2-dimethylcyclobutyl)methyl acetate), (310 g, 1.58 mmol) in a yield of 96%. The spectrum data of cis-(3-isopropenyl-2,2-dimethylcyclobutyl)methyl acetate thus obtained (colorless or pale yellow oily liquid) had the same spectra as in Example 35.

Example 39

Preparation of (3-isopropenyl-2,2-dimethylcyclobutyl)methyl 2-methylbutanoate and (3-isopropylidene-2,2-dimethylcyclobutyl)methyl 2-methylbutanoate

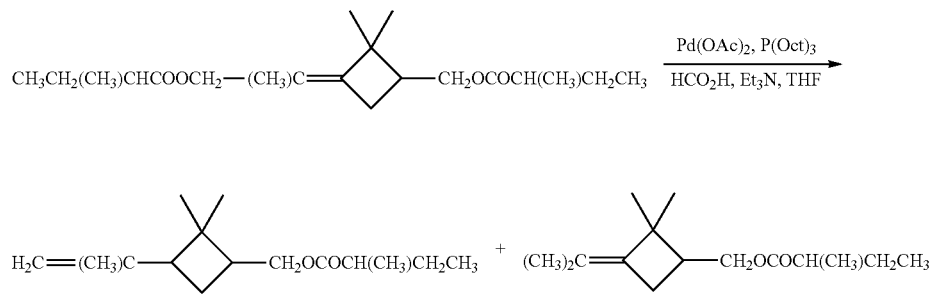

The isomer mixture of E:Z=50:50 of 16 (3-[2-(2-methylbutanoyloxy)-1-methylethylidene]-2,2-dimethylcyclobutyl)methyl 2-methylbutanoate (1.84 g, 5.43 mmol) obtained in Example 25, tetrahydrofuran (THF) (40 g), trioctylphosphine (160 mg, 0.436 mmol), and palladium acetate (24 mg, 0.11 mmol) were placed in a reactor in a nitrogen atmosphere and stirred at 20° C. for 1 hour. Then, triethylamine (2.19 g, 21.7 mmol) and formic acid (750 mg, 16.3 mmol) were added to from triethylammonium formate in the reaction system, followed by stirring at 35° C. for 24 hours. Subsequently, water was added to the reaction mixture. The organic layer was separated and subjected to post-treatment by ordinary washing, drying and concentration. Then, the obtained concentrated liquid was purified by silica gel column chromatography (hexane:ethyl acetate=80:1) to obtain the target compound, (3-isopropenyl-2,2-dimethylcyclobutyl)methyl 2-methylbutanoate and (3-isopropylidene-2,2-dimethylcyclobutyl)methyl 2-methylbutanoate, as an isomer mixture of 64:32:4 of the cis form, the trans form, and the regioisomer at the double bond (i.e., (3-isopropylidene-2,2-dimethylcyclobutyl)methyl 2-methylbutanoate), (1.15 g, 4.84 mmol) in a yield of 89%.

The following is spectrum data of cis-(3-isopropenyl-2,2-dimethylcyclobutyl)methyl 2-methylbutanoate (colorless or pale yellow oily liquid) thus produced.

$^1$H-NMR (500 MHz CDCl$_3$): δ=0.81 (3H, s), 0.89 (3H, t, J=7.5 Hz), 1.11 (3H, q, J=7.0 Hz), 1.20 (3H, s), 1.40-1.51 (1H, m), 1.56-1.72 (5H, m), 1.87 (1H, dt, J=7.6, 10.7 Hz), 2.13-2.22 (1H, m), 2.29-2.41 (2H, m), 3.92, 3.94 (1H, dd, J=6.1, 11.1 Hz, dd, J=6.1, 11.1H), 4.04, 4.05 (1H, dd, J=6.1, 11.1 Hz, dd, J=6.1, 11.1 Hz), 4.55 (1H, brs), 4.78-4.81 (1H, m) ppm

Example 40

Preparation of 1-chloromethyl-3-isopropenyl-2,2-dimethylcyclobutane and 1-chloromethyl-3-isopropylidene-2,2-dimethylcyclobutane

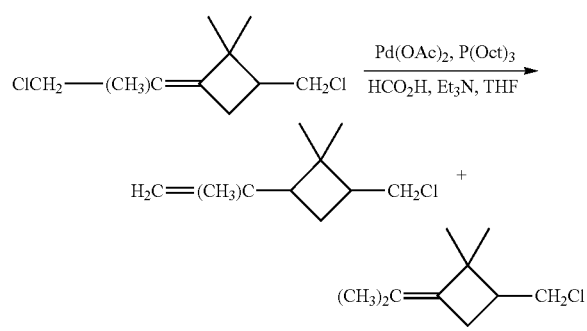

The geometric isomer mixture of E:Z=50:50 of 1-chloromethyl-3-(2-chloro-1-methylethylidene)-2,2-dimethylcyclobutane (988 mg, 4.77 mmol) obtained in Example 26, tetrahydrofuran (THF) (20 g), trioctylphosphine (280 mg, 0.763 mmol), and palladium acetate (40 mg, 0.18 mmol) were placed in a reactor in a nitrogen atmosphere and stirred at 20° C. for 1 hour. Then, triethylamine (1.93 g, 19.1 mmol) and formic acid (660 mg, 14.3 mmol) were added to form triethylammonium formate in the reaction system, followed by stirring at 55° C. for 24 hours. Subsequently, water was added to the reaction mixture. The organic layer was separated and subjected to post-treatment by ordinary washing, drying and concentration. Then, the obtained concentrated liquid was purified by silica gel column chromatography (hexane) to obtain the target compound, 1-chloromethyl-3-isopropenyl-2,2-dimethylcyclobutane and 1-chloromethyl-3-isopropylidene-2,2-dimethylcyclobutane, as an isomer mixture of 53:46:1 of the cis form, the trans form, and the regioisomer at the double bond (i.e., 1-chloromethyl-3-isopropylidene-2,2-dimethylcyclobutane), (553 mg, 3.20 mmol) in a yield of 67%.

The following is spectrum data of 1-chloromethyl-3-isopropenyl-2,2-dimethylcyclobutane (colorless or pale yellow oily liquid) thus produced.

$^1$H-NMR (500 MHz CDCl$_3$): δ=0.85, 0.98 (3H, s), 1.14, 1.26 (3H, s), 1.57, 1.72 (1H, q, J=10.7 Hz, m), 1.66-1.67 (3H, m), 1.98, 2.04-2.10 (1H, dt, J=7.7, 10.7 Hz, m), 2.15-2.30 (1H, m) m), 2.35-2.39, 2.52-2.57 (1H, m), 3.40-3.49, 3.60, 3.72 (2H, m, dd, J=8.8, 10.7 Hz, dd, J=6.8, 10.7 Hz), 4.56, 4.66 (1H, brs, brs), 4.80-4.83, 4.85-4.87 (1H, m) ppm

Example 41

Preparation of (3-isopropenyl-2,2-dimethylcyclobutyl)methanol

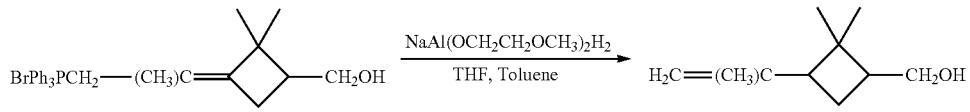

The crude product of triphenyl[2-(3-hydroxymethyl-2,2-dimethylcyclobutylidene)propyl]phosphonium bromide (872 mg, 1.76 mmol) obtained in Example 27 and tetrahydrofuran (THF) (70 g) were placed in a reactor in a nitrogen atmosphere and stirred at 0° C. Then, a 3.60 M solution of sodium bis(2-methoxyethoxy)aluminum hydride in toluene (2.00 ml, 7.20 mmol) was added dropwise at an internal temperature in the reactor of 10° C. or below. After the completion of the dropwise addition, the mixture was stirred for 1 hour while heating gradually up to 20° C. Then, a 10% by weight aqueous solution of sodium hydroxide was added to the reaction mixture. The organic layer was separated and subjected to post-treatment by ordinary washing, drying and concentration. Then, the obtained concentrated liquid was purified by silica gel column chromatography (hexane:ethyl acetate=10:1) to obtain the target compound, (3-isopropenyl-2,2-dimethylcyclobutyl)methanol, as a geometric isomer mixture at 77:23 of the cis form and the trans form, (195 mg, 1.27 mmol) in a yield of 72%. The spectrum data of cis-(3-isopropenyl-2,2-dimethylcyclobutyl)methanol (colorless or pale yellow oily liquid) and trans-(3-isopropenyl-2,2-dimethylcyclobutyl)methanol (colorless or pale yellow oily liquid) had the same spectra as in Example 32, respectively. No double bond regioisomer, (3-isopropylidene-2,2-dimethylcyclobutyl)methanol, was detected in GC.

Example 42

Preparation of (3-isopropylidene-2,2-dimethylcyclobutyl)methanol

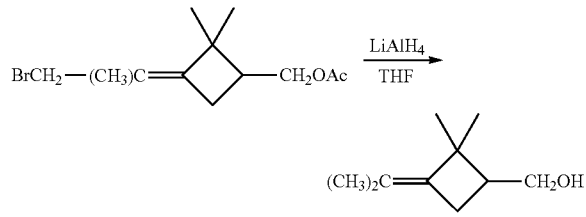

Lithium aluminum hydride (570 mg, 15.0 mmol) and tetrahydrofuran (THF) (60 g) were were placed in a reactor in a nitrogen atmosphere and stirred at 0° C. for 1 hour. The geometric isomer mixture of E:Z=50:50 of [2,2-dimethyl-3-(2-bromo-1-methylethylidene)cyclobutyl]methyl acetate obtained in Example 28 (1.62 g, 5.89 mmol) was added dropwise to this solution at an internal temperature in the reactor of 5° C. or below. After the completion of the dropwise addition, the mixture was stirred for 6 hours while heating gradually up to 20° C. Subsequently, water (570 mg) and a 15% by weight aqueous solution of sodium hydroxide (570 mg) were added to the reaction mixture, and water (1.71 g) was further added. Then, the reaction mixture was subjected to filtration, and the obtained filtrate was concentrated at a reduced pressure. The concentrate was purified by silica gel column chromatography (hexane:ethyl acetate=10:1) to obtain the target compound, (3-isopropylidene-2,2-dimethylcyclobutyl)methanol (909 mg, 5.89 mmol) in a yield of 100%. No double bond regioisomer, (3-isopropenyl-2,2-dimethylcyclobutyl)methanol, was detected in GC.

The following is spectrum data of (3-isopropylidene-2,2-dimethylcyclobutyl)methanol (colorless or pale yellow oily liquid) thus produced.

$^1$H-NMR (500 MHz CDCl$_3$): δ=1.15 (3H, s), 1.26 (3H, s), 1.45 (3H, s), 1.56-1.58 (3H, m), 1.63 (1H, brs), 2.03-2.14 (2H, m), 2.54-2.62 (1 H, m), 3.61 (1H, dd, J=6.9, 10.7 Hz), 3.76 (1H, dd, J=7.7, 10.7 Hz) ppm $^{13}$C-NMR (150 MHz, CDCl$_3$): δ=18.48, 19.53, 20.90, 27.70, 28.67, 42.65, 44.05, 64.30, 122.42, 137.39 ppm.

Example 43

Preparation of (3-isopropenyl-2,2-dimethylcyclobutyl)methanol and (3-isopropylidene-2,2-dimethylcyclobutyl)methanol

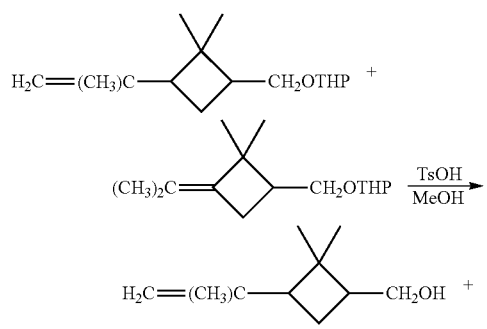

The isomer mixture of 2-[(3-isopropenyl-2,2-dimethylcyclobutyl)methoxy]tetrahydropyran (32.7 g, 137 mmol) obtained in Example 34, p-toluenesulfonic acid (320 mg, 0.0019 mmol) and methanol (436 g) were placed in a reactor in a nitrogen atmosphere and stirred at 20° C. for 24 hours. Subsequently, sodium bicarbonate (210 mg) was added to the reaction mixture, and the mixture was concentrated. Then, the concentrate was purified by silica gel column chromatography (hexane:ethyl acetate=10:1) to obtain the target compound, (3-isopropenyl-2,2-dimethylcyclobutyl)methanol and (3-isopropylidene-2,2-dimethylcyclobutyl)methanol, as an isomer mixture of 64:35:1 of the cis form, the trans form, and the regioisomer at the double bond (i.e., 6 (3-isopropylidene-2,2-dimethylcyclobutyl)methanol, (21.1 g, 137 mmol)) in a yield of 100%. The spectrum data of cis-(3-isopropenyl-2,2-dimethylcyclobutyl)methanol thus obtained (colorless or pale yellow oily liquid) and trans-(3-isopropenyl-2,2-dimethylcyclobutyl)methanol thus obtained (colorless or pale yellow oily liquid) had the same spectra as in Example 32, respectively.

Example 44

Preparation of (3-isopropenyl-2,2-dimethylcyclobutyl)methyl Acetate

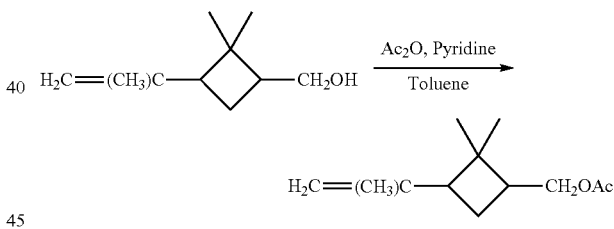

The isomer mixture of cis-from: trans-form=77:23 of (3-isopropenyl-2,2-dimethylcyclobutyl)methanol (154 mg, 1.00 mmol) obtained in Example 41, pyridine (316 mg) and toluene (10 g) were placed in a reactor in a nitrogen atmosphere and stirred at 0° C. Then, acetic anhydride (204 mg, 2.00 mmol) was added dropwise at an internal temperature in the reactor of 10° C. or below. After the completion of the dropwise addition, the mixture was stirred for 6 hours while heating gradually up to 20° C. Subsequently, water was added to the reaction mixture. The organic layer was separated and subjected to post-treatment by ordinary washing, drying and concentration. Then, the obtained concentrated liquid was purified by silica gel column chromatography (hexane:ethyl acetate=50:1) to obtain the target compound, (3-isopropenyl-2,2-dimethylcyclobutyl)methyl acetate, as a geometric isomer mixture at 77:23 of the cis form and the trans form, (183 mg, 0.930 mmol) in a yield of 93%. The spectrum data of cis-(3-isopropenyl-2,2-dimethylcyclobutyl)methyl acetate thus obtained (colorless or pale yellow oily liquid) had the same spectra as in Example 35.

Example 45

Preparation of (3-isopropylidene-2,2-dimethylcyclobutyl)methylacetate

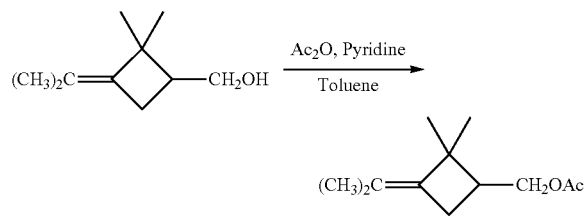

(3-Isopropylidene-2,2-dimethylcyclobutyl)methanol (818 mg, 5.30 mmol) obtained in Example 42, toluene (10 g), pyridine (1.68 g, 21.2 mmol) and acetic anhydride (1.09 g, 10.7 mmol) were placed in a reactor in a nitrogen atmosphere and stirred at 20° C. for 24 hours. Subsequently, water was added to the reaction mixture. The organic layer was separated and subjected to post-treatment by ordinary washing, drying and concentration. Then, the obtained concentrated liquid was purified by silica gel column chromatography (hexane:ethyl acetate=50:1) to obtain the target compound, (3-isopropylidene-2,2-dimethylcyclobutyl)methyl acetate, (911 mg, 4.64 mmol) in a yield of 88%.

The following is spectrum data of (3-isopropylidene-2,2-dimethylcyclobutyl)methyl acetate (colorless or pale yellow oily liquid) thus produced.

$^1$H-NMR (500 MHz CDCl$_3$): δ=1.13 (3H, s), 1.24 (3H, s), 1.45 (3H, s), 1.57 (3H, t, J=1.9 Hz), 2.03 (3H, s), 2.10-2.22 (2H, m), 2.56-2.63 (1H, m), 4.07-4.15 (2H, m) ppm

Example 46

Preparation of (3-isopropenyl-2,2-dimethylcyclobutyl)methyl Acetate and (3-isopropylidene-2,2-dimethylcyclobutyl)methylacetate

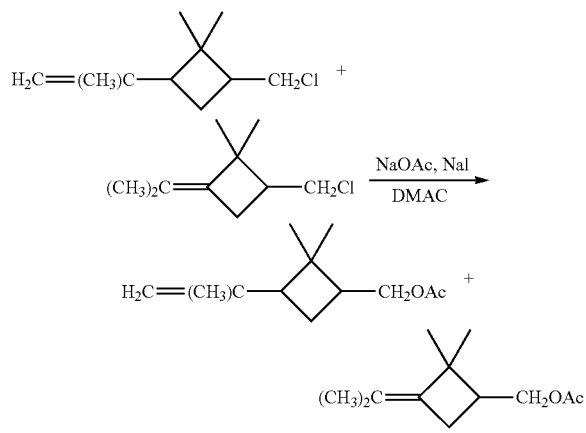

The mixture of 1-chloromethyl-3-isopropenyl-2,2-dimethylcyclobutane and 1-chloromethyl-3-isopropylidene-2,2-dimethylcyclobutane (535 mg, 3.10 mmol) obtained in Example 40, sodium acetate (580 mg, 7.07 mmol), sodium iodide (100 mg, 0.667 mmol), and dimethylacetamide (DMAC) (20 g) were placed in a reactor in a nitrogen atmosphere and stirred at 150° C. for 24 hours. Subsequently, water was added to the reaction mixture. The organic layer was separated and subjected to post-treatment by ordinary washing, drying and concentration. Then, the obtained concentrated liquid was purified by silica gel column chromatography (hexane:ethyl acetate=50:1) to obtain the target compound, (3-isopropenyl-2,2-dimethylcyclobutyl)methyl acetate and (3-isopropylidene-2,2-dimethylcyclobutyl)methyl acetate, as an isomer mixture of 57:42:1 of the cis form, the trans form, and the regioisomer at the double bond (i.e., (3-isopropylidene-2,2-dimethylcyclobutyl)methyl acetate), (255 mg, 1.30 mmol) in a yield of 42%. The spectrum data of cis-(3-isopropenyl-2,2-dimethylcyclobutyl)methyl acetate thus obtained (colorless or pale yellow oily liquid) had the same spectra as in Example 35.

Example 47

Preparation of (3-isopropylidene-2,2-dimethylcyclobutyl)methyl Methanesulfonate

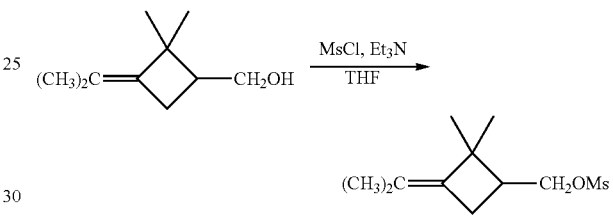

(3-Isopropylidene-2,2-dimethylcyclobutyl)methanol (858 mg, 5.56 mmol) obtained in Example 42, tetrahydrofuran (THF) (20 g), and triethylamine (1.71 g, 16) were placed in a reactor in a nitrogen atmosphere and stirred at 0° C. for 1 hour. Methanesulfonyl chloride (MsCl) (1.09 g, 10.7 mmol) was added dropwise at an internal temperature in the reactor of 10° C. or below. After the completion of the dropwise addition, the mixture was stirred at 20° C. for 1 hour. Subsequently, water was added to the reaction mixture. The organic layer was separated and subjected to post-treatment by ordinary washing, drying and concentration. Then, the obtained concentrated liquid was purified by silica gel column chromatography (hexane:ethyl acetate=10:1) to obtain the target compound, (3-isopropylidene-2,2-dimethylcyclobutyl)methyl methanesulfonate, (1.29 g, 5.56 mmol) in a yield of 100%.

The following is spectrum data of (3-isopropylidene-2,2-dimethylcyclobutyl)methylmethanesulfonate (colorless or pale yellow oily liquid) thus produced.

$^1$H-NMR (500 MHz CDCl$_3$): δ=1.17 (3H, s), 1.27 (3H, s), 1.45 (3H, brs), 1.58 (31, t, J=1.9 Hz), 2.15-2.22 (1H, m), 2.25-2.33 (1H, m), 2.61-2.67 (1H, m), 3.00 (3H, s), 4.23 (1H, dd, J=7.3, 9.9 Hz), 4.31 (1H, dd, J=8.0, 10.0 Hz) ppm

Example 48

Preparation of (3-isopropylidene-2,2-dimethylcyclobutyl)methyl 3-methyl-2-butenoate

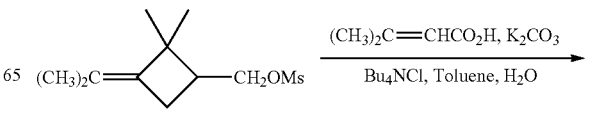

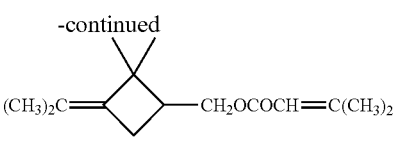

(3-Isopropylidene-2,2-dimethylcyclobutyl)methyl methanesulfonate, (1.29 g, 5.56 mmol) obtained in Example 47, toluene (40 g), water (430 mg), senecioic acid (3-methyl-2-butenoic acid) (690 mg, 6.92 mmol), potassium carbonate (610 mg, 4.39 mmol) and tetrabutylammonium chloride (60 mg, 0.23 mmol) were placed in a reactor in a nitrogen atmosphere and stirred at 100° C. for 24 hours. Subsequently, water was added to the reaction mixture. The organic layer was separated and subjected to post-treatment by ordinary washing, drying and concentration. Then, the obtained concentrated liquid was purified by silica gel column chromatography (hexane:ethyl acetate=50:1) to obtain the target compound, (3-isopropylidene-2,2-dimethylcyclobutyl)methyl 3-methyl-2-butenoate, (1.20 g, 5.06 mmol) in a yield of 91%.

The following is spectrum data of (3-isopropylidene-2,2-dimethylcyclobutyl)methyl 3-methyl-2-butenoate (colorless or pale yellow oily liquid) thus produced.

IR (D-ATR): νmax=2956, 2917, 2864, 1719, 1659, 1449, 1376, 1361, 1349, 1272, 1227, 1146, 1076, 993, 851 cm$^{-1}$ $^1$H-NMR (500 MHz CDCl$_3$): δ 1.14 (3H, s), 1.25 (3H, s), 1.45 (3H, brs), 1.56-1.58 (3H, m), 1.88 (3H, d, J=1.5 Hz), 2.12-2.30 (5H, m), 2.56-2.64 (1H, m), 4.11 (1H, dd, J=6.8, 11.4 Hz), 4.15 (1H, dd, J=8.0, 11.5 Hz), 5.64-5.66 (1H, m) ppm $^{13}$C-NMR (150 MHz, CDCl$_3$): δ=18.50, 19.54, 20.15, 20.99, 27.34, 27.78, 28.39, 39.14, 44.21, 64.75, 116.15, 122.53, 137.18, 156.25, 166.82 ppm Example 49

Preparation of
(3-isopropenyl-2,2-dimethylcyclobutyl)methanol
and
(3-isopropylidene-2,2-dimethylcyclobutyl)methanol

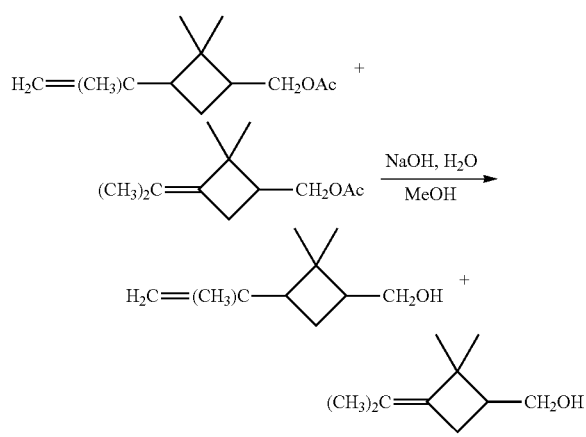

The isomer mixture of (3-isopropenyl-2,2-dimethylcyclobutyl)methyl acetate (60.3 g, 307 mmol) obtained in Example 38, methanol (94 g), a 25% aqueous solution of sodium hydroxide (94 g) were placed in a reactor in a nitrogen atmosphere, and stirred at 20° C. for 12 hours. Subsequently, brine was added to the reaction mixture. The organic layer was separated and subjected to post-treatment by ordinary washing, drying and concentration. Then, the obtained concentrated liquid was subjected to distillation at a reduced pressure to obtain the target compound, (3-isopropenyl-2,2-dimethylcyclobutyl)methanol and (3-isopropylidene-2,2-dimethylcyclobutyl)methanol, as an isomer mixture of 67:32:1 of the cis form, the trans form, and the regioisomer at the double bond (i.e., (3-isopropylidene-2,2-dimethylcyclobutyl)methanol), (46.0 g, 298 mmol) in a yield of 97%. The spectrum data of cis-(3-isopropenyl-2,2-dimethylcyclobutyl)methanol (colorless or pale yellow oily liquid) thus obtained and trans-(3-isopropenyl-2,2-dimethylcyclobutyl)methanol thus obtained (colorless or pale yellow oily liquid) had the same spectra as in Example 32, respectively.

Example 50

Preparation of (3-isopropenyl-2,2-dimethylcyclobutyl)methyl 2-methylbutanoate and (3-isopropylidene-2,2-dimethylcyclobutyl)methyl 2-methylbutanoate

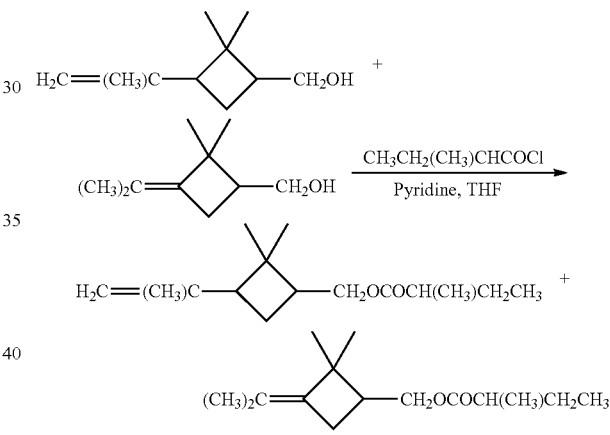

The isomer mixture of (3-isopropenyl-2,2-dimethylcyclobutyl)methanol (12.6 g, 82.0 mmol) obtained in Example 49, tetrahydrofuran (THF) (100 g), pyridine. (16.9 g, 213 mmol) were placed in a reactor in a nitrogen atmosphere, and the mixture was stirred at 0° C. 2-Methylbutanoyl chloride (12.9 g, 107 mmol) was added dropwise at an internal temperature in the reactor of 15° C. or below. After the completion of the dropwise addition, the mixture was stirred for 6 hours while heating gradually up to 20° C. Subsequently, brine was added to the reaction mixture. The organic layer was separated and subjected to post-treatment by ordinary washing, drying and concentration. Then, the obtained concentrated liquid was subjected to distillation at a reduced pressure to obtain the target compound, (3-isopropenyl-2,2-dimethylcyclobutyl)methyl 2-methylbutanoate and (3-isopropylidene-2,2-dimethylcyclobutyl)methyl 2-methylbutanoate, as an isomer mixture of 68:31:1 of the cis form, the trans form, and the regioisomer at the double bond (i.e., (3-isopropylidene-2,2-dimethylcyclobutyl) methyl 2-methylbutanoate), (19.5 g, 81.6 mmol) in a yield of 100%. The spectrum data of cis-(3-isopropenyl-2,2-dimethylcyclobutyl)methyl 2-methylbutanoate thus obtained had the same spectra as in Example 39.

Example 51

Preparation of (3-isopropenyl-2,2-dimethylcyclobutyl)methyl 3-methyl-3-butenoate and (3-isopropylidene-2,2-dimethylcyclobutyl)methyl 3-methyl-3-butenoate

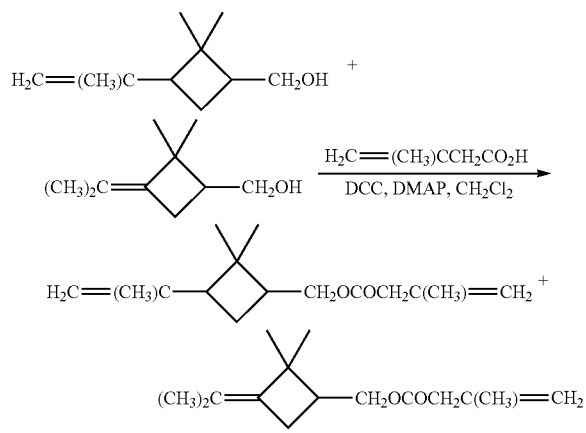

The isomer mixture of (3-isopropenyl-2,2-dimethylcyclobutyl)methanol (13.4 g, 86.6 mmol) obtained in Example 49, dichloromethane (665 g), 3-methyl-3-butenoic acid (12.5 g, 125 mmol), and 4-dimethylaminopyridine (DMAP) (1.06 g, 8.66 mmol) were placed in a reactor in a nitrogen atmosphere, and stirred at 0° C. N,N'-dicyclohexylbodiimide (DCC) (24.8 g, 120 mmol) was added to the mixture. Then, the mixture was stirred for 2 hours while heating gradually up to 20° C. Subsequently, ether and brine were added to the reaction mixture. The organic layer was separated and subjected to post-treatment by ordinary washing, drying and concentration. Then, the obtained concentrated liquid was purified by silica gel column chromatography (hexane:ethyl acetate=40:1) to obtain the target compound, (3-isopropenyl-2,2-dimethylcyclobutyl)methyl 3-methyl-3-butenoate and (3-isopropylidene-2,2-dimethylcyclobutyl)methyl 3-methyl-3-butenoate, as an isomer mixture of 67:32:1 of the cis form, the trans form, and the regioisomer at the double bond (i.e., (3-isopropylidene-2,2-dimethylcyclobutyl)methyl 3-methyl-3-butenoate), (20.2 g, 85.6 mmol) in a yield of 99%.

The following is spectrum data of cis-(3-isopropenyl-2,2-dimethylcyclobutyl)methyl 3-methyl-3-butenoate (colorless or pale yellow oily liquid) thus produced.

IR (D-ATR): vmax=3080, 2956, 2870, 1738, 1648, 1454, 1385, 1370, 1337, 1284, 1241, 1153, 1075, 1030, 994, 889 cm $^1$H-NMR (500 MHz CDCl$_3$): δ=0.80 (3H, s), 1.19 (3H, s), 1.61 (1H, q, J=10.7 Hz), 1.64-1.65 (3H, m), 1.79-1.81 (3H, m), 1.88 (1H, dt, J=10.7, 7.5 Hz), 2.15-2.22 (1H, m), 2.39 (1H, dd, J=10.7, 7.5 Hz), 3.00-3.01 (2H, m), 3.96 (1H, dd, J=8.8, 11.1 Hz), 4.07 (1H, dd, J=6.5, 11.1 Hz), 4.56 (1H, s), 4.79-4.81 (1H, m), 4.83-4.84 (1H, m), 4.89-4.91 (1H, m) ppm $^{13}$C-NMR (150 MHz, CDCl$_3$): δ=16.09, 22.46, 22.86, 22.94, 30.91, 39.78, 41.07, 43.57, 48.81, 65.12, 109.44, 114.61, 138.52, 144.94, 171.32, ppm

Example 52

Preparation of (3-isopropylidene-2,2-dimethylcyclobutyl)methyl 2-methylbutanoate

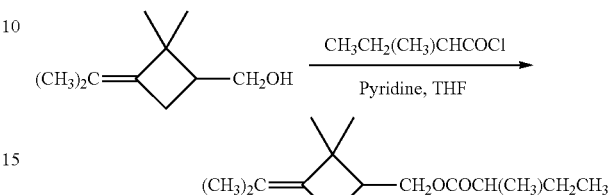

(3-Isopropylidene-2,2-dimethylcyclobutyl)methanol (9.16 g, 59.4 mmol) obtained in Example 42, tetrahydrofuran (THF) (100 g), and pyridine (14.1 g, 178 mmol) were placed in a reactor in a nitrogen atmosphere, and the mixture was stirred at 0° C. 2-Methylbutanoyl chloride (10.8 g, 89.2 mmol) was added dropwise at an internal temperature in the reactor of 15° C. or below. After the completion of the dropwise addition, the mixture was stirred for 3 hours while heating gradually up to 20° C. Subsequently, brine was added to the reaction mixture. The organic layer was separated and subjected to post-treatment by ordinary washing, drying and concentration. Then, the obtained concentrated liquid was subjected to distillation at a reduced pressure to obtain the target compound, (3-isopropylidene-2,2-dimethylcyclobutyl)methyl 2-methylbutanoate, (14.2 g, 59.4 mmol) in a yield of 100%.

The following is spectrum data of (3-isopropylidene-2,2-dimethylcyclobutyl)methyl 2-methylbutanoate (colorless or pale yellow oily liquid) thus produced.

IR (D-ATR): vmax=2964, 2935, 2878, 1735, 1461, 1383, 1361, 1264, 1240, 1186, 1152, 1081, 1013, 973, 889, 755 cm$^{-1}$ $^1$H-NMR (500 MHz CDCl$_3$): δ=0.89 (3H, t, J=7.5 Hz), 1.13 (3H, d, J=8.0 Hz), 1.13 (3H, s), 1.24 (3H, s), 1.42-1.50 (4H, m), 1.57 (3H, t, J=1.7 Hz), 1.60-1.77 (1H, m), 2.09-2.23 (2H, m), 2.30-2.39 (1H, m), 2.55-2.61 (1H, m), 4.08-4.15 (2H, m) ppm $^{13}$C-NMR (150 MHz, CDCl$_3$): δ=11.64, 16.58, 16.63, 18.50, 19.54, 21.02, 21.04, 26.72, 26.75, 27.50, 27.52, 28.40, 39.12, 39.15, 41.17, 44.20, 65.33, 122.60, 136.99, 176.73 ppm

Example 53

The mixture of cis-(3-isopropenyl-2,2-dimethylcyclobutyl)methyl acetate, trans-(3-isopropenyl-2,2-dimethylcyclobutyl)methyl acetate, and (3-isopropylidene-2,2-dimethylcyclobutyl)methyl acetate obtained as in Example 35 was separated by 10% silver nitrate silica gel column chromatography (hexane:ethyl acetate=100:1). After the separation, they were mixed in a weight ratio of 100:43:4, 100:5:1, and 100:96:96. The mixtures were loaded each on a rubber cap made of isoprene each in an amount of 200 μg of cis-(3-isopropenyl-2,2-dimethylcyclobutyl)methyl acetate to prepare Lures A, B and C shown in the Table 1 below.

TABLE 1

The loaded amounts of Lures A, B and C

| Sex pheromone | Lures (weight ratio) | | |
|---|---|---|---|
| | A | B | C |
| cis-(3-isopropenyl-2,2-dimethylcyclobutyl)methyl acetate | 200 | 200 | 200 |
| trans-(3-isopropenyl-2,2-dimethylcyclobutyl)methyl acetate | 86 | 10 | 192 |
| (3-isopropylidene-2,2-dimethylcyclobutyl)methyl acetate | 8 | 2 | 192 |

Lures A, B and C and the commercially available lure, *Pherodis Planococcus citri* (Koppert Biological Systems), were attached each to a sticky. Those and a sticky trap without a lure (blank) were placed in a navel orange field in Port Elizabeth, South Africa. Then, the number of lured and killed adult males of *Planococcus citri* (generic name: *Citrus* mealybug) in each trap was counted every other week. Each lure was changed every month. Table 2 below shows the total trap captures of male adults late September to early February.

TABLE 2

Total trap captures of male adults of *Planococcus citri*

| Lure | A | B | C | Commercially available Lure | Blank |
|---|---|---|---|---|---|
| Total trap captures | 15 | 52 | 9 | 41 | 6 |

The lure B which had the low contents of trans-(3-isopropenyl-2,2-dimethylcyclobutyl)methyl acetate and (3-isopropylidene-2,2-dimethylcyclobutyl)methyl acetate showed a luring activity similar with the commercially available lure. Meanwhile, the lures A and C which had the high contents of them did not show a luring activity. Therefore, it is surmised that trans-(3-isopropenyl-2,2-dimethylcyclobutyl)methyl acetate and (3-isopropylidene-2,2-dimethylcyclobutyl)methyl acetate have a lure-inhibitory activity.

The invention claimed is:

1. A process for preparing a dimethylcyclobutane compound,
the process comprising
reacting a dimethylcyclobutanone compound of the following general formula (2):

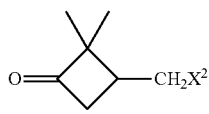

(2)

wherein $X^2$ represents a hydroxyl group, an acyloxy group having 1 to 10 carbon atoms including a carbon atom of a carbonyl group, an alkoxycarbonyloxy group having 2 to 10 carbon atoms including a carbon atom of a carbonyl group, an alkanesulfonyloxy group having 1 to 10 carbon atoms, an arenesulfonyloxy group having 6 to 20 carbon atoms, an alkoxy group having 1 to 12 carbon atoms, an aryloxy group having 6 to 12 carbon atoms, a silyloxy group having 3 to 20 carbon atoms or a halogen atom, with a phosphonic ester compound of the following general formula (3):

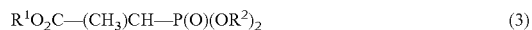

(3)

wherein $R^1$ and $R^2$ represent, independently of each other, a monovalent hydrocarbon group having 1 to 10 carbon atoms, to produce an unsaturated ester compound of the following general formula (4), having a dimethylcyclobutane ring,

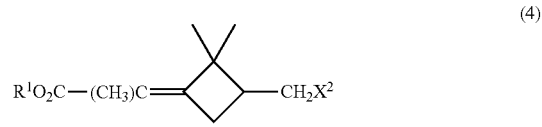

(4)

wherein $R^1$ and $X^2$ are as defined above; and
subjecting the unsaturated ester compound (4), having a dimethylcyclobutane ring, to a reduction reaction to produce a dimethylcyclobutane compound of general formula (1A):

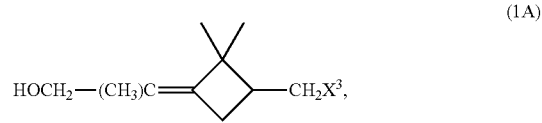

(1A)

wherein $X^3$ represents a hydroxyl group, an alkanesulfonyloxy group having 1 to 10 carbon atoms, an arenesulfonyloxy group having 6 to 20 carbon atoms, an alkoxy group having 1 to 12 carbon atoms, an aryloxy group having 6 to 12 carbon atoms, a silyloxy group having 3 to 20 carbon atoms or a halogen atom.

2. The process according to claim 1 for preparing the dimethylcyclobutane compound,
the process further comprising:
changing the hydroxyl group and, optionally, $X^3$ in the dimethylcyclobutane compound (1A) to produce a dimethylcyclobutane compound of general formula (1B):

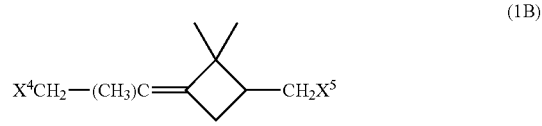

(1B)

wherein $X^4$ represents an acyloxy group having 1 to 10 carbon atoms including a carbon atom of a carbonyl group, an alkoxycarbonyloxy group having 2 to 10 carbon atoms including a carbon atom of a carbonyl group, an alkanesulfonyloxy group having 1 to 10 carbon atoms, an arenesulfonyloxy group having 6 to 20 carbon atoms, an alkoxy group having 1 to 12 carbon atoms, an aryloxy group having 6 to 12 carbon atoms, a silyloxy group having 3 to 20 carbon atoms, a trialkylphosphonio group having 3 to 30 carbon atoms, a triarylphosphonio group having 12 to 30 carbon atoms or a halogen atom; and $X^5$ represents a hydroxyl group, an acyloxy group having 1 to 10 carbon atoms including a carbon atom of a carbonyl group, an alkoxycarbonyloxy group having 2 to 10 carbon atoms including a carbon atom of a carbonyl group, an alkanesulfonyloxy group having 1 to 10 carbon atoms, an arenesulfonyloxy group having 6 to 20 carbon atoms, an alkoxy group having 1 to 12 carbon atoms, an aryloxy group having 6 to 12 carbon atoms, a silyloxy group having 3 to 20 carbon atoms or a halogen atom.

3. A process for preparing an isopropenyl dimethylcyclobutane compound and/or an isopropylidene dimethylcyclobutane compound, the process comprising
subjecting a dimethylcyclobutane compound of the following general formula (1):

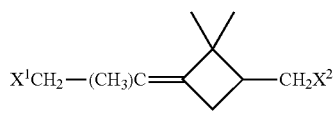

(1)

wherein $X^1$ represents a hydroxyl group, an acyloxy group having 1 to 10 carbon atoms including a carbon atom of a carbonyl group, an alkoxycarbonyloxy group having 2 to 10 carbon atoms including a carbon atom of a carbonyl group, an alkanesulfonyloxy group having 1 to 10 carbon atoms, an arenesulfonyloxy group having 6 to 20 carbon atoms, an alkoxy group having 1 to 12 carbon atoms, an aryloxy group having 6 to 12 carbon atoms, a silyloxy group having 3 to 20 carbon atoms, a trialkylphosphonio group having 3 to 30 carbon atoms, a triarylphosphonio group having 12 to 30 carbon atoms or a halogen atom; and $X^2$ represents a hydroxyl group, an acyloxy group having 1 to 10 carbon atoms including a carbon atom of a carbonyl group, an alkoxycarbonyloxy group having 2 to 10 carbon atoms including a carbon atom of a carbonyl group, an alkanesulfonyloxy group having 1 to 10 carbon atoms, an arenesulfonyloxy group having 6 to 20 carbon atoms, an alkoxy group having 1 to 12 carbon atoms, an aryloxy group having 6 to 12 carbon atoms, a silyloxy group having 3 to 20 carbon atoms or a halogen atom, to a reduction reaction to produce an isopropenyl dimethylcyclobutane compound (5) of general formula (5):

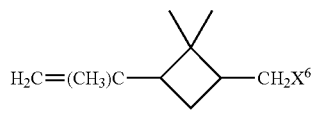

(5)

wherein $X^6$ represents a hydroxyl group, an acyloxy group having 1 to 10 carbon atoms including a carbon atom of a carbonyl group, an alkoxycarbonyloxy group having 2 to 10 carbon atoms including a carbon atom of a carbonyl group, an alkanesulfonyloxy group having 1 to 10 carbon atoms, an arenesulfonyloxy group having 6 to 20 carbon atoms, an alkoxy group having 1 to 12 carbon atoms, an aryloxy group having 6 to 12 carbon atoms, a silyloxy group having 3 to 20 carbon atoms or a halogen atom, and/or an isopropylidene dimethylcyclobutane compound of general formula (6):

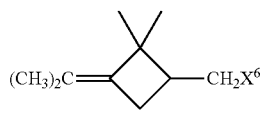

(6)

wherein $X^6$ is as defined above.

4. The process according to claim 3 for preparing the isopropenyl dimethylcyclobutane compound and/or the isopropylidene dimethylcyclobutane compound, the process further comprising:
changing a specific group, $X^6$, in the isopropenyl dimethylcyclobutane compound (5) and/or the isopropylidene dimethylcyclobutane compound (6) to another group, $X^{6'}$, among the options for $X^6$ defined above, to produce the isopropenyl dimethylcyclobutane compound (5') and/or the isopropylidene dimethylcyclobutane compound (6').

5. A dimethylcyclobutane compound of the following general formula (1):

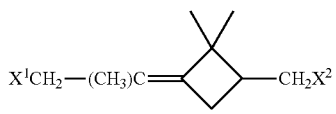

(1)

wherein $X^1$ represents a hydroxyl group, an acyloxy group having 1 to 10 carbon atoms including a carbon atom of a carbonyl group, an alkoxycarbonyloxy group having 2 to 10 carbon atoms including a carbon atom of a carbonyl group, an alkanesulfonyloxy group having 1 to 10 carbon atoms, an arenesulfonyloxy group having 6 to 20 carbon atoms, an alkoxy group having 1 to 12 carbon atoms, an aryloxy group having 6 to 12 carbon atoms, a silyloxy group having 3 to 20 carbon atoms, a trialkylphosphonio group having 3 to 30 carbon atoms, a triarylphosphonio group having 12 to 30 carbon atoms or a halogen atom; and $X^2$ represents a hydroxyl group, an acyloxy group having 1 to 10 carbon atoms including a carbon atom of a carbonyl group, an alkoxycarbonyloxy group having 2 to 10 carbon atoms including a carbon atom of a carbonyl group, an alkanesulfonyloxy group having 1 to 10 carbon atoms, an arenesulfonyloxy group having 6 to 20 carbon atoms, an alkoxy group having 1 to 12 carbon atoms, an aryloxy group having 6 to 12 carbon atoms, a silyloxy group having 3 to 20 carbon atoms or a halogen atom.

* * * * *

UNITED STATES PATENT AND TRADEMARK OFFICE
CERTIFICATE OF CORRECTION

PATENT NO. : 11,384,043 B2
APPLICATION NO. : 16/930570
DATED : July 12, 2022
INVENTOR(S) : Ishibashi et al.

It is certified that error appears in the above-identified patent and that said Letters Patent is hereby corrected as shown below:

In the Specification

Column 2, Line 16: Please correct "[Non-Patent Literature 5]. Chem." to read --[Non-Patent Literature 5]. J. Chem.--

Column 25, Line 45: Please correct "$X^1$" to read --$X^{12}$--

Column 31, Line 26: Please correct "(F)" to read --(1F)--

Column 31, Line 59: Please correct "(G)" to read --(1G)--

Column 36, Line 33: Please correct "(F)" to read --(1F)--

Column 51, Line 27: Please correct "(60)" to read --(6G)--

Column 52, Line 20: Please correct "(50)" to read --(5G)--

Column 52, Line 22: Please correct "(60)" to read --(6G)--

Column 57, Line 6: Please correct "10 g to 1000 mg" to read --10 µg to 1000 mg--

Column 58, Line 9: Please correct "cm" to read --$cm^{-1}$--

Column 66, Line 53: Please correct "3.32-3.37 (2, m)," to read --3.32-3.37 (2H, m),--

Column 67, Line 44: Please correct "2.07-2.23 (21-, m)," to read --2.07-2.23 (2H, m),--

Column 72, Line 39: Please correct "wen" to read --were--

Column 73, Line 59: Please correct "(311, t, J=1.9 Hz)" to read --(3H, t, J=1.9 Hz)--

Signed and Sealed this
Fifteenth Day of August, 2023

Katherine Kelly Vidal
*Director of the United States Patent and Trademark Office*

CERTIFICATE OF CORRECTION (continued)
U.S. Pat. No. 11,384,043 B2

Column 73, Lines 60-61: Please correct "(11, d, J 11.8 Hz)," to read --(1H, d, J=11.8 Hz),--

Column 85, Line 1: Please correct "E:Z=50:50 of 16 (3-" to read --E:Z=50:50 of (3- --

Column 88, Lines 20-21: Please correct "double bond (i.e., 6 (3-isopropylidene-2,2-" to read --double bond (i.e., (3-isopropylidene-2,2- --

Column 90, Line 52: Please correct "(31, t, J=1.9 Hz)," to read --(3H, t, J=1.9 Hz),--

Column 93, Line 56: Please correct "cm" to read --$cm^{-1}$--